United States Patent
Quinn

(10) Patent No.: US 11,400,141 B2
(45) Date of Patent: *Aug. 2, 2022

(54) METHODS FOR TREATING LYSOSOMAL ACID LIPASE DEFICIENCY IN PATIENTS

(71) Applicant: ALEXION PHARMACEUTICALS, INC., Boston, MA (US)

(72) Inventor: Anthony Quinn, Chestnut Hill, MA (US)

(73) Assignee: Alexion Pharmaceuticals, Inc., Boston, MA (US)

(*) Notice: Subject to any disclaimer, the term of this patent is extended or adjusted under 35 U.S.C. 154(b) by 533 days.

This patent is subject to a terminal disclaimer.

(21) Appl. No.: 16/190,878

(22) Filed: Nov. 14, 2018

(65) Prior Publication Data

US 2019/0282671 A1 Sep. 19, 2019

Related U.S. Application Data

(63) Continuation of application No. 14/851,387, filed on Sep. 11, 2015, now Pat. No. 10,166,274, which is a continuation of application No. 14/633,240, filed on Feb. 27, 2015, now abandoned, which is a continuation of application No. 14/102,000, filed on Dec. 10, 2013, now abandoned, which is a continuation of application No. 13/229,558, filed on Sep. 9, 2011, now Pat. No. 8,663,631, which is a continuation-in-part of application No. PCT/US2011/033699, filed on Apr. 23, 2011.

(60) Provisional application No. 61/432,372, filed on Jan. 13, 2011, provisional application No. 61/456,014, filed on Oct. 29, 2010, provisional application No. 61/403,011, filed on Sep. 9, 2010.

(51) Int. Cl.
| | |
|---|---|
| *A61K 38/46* | (2006.01) |
| *C12N 9/20* | (2006.01) |
| *C12N 9/18* | (2006.01) |
| *A61K 31/135* | (2006.01) |
| *A61K 31/366* | (2006.01) |
| *A61K 31/397* | (2006.01) |
| *A61P 3/06* | (2006.01) |
| *A61K 31/138* | (2006.01) |
| *A61K 45/06* | (2006.01) |

(52) U.S. Cl.
CPC .......... *A61K 38/465* (2013.01); *A61K 31/135* (2013.01); *A61K 31/138* (2013.01); *A61K 31/366* (2013.01); *A61K 31/397* (2013.01); *A61K 45/06* (2013.01); *A61P 3/06* (2018.01); *C12N 9/18* (2013.01); *C12N 9/20* (2013.01); *C12Y 301/01013* (2013.01)

(58) Field of Classification Search
CPC .......... C12N 9/20; A61K 38/46; A61K 38/465
See application file for complete search history.

(56) References Cited

U.S. PATENT DOCUMENTS

| | | |
|---|---|---|
| 5,767,115 A | 6/1998 | Rosenblum et al. |
| 5,929,304 A | 7/1999 | Radin et al. |
| 6,534,300 B1 | 3/2003 | Canfield |
| 6,670,165 B2 | 12/2003 | Canfield |
| 6,800,472 B2 | 10/2004 | Canfield et al. |
| 6,849,257 B2 | 2/2005 | Grabowski et al. |
| 7,033,780 B1 | 4/2006 | McCarthy et al. |
| 8,124,732 B2 | 2/2012 | Harvey |
| 8,178,609 B2 | 5/2012 | Grynkiewicz et al. |
| 8,183,003 B2 | 5/2012 | Crawford et al. |
| 8,232,073 B2 | 7/2012 | Crawford et al. |
| 8,663,631 B2 | 3/2014 | Quinn |
| 8,846,603 B2 | 9/2014 | Quinn et al. |
| 8,945,542 B2 | 2/2015 | Heartlein et al. |
| 2002/0193303 A1 | 12/2002 | Kapeller-Libermann |
| 2003/0059420 A1 | 3/2003 | Grabowski et al. |
| 2003/0064467 A1 | 4/2003 | Baker et al. |
| 2004/0038365 A1 | 2/2004 | Xiao |
| 2004/0175798 A1 | 9/2004 | Wan et al. |
| 2004/0223960 A1 | 11/2004 | Grabowski et al. |
| 2005/0112691 A1 | 5/2005 | Callewaert et al. |
| 2005/0181474 A1 | 8/2005 | Giordano et al. |
| 2007/0009500 A1 | 1/2007 | Blazar et al. |
| 2007/0264249 A1 | 11/2007 | Grabowski et al. |
| 2007/0267249 A1 | 11/2007 | Cullen |
| 2007/0270364 A1 | 11/2007 | Janknecht |
| 2007/0270367 A1 | 11/2007 | Testa et al. |

(Continued)

FOREIGN PATENT DOCUMENTS

| | | |
|---|---|---|
| EP | 1267914 B1 | 4/2009 |
| RU | 2140983 C1 | 11/1999 |

(Continued)

OTHER PUBLICATIONS

LIPA ("LIPA Gene", Genecards, available at www.genecards.org/cgi-bin/carddisp.pl?gene=LIPA, accessed on Mar. 13, 2021). (Year: 2021).*

(Continued)

*Primary Examiner* — Robert J Yamasaki
*Assistant Examiner* — Charles Zoltan Constantine
(74) *Attorney, Agent, or Firm* — Clark & Elbing LLP

(57) ABSTRACT

The present invention provides methods of treating LAL deficiency comprising administering to a mammal a therapeutically effective amount of lysosomal acid lipase with an effective dosage frequency. Methods of improving growth and river function, increasing LAL tissue concentration, and increasing LAL activity in a human patient suffering from LAL deficiency are also provided.

10 Claims, 19 Drawing Sheets

Specification includes a Sequence Listing.

(56) References Cited

U.S. PATENT DOCUMENTS

| | | |
|---|---|---|
| 2008/0025958 A1 | 1/2008 | Hannon et al. |
| 2008/0025959 A1 | 1/2008 | Daneman et al. |
| 2008/0206223 A1 | 8/2008 | Van Bree et al. |
| 2008/0249287 A1 | 10/2008 | Rossomando et al. |
| 2008/0255050 A1 | 10/2008 | Guo |
| 2008/0292618 A1 | 11/2008 | Weisbart |
| 2009/0178147 A1 | 7/2009 | Harvey |
| 2009/0297496 A1 | 12/2009 | Grabowski |
| 2010/0062982 A1 | 3/2010 | Harvey |
| 2010/0160253 A1 | 6/2010 | Coombe et al. |
| 2010/0184947 A1 | 7/2010 | Kuik-Romeijn et al. |
| 2010/0196393 A1 | 8/2010 | Banks et al. |
| 2010/0233084 A1 | 9/2010 | Narasimhaswamy et al. |
| 2010/0291060 A1 | 11/2010 | Sturk et al. |
| 2011/0091442 A1 | 4/2011 | Boyd et al. |
| 2011/0213328 A1 | 9/2011 | Keimel et al. |
| 2011/0230416 A1 | 9/2011 | Khrestchatisky et al. |
| 2012/0064055 A1 | 3/2012 | Quinn |
| 2012/0093795 A1 | 4/2012 | Garcia et al. |
| 2012/0190642 A1 | 7/2012 | Grynkiewicz et al. |
| 2012/0232133 A1 | 9/2012 | Balazs et al. |
| 2012/0288447 A1 | 11/2012 | Lee et al. |
| 2013/0027021 A1 | 1/2013 | Gokhale |
| 2013/0095092 A1 | 4/2013 | Quinn et al. |
| 2013/0209436 A1 | 8/2013 | Quinn et al. |
| 2013/0273021 A1 | 10/2013 | Quinn et al. |
| 2015/0030582 A1 | 1/2015 | Harvey et al. |

FOREIGN PATENT DOCUMENTS

| | | |
|---|---|---|
| RU | 2008134120 A | 2/2010 |
| WO | 1991/18923 A1 | 12/1991 |
| WO | 1992/16212 A1 | 10/1992 |
| WO | 1995/008532 A1 | 3/1995 |
| WO | 96/04001 A1 | 2/1996 |
| WO | 97/05771 A2 | 2/1997 |
| WO | 98/11206 A2 | 3/1998 |
| WO | 00/09153 A1 | 2/2000 |
| WO | 000/77239 A2 | 12/2000 |
| WO | 01/56596 A1 | 8/2001 |
| WO | 01/97829 A2 | 12/2001 |
| WO | 2007/030375 A2 | 3/2007 |
| WO | 2007/084737 A2 | 7/2007 |
| WO | 2007/137303 A2 | 11/2007 |
| WO | 2010/033854 A2 | 3/2010 |
| WO | 2011/133960 A2 | 10/2011 |
| WO | 2012/050695 A1 | 4/2012 |
| WO | 2012/112677 A2 | 8/2012 |
| WO | 2012/112681 A1 | 8/2012 |
| WO | 2012/159052 A2 | 11/2012 |
| WO | 2012/162807 A1 | 12/2012 |
| WO | 2012/177639 A2 | 12/2012 |
| WO | 2012/177778 A1 | 12/2012 |
| WO | 2013/020064 A1 | 2/2013 |

OTHER PUBLICATIONS

Rajamohan ("Crystal Structure of human lysosomal acid lipase and its implications in cholesteryl ester storage disease" Journal of Lipid Research, 2020, vol. 61, 1192-1202) (Year: 2020).*

Ries et al., "A new mutation in the gene for lysosomal acid lipase leads to Wolman disease in an African kindred," Journal of Lipid Research, 37:1761-1762 (1996).

Riva et al., "Hepatocarcinoma in a child with cholesterol ester storage disease," Digestive and Liver Disease, 40:784 (2008).

Rosenbaum et al., "Thiadiazole Carbamates: Potent Inhibitors of Lysosomal Acid Lipase and Potential Neimann-Pick Type C Disease Therapeutics," J Med Chem., 53(14):5281-5289 (2010).

Rosenthal, "Nonalcoholic Fatty Liver Disease in Pediatric Patients—A Problem that is 'Enormous' and 'Growing,'" JPEN J Parenter Enteral Nutr 36:7S (2012).

Rothe, et al., "Altered mononuclear phagocyte differentiation associated with genetic defects of the lysosomal acid lipase," Atherosclerosis, 130:215-221 (1997).

Roussel et al., "Crystal Structure of Human Gastric Lipase and Model of Lysosomal Acid Lipase, Two Lipolytic Enzymes of Medical Interest," The Journal of Biological Chemistry, 274(24):16995-17002 (1999).

Röyttä et al., "Wolman disease: morphological, clinical and genetic studies on the first Scandinavian cases," Clin Genet, 42:1-7 (1992).

Russell et al., "Recombinant proteins for genetic disease," Clin Gent 55:389-394 (1999).

Salvetti et al., "Gene therapy of lysosomal storage disorders," British Medical Bulletin, 51(1):106-122 (1995).

Sando et al., "Intercellular Transport of lysosomal acid lipase mediates lipoprotein cholesteryl ester metabolism in a human vascular endothelial cell-fibroblast coculture system," Cell Regulation, 1:661-674 (1990).

Schaub et al., "Wolman's Disease: Clinical, Biochemical and Ultrastructural in an Unusual Case Without Striking Adrenal Calcification" Eur. J. Ped., 135:45-53 (1980).

Schiff et al., "Hepatic Cholesterol Ester Storage Disease, A Familial Disorder," American Journal of Medicine, 14:538-546 (1968).

Yu et al., "Boosting Brain Uptake of a Therapeutic Antibody by Reducing Its Affinity for a Transcytosis Target," Sci Fransl Med, 3:84ra44 (2011).

Phillipps et al., "Secretion of insulin-like growth factor-II into bile of rats of different ages," Biol Neonate, 78(2):106-12 (2000).

Seedorf et al., "A Novel Variant of Lysosomal Acid Lipase (Lue336 Pro) Associated With Acid Lipase Deficiency and Cholesterol Ester Storage Disease," Arteriosclerosis, Thrombosis, and Vascular Biology, 15:773-778 (1995).

Shimada et al., "Suppression of diet-induced atherosclerosis in low density lipoprotein receptor knockout mice overexpressing lipoprotein lipase," Proc. Natl. Acad. Sci. USA, 93:7242-7246 (1996).

Skinner et al., "Cholesterol Curves to Identify Norms by Age and Sex in Healthy Weight Children," Clin Pediatr, 51:233 (2012).

Sloan et al., "Enzyme Deficiency in Cholesteryl Ester Storage Disease," the Journal of Clinical Investigation, 51:1923-1924 (1972).

Sly et al., "Enzyme therapy in mannose receptor-null mucopolysaccharidosis VII mice defines roles for the mannose 6-phosphate and mannose receptors," PNAS, 103(41):15172-15177 (2006).

Spiegel-Adolf et al., "Hematologic Studies in Niemann-Pick and Wolman's Disease," Confin. Neurol, 28:399-406 (1966).

Stahl et al., "Evidence for receptor-mediated binding of glycoproteins, glycoconjugates, and lysosomal gylcosidases by alveolar macrophages," Cell Biology, 75(3):1399-1403 (1978).

Sternby et al., "Carboxyl Ester Lipase (Bile Salt-Stimulated Lipase), Colipase, Lipase, and Phospholipase A2 Levels in Pancreatic Enzyme Supplements," Scand J Gastroenterol 32:261-267 (1997).

Surve et al., "Wolman Disease: Diagnosis by Leucocyte Acid Lipase Estimation," Indian Journal of Pediatrics, 72:353-354 (2005).

Suzuki et al., "Are animal models useful for understanding the pathophysiology of lysosomal storage disease?" Acta Paediatr Suppl, 443:54-62 (2003).

Takahashi et al., "Distribution of murine mannose receptor expression from early embryogenesis through to adulthood," Cell Tissue Res 292:311-323 (1998).

Takasaki et al., "Structure of the N-Asparagine-linked Oligosaccharide Units of Human Placental β-Glucocerebrosidase," The Journal of Biological Chemistry, 259(16):10112-10117 (1984).

Tarantino et al., "Lovastatin therapy for cholesterol ester storage disease in two sisters," The Journal of Ped., 118(1):131-135 (1991).

Thompson et al., "Role of cholesterol in regulating apolipoprotein B secretion by the liver," Journal of Lipid Research, 37:439-440 (1996).

Todoroki et al., "Accumulated lipids, aberrant fatty acid composition and defective cholesterol ester hydrolase activity in cholesterol ester storage disease," Ann Clin Biochem, 37:187-193 (2000).

Tolar et al., "Long-term metabolic, endocrine, and neuropsychological outcome of hematopoietic cell transplantation for Wolman disease," Bone Marrow Transplantation, 43:21-27 (2009).

Uniyal et al., "Wolman's Disease," Indian Pediatrics, 32:232-233 (1995).

(56) References Cited

OTHER PUBLICATIONS

Van Berkel, "The role of non-parenchymal cells in liver metabolism," TIBS 202-205, Sep. 1979.
Van Erum et al., "Cholesteryl Ester Storage Disease with Secondary Lecithin Cholesterol Acyl Transferase Deficiency," J. Inher. Metab. Dis 11 Suppl. 2:146-148 (1988).
Varki et al., "Studies of synthesis, structure and function of the phosphorylated oligosaccharides of lysosomal anzymes," J. Biosci, 5(1):101-104 (1983).
Vom Dahl et al., "Lysosomal storage disease as differential diagnosis of hepatosplenomegaly," Best Practice & Research Clinical Gastroenterology, 24:619-628 (2010).
Von Figura et al., "Lysosomal Enzymes and Their Receptors," Ann. Rev. Biochem, 55:167-193 (1986).
Vuillemenot et al., "Intrathecal tripeptidyl-peptidase 1 reduces lysosomal storage in a canine model of late infantile neuronal ceroid lipofuscinosis," Molecular Genetics and Metabolism, 104:325-337 (2011).
Walters et al., "Cholesterol esterase activities in commercial pancreatic enzyme preparations and implications for use in pancreatic insufficient cystic fibrosis," Journal of Clinical Pharmacy and Therapeutics, 26:425-431 (2001).
Wang et al., "SREBP-1, a Membrane-bound Transcription Factor Released by Sterol-Regulated Proteolysis," Cell, 77:53-62 (1994).
Warner et al., "Separation and Characterization of the Acid Lipase and Neutral Esterases from Human Liver," Am. J. Hum Genet, 32:869-879 (1980).
Warner et al., "Purification of the Lysosomal Acid Lipase from Human Liver and Its Role in Lysosomal Lipid Hydorlysis," The Journal of Biological Chemistry, 246(6):2952-2957 (1981).
Wolman, "Proposed Treatment for Infants With Wolman Disease," Pediatrics, 83:1074-1075 (1989).
Wolman, "Primary Familial Xanthomatosis with Involvement and Calcification of the Adrenals: Report of Two or More Dases in Siblings of a Previously Described Infant," Pediatrics, 28:742-757 (1961).
Xu et al., "Turnover and Distribution of Intravenously Administered Mannose-Terminated Human Acid [beta]-Glucosidase in Murine and Human Tissues," Pediatric Research, 39(2):313-322 (1996).
Yagyu et al., "Overexpressed lipoprotein lipase protects against atherosclerosis in apolipoprotein E knockout mice," Journal of Lipid research, 40:1677:1678 (1999).
Yan et al., "Macrophage-Specific Expression of Human Lysosomal Acid Lipase Corrects Inflammation and Pathogenic Phenotypes in lal-/-Mice," The American Journal of Pathology, 169(3):916-917 (2006).
Yokoyama et al., "Long-term treatment of a homozygous cholesteryl ester storage disease with combined cholestryamine and lovastatin," J. Inher. Metab. Dis. 15:219-292 (1992).
Zhang et al., "Biotherapeutic target or sink: analysis of the macrophage mannose receptor tissue distribution in murine models of lysosomal storage diseases," J. Inherit Metab Disl 34:795-809 (2011).
Young et al., "Deficiency of Acid Esterase Activity in Wolman's Disease," Archives of Disease in Childhood, 45:664-665 (1970).
Zuliani et al., "Characterization of a New Form of Inherited Hypercholesterolemia: Familial Recessive Hypercholesterolemia," Arterioscler Throm Vase Biol, 19:802-809 (1999).
Mori et al., "Identification of the Mannan-Binding Protein from Rat Livers as a Hepatocyte Protein Distinct from the Mannan Receptor on Sinusoidal Cells," Archives of Biochemistry and Biophysics, 222(2):542-552 (1983).
Muntoni et al., "Prevalence of Cholesteryl Ester Storage Disease," Arterioscler. Thomb. Vase. Biol., 27:1866-1868 (2007).
Muntoni et al., "Homozygosity for a splice junction mutation in exon 8 of the gene encoding lysosomal acid lipase in a Spanish kindred with cholesterol ester disease (CESD)," Hum Genet, 95:491-494 (1995).
Muntoni et al., "A missense mutation (Thr-6Pro) in the lysosomal acid lipase (LAL) gene is present with a high frequency in three different ethnic populations: impact on serum lipoprotein concentrations," Hum Genet, 97:265-267 (1996).
Nakagawa et al., "Cloning of rat lysosomal acid lipase cDNA and identification of the mutation in the rat model of Wolman's disease," J. Lipra Res 36:2212-2213 (1995).
Nègre-Salvayre et al., "UV-treated lipoproteins J. Lipid Res. as a model system for the study of the biological effects of lipid peroxides on cultured cells. 4. Calcium is involved in the cytotoxicity of UV-treated LDL on lymphoid cell lines," Biochimica et Biophysica Acta, 1123:1207-215 (1992).
Nobili et al., "Treatment of nonalcoholic fatty liver disease in adults and children: a closer look at the arsenal," J Gastroenterol, (2011). DOI 10.1007/s00535-011-0467.
Noorman et al., "The mannose receptor, localization and role in the clearance of tissue-type plasminogen activator," Fibrinolysis & Proteolysis, 12(4):241-250 (1998).
Odievre, "Clinical presentation of Metabolic Liver Disease," J. Inher. Metab. Dis., 14:526-530 (1991).
Özmen et al., "Wolman's disease: ultrasonographic and computed tomographic findings," Pediatr Radiol, 22:541-542 (1992).
Ameis et al., "Lysosomal acid lipase: A pivotal enzyme in the pathogenesis of cholesteryl ester storage disease and Wolman disease," Z Gastroenterol (Suppl. 3) 34:66-67 (1996).
Beaudet et al., "Acid lipase in cultured fibroblasts: cholesterol ester storage disease," J. Lab. Clin. Med., 84:54-55 (1974).
Brown et al., "Use of Nile Red Stain in the Detection of Cholesteryl Ester Accumulation in Acid Lipase-Deficient Fibroblasts," Arch Pathol Lab Med, 112:295-296 (1988).
Carter et al., "Cholesterol Ester Storage Disease," Pediat. Radiol, 2:135-136 (1974).
Coelho et al., "Cholesterylester Storage Disease Report of a case," Arq Gastroenterol, 24(3/4):184-187, (1987).
Dincsoy et al., "Cholesterol Ester Storage Disease and Mesenteric Lipodystrophy," Am. J. Pathol., 81:263-264 (1984).
Drevon et al., "The Effects of Cholesterol/Fat Feeding on Lipid Levels and Morphological Structures in Liver, Kidney and Spleen in Guinea Pigs," Acta path. microbial. scand. Sect. A, 85:1-18 (1977).
Edelstein, et al., "Cholesteryl Ester Storage Disease: A Patient with Massive Splenomegaly and Splenic Abscess," The American Journal of Gastroenterology, 83:687-688. (1988).
Elleder et al., "Subclinical course of cholesterol ester storage disease (CESD) diagnosed in adulthood," Virchows Archiv A Pathological Anatomy and Histopathology, 416:3457-365 (1990).
Ferry et al., "Liver Transplantation for Cholesteryl Ester Storage Disease," Journal of Pediatric Gastroenterology and Nutrition, 12:376-378 (1991).
Fulcher, et al., "Pediatric Case of the Day", RadioGraphics, 18(2):533-534 (1988).
Haller et al., "Gallbladder Dysfunction in Cholesterol Ester Storage Disease," JPGN, 50(5):556-557 (2010).
Hill et al., "CT Findings in Acid Lipase Deficiency: Wolman Disease and Cholesteryl Ester Storage Disease," Journal of Computer Assisted Tomography, 7(5):815-818 (1983).
Iverson et al., "Asymptomatic cholesteryl ester storage disease in an adult controlled with simvastatin," Ann Clin Biochem, 34:433-436 (1997).
Jeschke et al., "Cholesteryl Ester Storage Disease, Clinical and Morphological Aspects," Cholesterylester-Speicherkrankheit, 120(8):601-604 (1982).
Justus et al., "Lebermorphologie und Klinik eins Falls von Cholesterinester-Speicherkrankheit," Dtsch. Z. Verdau-Stoffwechs. krankh. 48:198-207 (1988).
Künnert et al., "Zur Diagnostik und Morphologic der Leber bei Cholesterolester-Speicher-krankheit," ZbL Allg. Pathol. a. pathol. Anat. 123:71-84 (1979).
Künnert et al., "Cholesteryl ester storage disease and sea-blue histiocytes," Zentralbl. Allg. Pathol. Pathol. Anat. 133:517-525 (1987).
Kuntz et al., "Cholesterinester-Speicherkrankheitder Leber," Leber Magen Darm 11, Nr. 6:258-263 (1981).

(56) References Cited

OTHER PUBLICATIONS

Leone et al., "Use of simvastatin plus cholestyramine in the treatment of lysosomal acid lipase deficiency," The Journal of Pediatrics, 119(6):1008-1009 (1991).
Leone et al., "Treatment and liver transplantation for cholesterol ester storage disease," The Journal of Pediatrics, 127(3):509-510 (1995).
Liu et al., "Phenotypic Correction of Feline Lipoprotein Lipase Deficiency by Adenoviral Gene Transfer," Human Gene Therapy, 11:21-32 (2000).
Pfeifer et al., "Cholesteryl Ester Storage Disease: Report on Four Cases," Virchows Arch. B. Cel Path. 33:17-34 (1980).
Pisciotta et al., "Cholesteryl Ester Storage Disease (CESD) due to novel mutations in the LIPA gene," Molecular Genetics and Metabolism, 79:143-148 (2009).
Rassoul et al., "Long-term administration of the HMG-CoA reductase inhibitor lovastatin in two patients with cholesteryl ester storage disease," International Journal of Clinic Pharmacology and Therapeutics, vol. 39, No. 5:199-204 (2001).
Salvayre et al., "Maladie de Wolman et polycorie cholestérolique de l'adulte (cholesteryl ester storage disease): Nuoveaux moyens d'étude et de diagnostic," Ann. Biol. Clin. 44:611-617 (1986).
Sanyal et al., "Endpoints and Clinical Trial Design for Nonalcoholic Steatohepatitis," Hepatology, 54(1):344-345 (2011).
Thavarungkul et al., "Cholesterol Ester Storage Disease: A Reported Case," J. Med. Assoc. Tha; 78(3):165-165.
Tylki-Szyma?ska et al, "Clinical, biochemical and histological analysis of seven patients with cholesteryl ester storage disease," Acta Paediatrica Japonica, 39:643-646 (1997).
Pagani et al., "Cysteine residues in human lysosomal acid lipase are involved in selective cholesteryl esterase activity," Biochem J. 326:265-269 (1997).
Pagani et al., "A histidine to tyrosine replacement in lysosomal acid lipase causes cholesteryl ester storage disease," Human Molecular Genetics, 3(9): 1605-1609 (1994).
Pagani et al., "Expression of lysosomal acid lipase mutants detected in three patients with cholesteryl ester storage disease," Human Molecular Genetics, 5(10):1611-1617 (1996).
Patrick et al., "Deficiency of an Acid Lipase in Wolman's Disease," Nature, 222:1067-1068 (1969).
Pentchev et al., "Incorporation of Exogenous Enzymes into Lysosomes: A Theoretical and Practical Means for Correcting Lysosomal Blockage," American Chemical Society, 150-151 (1978).
Poorthuis et al., "The frequency of lysosomal storage disease in The Netherlands," Hum genet, 105:151-156 (1999).
Poup?tová et al., "LSDS with Neurologic Involvement: The birth prevalence of lysosomal storage disorders in the Czech Republic: comparison with data in different populations," J. Inherit Metab Dis, 33:387-396 (2010).
Raivio et al., "Genetic Diseases of Metabolism," Annu. Rev. Biochem 41:543-576 (1972).
Redonnet-Vernhet et al., "Cholesteryl Ester Storage Disease: Relationship between Molecular Defects and in Situ Activity of Lysosomal Acid Lipase," Biochemical and Molecular Medicine, 62:42-49 (1997).
Ries et al., "Different Missense Mutations in Histidine-108 of Lysosomal Acid Lipase Cause Cholesteryl Ester Storage Diseases in Unrelated Compound Heterozygous and Hemizygous Individuals," Human Mutation, 12:44-51 (1998).
Ries et al., "Transcriptional regulation of lysosomal acid lipase in differentiating monocytes is mediated by transcription factors Sp1 and AP-2," Journal of Lipid Research, 39:2125-2126 (1998).
De Duve "The Participation of Lysosomes in the Transformation of Smooth Muscle Cells to Foamy Cells in the Aorta of Cholesterol-Fed Rabbits," Acta Cardiologica Suppl., pp. 9-25 (1975).
De Grey et al., "Medical Bioremediation: Prospects for the Application of Microbial Catabolic Diversity to aging and Several Major Age-Related Diseases," Ageing Research Reviews, 4:315-338 (2005).

Decarlis et al., "Combined Hyperlipidaemia as a Presenting Sign of Cholesteryl Ester Storage Disease," JIMD Short Report, Online, 3 pages (2009).
Desai et al., "Cholesteryl Ester Storage Disease: Pathologic Changes in an Affected Fetus," American Journal of Medical Genetics, 26:689-698 (1987).
Desnick et al., "Toward Enzyme Therapy for Lysosomal Storage Diseases," Physiological Reviews, 56(1):56-98 (1976).
Di Bisceglie, Cholesteryl Ester Storage Disease: Hepatopathology and Effects of Therapy with Lovastatin, Hepatology, 11(5):764-772 (1990).
Doebber et al., "Enhanced Macrophage Uptake of Synthetically Glycosylated Human Placental β-Glucocerebrosidase," The Journal of Biological Chemistry, 257(5):2193-2199 (1982).
Drebber et al., "Severe Chronic Diarrhea and Weight Loss in Cholesteryl Ester Storage Disease: A Case Report," World Journal Gastroenterol, 11(15):2364-2366 (2005).
Du et al., "Human Transcription Factor USF Stimulates Transcription through the Initiator Elements of the HIV-1 and the Ad-ML Promoters," The EMBO Journal, 12(2):501-511 (1993).
Du et al., "Lysosomal Acid Lipase-Deficient Mice: Depletion of White and Brown Fat, Severe Hepatosplenomegaly, and Shortened Life Span," Journal of Lipid Research, 42(4):489-500 (2001).
Du et al., "Reduction of Atherosclerotic Plaques by Lysosomal Acid Lipase Supplementation," Arterioscler Thromb. Vasc. Biol., 24:147-154 (2004).
Du et al., "Lysosomal Acid Lipase and Atherosclerosis," Curr. Opin. Lipidol., 15:539-544 (2004).
Du et al., "Mouse Lysosomal Acid Lipase: Characterization of the Gene and Analysis of Promoter Activity," Gene, 208:285-295(1998).
Dustin et al., "A Mannose 6-Phosphate-Containing N-Linked Glycopeptide Derived from Lysosomal Acid Lipase is Bound to MHC ClassII in B Lymphoblastoid Cell Lines," J. Immunol., 156:1841-1847 (1996).
Elleder et al., "Testis—A Novel Storage Site in Human Cholesteryl Ester Storage Disease Autopsy Report of an Adult Case with a Long-Standing Subclinical Course Complicated by Accelerated Atherosclerosis and Liver Carcinoma," Virchows Arch, 436:82-87 (2000).
Elleder et al., Subclinical Course of Cholesteryl Ester Storage Disease in an Adult with Hypercholesterolemia, Accelerated Atherosclerosis, and Liver Cancer, Journal of Hepatology, 32:528-534 (2000).
Written Opinion dated Nov. 5, 2001 from PCT Application No. PCT/US01/03481.
Essa et al., "Wolman Disease: A Review," Curr. Paed. Res., 3:(1):1-12 (1999).
Ezekowitz et al., "Molecular Characterization of the Human Macrophage Mannose Receptor: Demonstration of Multiple Carbohydrate Recognition-Like Domains and Phagocytosis of Yeasts in Cos-1 Cells," J. Exp. Med., 172:1785-1794 (1990).
Ezekowitz et al., "The Structure and Function of Vertebrate Mannose Lectin-Like Proteins," J. Cell. Sci. Suppl., 9:121-133 (1988).
Fadden et al., "Molecular Characterization of the Rat Kupffer Cell Glycoprotein Receptor," Glycobiology, 13(7):529-537 (2003).
Fiete et al., "The macrophage/endothelial cell mannose receptor cDNA encodes a protein that binds oligosaccharides terminating with S04-4-GalNAc,31,4GlcNAcf3 or Man at independent sites," Proc. Natl. Acad. Sci., 94:11256-11261 (1997).
Fitoussi et al., "New Pathogenetic Hypothesis for Wolman Disease: Possible Role of Oxidized Low-Density Lipoproteins in Adrenal Necrosis and Calcification," Biochem, J., 301:267-273 (1994).
Fitzky et al., "7-Dehydrocholesterol-Dependent Proteolysis of HMG-CoA Reductase Suppresses Sterol Biosynthesis in a Mouse Model of Smith-Lemli-Opitz/RSH Syndrome," The Journal of Clinical Investigation, 108(6):905-915 (2001).
Foger et al., "Unusual Presentation of Cholesterol Ester Storage Disease (CESD): Report on New Family," Atherosciersosis, 109:132 Abstract 155 (1994).
Folch et al., "A Simple Method for the Isolation and Purification of Total Lipide from Animal Tissues," J. Bio. Chem, 226:497-509 (1957).

(56) References Cited

OTHER PUBLICATIONS

Friedman et al., "A Comparison of the Pharmacological Properties of Carbohydrate Remodeled Recombinant and Placental-Derived b-Glucocerebrosidase: Implications for Clinical Efficacy in Treatement of Gaucher Disease," Blood, 93(9):2807-2816 (1999).
Fujiyama et al., "A New Mutation (LIPA Tyr22X) of Lysosomal Acid Lipase Gene in a Japanese Patient with Wolman Disease," Human Mutation, 8:377-380 (1996).
Gasche et al., "A Novel Variant of Lysosomal Acid Lipase in Cholesteryl Ester Storage Disease Associated with Mild Phenotype and Improvement on Lovastatin," Journal of Hepatology, 27:744-750 (1997).
Gerlai et al., "Gene-Targeting Studies of Mammalian Behavior: Is it the Mutation or the Background Genotype," Trends Neurosci, 19:177-181 (1996).
Gidiri et al., Letter to the Editor, European Journal of Obstetrics and Gynecology and Reproductive Biology, 142:81-87 (2009).
Ginsberg et al., Suppression of Apolipoprotein B Production during Treatment of Cholesteryl Ester Storage Disease with Lovastatin, J Clin. Invest., 80:1692-1697 (1987).
Glueck et al., "Safety and Efficacy of Treatment of Pediatric Cholesteryl Ester Storage Disease with Lovastatin," Pediatric Research, 32:559-565 (1992).
Goldstein et al., "Role of Lysosomal Acid Lipase in the Metabolism of Plasma Low Density Lipoprotein," The Journal of Biological Chemistry, 250(21):8487-8795, (1975).
Grabowski et al., "Enzyme Therapy for Lysosomal Storage Disease: Principles, Practice and Prospects," Annu. Rev. Genomics Hum. Genet., 4:403-436 (2003).
Groener et al., "Difference in Substrate Specificity Between Human and Mouse Lysosomal Acid Lipase: Low Affinity for cholesteryl Ester in Mouse Lysosomal Acid Lipase," Biochimica et Biophysica Acta, 1487:155-162 (2000).
Opposition against European Patent 1267914, dated Jan. 28, 2010.
Guazzi et al., "Wolman's Disease. Distribution and Significance of the Central Nervous System lesions," Path. Europ., 3:266-277 (1968).
Gunning et al., "Isolation and Characterization of Full-Length cDNA Clones for Human a-, 13-, and y-Actin mRNAs Skeletal but Not Cyoplasmic Actins Have an Amino-Terminal Cysteine that is Subsequently Removed," Molecular and Cellular Biology, 3(5):787-795 (1983).
Guzzetta et al., "Elective Subtotal Splenectomy," Ann. Surg., 211 (1): 34-42 (1990).
Hafner et al., "The Human Primary Hepatocyte Transcriptome Reveals Novel Insights into Atorvastatin and Rosuvastatin Action," Pharmacogenetics and Genomics, 21(11):741-750 (2011).
Hakala et al., "Lysosomal Enzymes are Released from cultured Human macrophages, Hydrolyze LDL in Vitro, and are Present Extracellularly in Human Atherosclerotic Lesions," Arteriosclerosis, Thrombosis, and Vascular Biology, 23:1430-1436, (2003).
Hoeg et al., "Characterization of Neutral and Acid Ester Hydrolase in Wolman's Disease," Biochimica et Biophysica Acta, 711:59-65 (1982).
Hoeg et al., "Cholesteryl Ester Storage Disease and Wolman Disease: Phenotypic Variants of Lysosomal Acid Cholesteryl Ester Hydrolase Deficiency," Am. J. Hum. Genet, 36:1190-1203 (1984).
Holbrook et al., "Tolerization as a Tool for Generating Novel Monoclonal Antibodies," Immunology and Cell Biology, 80:319-322 (2002).
Hollak et al., "Alglucerase Practical Guidance on Appropriate Dosage and Administration in Patients with Gaucher Disease," Biodrugs, 9(1):11-23 (1998).
Hooper et al., "A Novel Missense LIPA Gene Mutation, N98S, in a Patient with Cholesteryl Ester Storage Disease," Clinica Chimica Acta, 398:152-154 (2008).
Hopkins et al., "Human Genetics and Coronary Heart Perspective," Annu. Rev. Nutr., 9:303-45 (1989).

Hua et al., "SREBP-2, A Second Basic-Helix-Leucine Zipper Protein that Stimulates Transcription by Binding to a Sterol Regulatory Element," Proc. Natl. Acad. Sci., 90:11603-11607 (1993).
Heinz et al., "Identification and in Situ Localization of the Insulin-Like Growth Factor-II/Mannose-6-Phosphate (IGF-II/M6P) Receptor in the Rat Gastrointestinal Tract: Comparison with the IGF-1 Receptor," U.S. National Institutes of Health, 129(4):1769-1778 (1991).
Smith et al., "Peptide Sequences Mediating Tropism to Intact Blood-Brain Barrier: An In Vivo Biodistribution Study Using Phage Display," Peptides, 38:172-180 (2012).
Jeyakumar et al., "Storage Solutions: Treating Lysosomal Disorders of the Brain," Nature Reviews Neuroscience, 6:713-725 (2005).
Begley et al., "Lysosomal Storage Diseases and the Blood-Brain Barrier," Current Pharmaceutical Design, 14:1566-1580 (2008).
Bertrand et al., "Transport Characteristics of A Novel Peptide Platform for CNS Therapeutics," J Cell. Molecular Medicine, 14(12):2827-2839 (2010).
Ameis et al., "A 5' Splice-Region Mutation and a Dinucleotide Deletion in the Lysosomal Acid Lipase Gene in Two Patients with Cholesteryl Ester Storage Disease,"Journal of Lipid Research, 36:241-250 (1995).
Abramov et al., "Generalized Xanthomatosis with Calcified Adrenals," Journal of Diseases of Children, pp. 282-286 (1956).
K-T Von Trotha et al., "Influence of Lysosomal Acid Lipase Polymorphisms on Chromosome 10 on the Risk of Alzheimer's Disease and Cholesterol Metabolism," 402:(3):262-266 (2006).
Du et al., "Enzyme Therapy for Lysosomal Acid Lipase Deficiency in the Mouse Model," FASEB J. vol. 10(2):427, Abstract 2409 (1996).
Achord, et al., "Human β-Glucuronidase: In Vivo Clearance and in Vitro Uptake by a Glycoprotein Recognition System an Reticuloendothelial Cells," Cell, 15:269-278 (1978).
Al Essa et al., "Wolman Disease: A Review," Curr Paed Res, 3(1):1-12 (1999).
Aslanidis et al., "Genomic Organization of the Human Lysosomal Acid Lipase Gene (LIPA)," Genomics, 20:329-331 (1994).
Assmann et al., The Online Metabolic & Molecular Bases of Inherited Disease, Chapter 142: 'Acid Lipase Deficiency Wolman Disease and Cholesteryl Ester Storage Disease', Part 16: Lysosomal Disorders, pp. 1-49, Year: 2001, McGraw-Hill Companies, Inc.
Asumendi et al., "Hepatic Sinusoidal Endothelium Heterogeneity with Respect to Mannose Receptor Activity is Interleukin-1 Dependent," 23(6):1521-1529 (1996).
Avert et al., "Cholesteryl Ester Hydrolysis in J774 Macrophages Occurs in the Cytoplasm and Lysosomes," Journal of Lipid Research, 40:405-414 (1999).
Baenziger et al., "Structural Determinants of Concanavalin a Specificity for Oligosaccharides," 254(7):2400-2407(1979).
Barton et al., "Therapeutic Response to Intravenous Infusions of Glucocerebrosidase in a Patient with Gaucher Disease," 87:1913-1916 (1990).
Barton et al., "Replacement Therapy for Inherited Enzyme Deficiency—Macrophage Targeted Glucocerebrosidase for Gaucher's Disease," The New England Journal of Medicine, pp. 1464-1470(1991).
Beaudet et al., "Cholesterol Ester Storage Disease: Clinical, Biochemical, and Pathological Studies," The Journal of Pediatrics, 90(6):910-914 (1977).
Dox, "Effect of Lysosomal Cholesterol Accumulation on Lysosomal and Vacuolar-Atpase Activity," Submitted to the Faculty of the Graduate School of Vanderbilt University, pp. 1-108 (2007).
Beutler et al., "Enzyme Replacement Therapy for Gaucher Disease," Blood, 78(5):1183-1189 (1991).
Biggs et al., "A Manual Colorimetric Assay of Triglycerides in Serum," Clinical Chemistry, 21(3):437-441 (1975).
Bijsterbosch et al., "Quantitative Analysis of the Targeting of Mannose-Terminal Glucocerebrosidase Predominant Uptake by Liver Endothelial Cells," Eur. J Biochem, 237:344-349 (1996).
Bindu et al., "Cholesterol Ester Storage Disease with Unusual Neurological Manifestations in Two Siblings: A Report from South India," Journal of Child Neurology, 22(12):1401-1404 (2007).

(56) References Cited

OTHER PUBLICATIONS

Brady et al., "Modifying Exogenous Glucocerebrosidase for Effective Replacement Therapy in Gaucher Disease," J. Inher. Metab. Dis., 17:510-519 (1994).
Brecher et al., "Effect of Atherosclerosis on Lysosomal Cholesterol Esterase Activity in Rabbit Aorta," Journal of Lipid Research, 18:154-160 (1977).
Briggs et al., "Nuclear Protein that Binds Sterol Regulatory Element of Low Density Lipoprotein Receptor Promoter," 268(19):14490-14496 (1993).
Brown et al., "Multivalent Feedback Regulation of HMG CoA Reductase, a Control Mechanism Coordinating soprenoid Synthesis and Cell Growth," Journal of Lipid Research, 21:505-517 (1980).
Brown et al., "A Receptor-Mediated Pathway for Cholesterol Homeostasis," Science, 232(4746):34-47 (1986).
Brumshtein et al., "Characterization of Gene-Activated Human Acid-β-Glucosidase: Crystal Structure, Glycan Composition, and Internalization into Macrophages," 20(1):24-32 (2010).
Brumshtein et al., "Structural Comparison of Differently Glycosylated Forms of acid-β-Glucosidase, the defective Enzyme in Gaucher Disease," Acta Crystallographica Section D, 62:1458-1465 (2006).
Burke et al., Deficient Activity of Hepatic Acid Lipase in Cholesterol Ester Storage Disease, Science, 176 (4032):309-310 (1972).
Burton et al., "Purification and Properties of Human Placental Acid Lipase," Biochimica et Biophysica Acta, 618:449-460(1980).
Burton et al., "Lysosomal Acid Lipase in Cultivated Fibroblasts:Characterization of Enzyme Activity in Normal and Enzymatically Deficient Cell Lines," Clinica Chimica Acta, 101:25-32 (1980).
Burton et al., "Acid Lipase Cross-Reacting Material in Wolman Disease and Cholesterol Ester Storage Disease," Am J Hum Genet, 33:203-208 (1981).
Byrd et al., "Wolman's Disease: Ultrastructural Evidence of Lipid Accumulation in Central and Peripheral Nervous Systems," Acta Neuropathol, 45:37-42 (1979).
Cagle et al., "Clinicopathologic Conference: Pulmonary Hypertension in an 18-Year-Old girl with Cholesteryl Ester Storage Disease (CESD)," American Journal of Medical Genetrics, 24:711-722(1986).
Chatterjee et al., "Evaluation of Urinary Cells in Acid Cholesteryl Ester Hydrolase Deficiency," Clinical Genetics, 29:360-368 (1986).
Chobanian et al., "Effects of Hypertension and of Antihypertensive Therapy on Atherosclerosis," Suppl. I. Hypertension, 8(4):15-21 (1986).
Chowdhury et al., "A Fourteen Years Old Boy with Cholesterol Ester Storage Disease," J Medicine, 10:146-148 (2009).
Christomanou et al., "Prenatal Monitoring for Wolman's Disease in a Pregnancy at Risk," Clinical Case Reports, 57:440-441 (1981).
Coates et al., "Prenatal Diagnosis of Wolman Disease," American Journal of Medical Genetics, 2:397-407(1978).
Colin et al., "Modification of Pancreatic Lipase Properties by Directed Molecular Evolution," Protein Engineering, Design and Selection, pp. 1-9, (2010) downloaded from peds.oxfordjournals. org.
File History dated Sep. 23, 2010 from European Patent Application No. 01906927.7.
Cortner et al., "Genetic Variation of Lysosomal Acid Lipase," Pediatric Research, 10:927-932 (1976).
Crocker et al., "Wolmans Disease: Three New Patients with a Recently Described Lipidosis," Pediatrics, 35:627-640 (1965).
Cummings et al., Increased Hepatic Secretion of Very-Low-Density Lipoprotein Apolipoprotein B-100 in Cholesteryl Ester Storage Disease, 41(1):111-114 (1995).
D'Agostino et al., "Cholesterol Ester Storage Disease: Clinical, Biochemical, and pathological Studies of Four New Cases," Journal of Pediatric Gastroenterology and Nutrition, 7:446-450 (1988).
Dahl et al., "Hepatosplenomegalic Lipidosis: What Unless Gaucher? Adult Cholesteryl Ester Storage Disease (CESD) with Anemia, Mesenteric Lipodystrophy, Increased Plasma Chitotriosidase Activity and a Homozygous Lysosomal Acid Lipase—1 Exon 8 /Splice Junction Mutation," Journal of Hepatology 31:741-746 (1999).
Daly et al., "Neonatal Gene Transfer Leads to Widespread Correction of Pathology in a Murine Model of Lysosomal Storage Disease," Proc. Natl. Acad, 96:2296-2300 (1999).
Davis, et al., Role of Acid Lipase in Cholesteryl Ester Accumulation During Atherogenesis; Correlation of Enzyme Activity with Acid Lipase-Containing Macrophages in Rabbit and Human Lesions, Atherosclerosis, 55:205-215 (1985).
Wolman, "Involvement of Nervous Tissue in Primary Familial Xanthosmatosis with Adrenal Calcification," Path Europe, 3:259-265 (1968).
Hollak et al., "Alglucerase: Practical Guidance on Appropriate Dosage and Administration in Patients with Gaucher Disease," Biodrugs, 9(1):11-13.
Clarke, "Recombinant Proteins for Genetic Disease," Clin. Genet., 55(6):389-94.
Sheriff et al., Characterization of Lysosomal Acid Lipase by Site-Directed Mutagenesis and Heterologous Expression., J. Biol. Chem., 270:27766-27772 (1995).
*Synageva Biopharma Limited*, plaintiff v. *Children's Hospital Research Foundation, Children's Hospital Foundation, Cincinnati, Ohio and Children's Hospital Medical Center*, defendants, Tribunal de Grande Instance of Paris, Docket No. 12/13131, "Conclusions of Withdrawal of Proceedings".
*Synageva Biopharma Corp., and Synageva Biopharma Limited*, plaintiffs v. *Children's Hospital Research Foundation, Children's Hospital Foundation, Cincinnati, Ohio and Children's Hospital Medical Center*, defendants, Tribunal de Grande Instance of Paris, Docket No. 12/13131, Mar. 26, 2013, "Pleadings No. 1".
*Synageva Biopharma Corp., and Synageva Biopharma Limited*, plaintiffs v. *Children's Hospital Research Foundation, Children's Hospital Foundation, Cincinnati, Ohio and Children's Hospital Medical Center*, defendants, Summons Before the High Court of Paris, Docket No. 12/13131, 2012.
*Synageva Biopharma Limited*, claimant v. *Children's Hospital Research Foundation*, defendant, In the High Court of Justice, Chancery division, Patents Court, Claim No. HC 12 C00211, "Statement of Opposition" (2013).
*Synageva Biopharma Limited*, claimant v. *Children's Hospital Research Foundation*, defendant, In the High Court of Justice, Chancery division, Patents Court, Claim No. HC 12 C00211, "Grounds of Invalidity" (2012).
*Synageva Biopharma Limited*, claimant v. *Children's Hospital Research Foundation*, defendant, In the High Court of Justice, Chancery division, Patents Court, Claim No. HC 12 C00211, "Amended Grounds of Invalidity" (2013).
Schiffmann, "Infusion of α-Galactosidase A Reduces Tissue Globotriaosylceramide Storage in Patients with Fabry Disease," PNAS, 97(1):365-370 (2000).
Ahn et al., "Identification of the Genes Differently Expressed in Human Dendritic Cell Subsets by cDNA Subtraction and Microarray Analysis," Blood, 100:1742-1754 (2002).
Nègre et al., "Acid Lipases and Acid Cholesterol Esterases: Wolman's Disease and Cholesteryl Ester Storage Disease," Path Biol., 36(2):167-181 (1988).
Elleder et al., "Lysosomal Acid Lipase Deficiency. Overview of Czech Patients," Cas Lek Cesk, 13/(23),719-724 (1999).
Martinez et al., "7 Years Experience with Hepatic Transplantation in Children," 6(1 ):7-10 (1993).
Tanaka et al., Acid Lipase Deficiency: Wolman Disease and Cholesteryl Ester Storage Disease, Nippon Rinsho, 53(12):3004-3008 (1995).
Brown et al., "Use of Nile Red Stain in the Detection of Cholesteryl Ester Accumulation in Acid Lipase-Deficient Fibroblasts," Arch. Pathol. Lab. Med., 112:295-297 (1988).
Scriver et al., "The Metabolic and Molecular Bases of Inherited Disease," 7th Ed. V II, McGraw-Hill, New York, pp.2563-2587, 1995.
Mao et al., "Sortase-Mediated Protein Ligation: A New Method of Protein Engineering," J. Am. Chem. Soc. 126, 2670-2671, 2004.
Salvayre et al., "Lipases et Cholesterol Esterases Acides: Maladie De Wolman et Cholesteryl Ester Storage Disease (Polycorie Cholesterolique de L'Adulte)" Path Biol, 36, 167-181, 1988.

(56) References Cited

OTHER PUBLICATIONS

Furbish et al., "Uptake and Distribution of Placental Glucocerebrosidase in Rat Hepatic Cells and Effects of Sequential Deglycosylation," Biochimica et Biophysica Acta, 673 425-434, 1981.
Dalgic "Cholestryl Ester Storage Disease in a Young Child Presenting as isolated Hepatomegaly Treated with Simvastatin," The Turkish Journal of Pediatrics, 48:148-151 (2006).
Tadiboylina "Treatment of Dyslipidemia with Lovastatin and Ezetimibe in an Adolescent with Cholesterol Ester Storage Disease," Lipids in Health and Disease, 4(26): 1-6 (2005).
Bailey "An Overview of Enzyme Replacement Therapy for Lysosomal Storage Diseases" The Online Journal of Issues n Nursing, 13(1):1-4 (2008).
Kim "Successful Management of Difficult Infusion-Associated Reactions in a Young Patient with Mucopolysaccharidosis Type VI Receiving Recombinant Human Arylsulfatase B (Galsulfase [Naglazyme])" Pediatrics, 121(3):714-717 (2008).
Albrecht Dehmel, Opposition Submission 1, pp. 1-56, Jan. 28, 2010 European Patent Register.
Albrecht Dehmel, Opposition Submission 2, pp. 1-17, Apr. 4, 2011, European Patent Register.
Albrecht Dehmel, Opposition Submission 3, pp. 1-8, Aug. 22, 2011, European Patent Register.
*Synageva Biopharma Corp.*, v. *Children's Hospital Research Foundation*, "Grounds of Invalidity of European Patent 1267914," pp. 1-11, Jan. 16, 2012, UK High Court of Justice, Chancery Division, Patents Court.
Akcoren et al., Cholesteryl Ester Storage Disease: Case Report During Childhood, Pediatric and Developmental Pathology, 2:574-576 (1999).
Ameis, "Purification Characterization and Molecular Cloing of Human Hepatic Lysosomal Acid Lipase," Eur. J. Biochem., 219(3):905-914 (1994).
Anderson et al., In Situ Localization of the Genetic Locus Encoding the Lysosomal Acid Lipase/Cholesteryl Esterase (LIPA) Deficient in Wolman Disease to Chromosome 10q23.2-q23.3; Genomics, 15:245-247 (1993).
Anderson et al., "Cloning and Expression of cDNA Encoding Human Lysosomal Acid Lipase/Cholesteryl Ester Hydrolase," J. Biol. Chem., 266:22479-22484 (1991).
Anderson et al., "Lysosomal Acid Lipase Mutations that Determine Phenotype in Wolman and Cholesterol Ester Storage Disease," Mol. Genet. Metab., 68:333-345 (1999).
Anderson et al., "Mutations at the Lysosomal Acid Cholesteryl Ester Hydrolase Gene Locus in Wolman Disease," PNAS, 91:2718-2722 (1994).
Arterburn et al., "Orthotopic Liver Transplantation for Cholesteryl Ester Storage Disease," J. Clin. Gastroenterology, 13:482-485 (1991).
Aslanidis et al., "Genetic and Biochemical Evidence that CESD and Wolman Disease are Distinguished by Residual Lysosomal Acid Lipase Activity," Genomics, 33:85-93 (1996).
Besley et al., "Cholesterol Ester Storage Disease in an Adult Presenting with Sea-Blue Histiocytosis," Clin., Genet., 26:195-203 (1984).
Boldrini et al., "Wolman Disease and Cholesteryl Ester Storage Disease Diagnosed by Histological and Ultrastructural Examination of Intestinal and Liver Biopsy," Path. Res. Practice, 200:231-240 (2004).
Brown et al., "Restoration of a Regulatory Response to Low Density Lipoprotein in Acid Lipase Deficient Human Fibroblast," J. of Biol. Chem, 251:3277-3286 (1976).
Cagle et al., "Clinicopathologic Conference: Pulmonary Hypertension in an 18 Year Old Girl With Cholesteryl Ester Storage Disease (CESD)," Am. J. of Med. Genetics, 24:711-722 (1986).
Chatrath et al., "Cholesterol Ester Storage Disease (CESD) Diagnosed in an Asymptomatic Adult," Dig. Dis. Sci., 54:168-173 (2008).
Coates et al., "Genetic Variation of Human Mononuclear Leukocyte Lysosomal Acid Lipase Activity," Atherosclerosis, 62:11-20 (1986).
Desnick et al., "Advances in the Treatment of Inherited Metabolic Diseases," Chapter 5, pp. 281-369 (1981).
Du et al., "Lysosomal Acid Lipase Deficiency: Correction of Lipid Storage by Adenovirus-Mediated Gene Transfer in Mice," Hum. Gen Ther., 13:1361-1372 (2002).
Du et al., "Enzyme Therapy for Lysosomal Acid Lipase Deficiency in the Mouse Model," Human Mol. Genet., 10:1639-1648 (2001).
Du et al., "Molecular and Enzymatic Analyses of Lysosomal Acid Lipase in Cholesteryl Ester Storage Disease," Mol. Genet. Metab., 64:126-134 (1998).
Du et al., "MRI of Fat Distribution in a Mouse Model of Lysosomal Acid Lipase Deficiency," AJR 184:658-662 (2005).
Du et al., "Targeted Disruption of the Mouse Lysosomal Acid Lipase Gene: Long-Term Survival with Massive Cholesteryl Ester and Triglyceride Storage," Hum. Mol. Genet., 7:1347-1354 (1998).
Du et al., "The Role of Mannosylated Enzyme and the Mannose Receptor in Enzyme Replacement Therapy," Am. J. Hum. Genet., 77:1061-1074 (2005).
Beltroy, E. P. et al., "Lysosomal unesterified cholesterol content correlates with liver cell death in murine Niemann-Pick type C disease," Journal of Lipid Research, 2007, 48(4), 869-881.
Du et al., "Tissue and Cellular Specific Expression of Murine Lysosomal Acid Lipase mRNA and Protein," Journal of Lipid Research, 37:937-949 (1996).
Du et al., "Wolman Disease/Cholesteryl Ester Storage Disease Efficacy of Plant-Produced Human Lysosomal Acid Lipase," J. of Lipid Research, 49:1646-1657 (2008).
Du et al., "Enzyme Therapy for Lysosomal Acid Lipase Deficiency in the Mouse Model," Am. J. Hum. Genetics. 67: (4 Supp 2): 427 (2000).
Grabowski et al., "Enzyme Supplementation for Treatment of Artherosclerosis Using Lysosomal Acid Lipase," Therapy tor Genetic Disorders, The American Journal of Human Genetics, 67(4) (Suppl. 2)(Abstract No. 136) (2000).
Ikeda et al., "Production of Recombinant Human Lysosomal Acid Lipase in Schizosaccharomyces Pombe: Development of a Fed-Batch Fermentation and Purification Process," J. of Bioscience and Bioengineering, 98:366-373 (2004).
Krivit et al., "Woman's Disease: A Review of Treatment with Bone Marrow Transplantation and Consideration for the Future," Bone Marrow Transplantation, 10(Suppl 1):97-101 (1992).
Kuriyama et al., "Lysosomal Acid Lipase Deficiency in Rats: Lipid Analyses and Lipase Activites in Liver and Spleen," J. of Lipid Research, 31:1605-1612 (1992).
Kyriakides et al., "Lipid Accumulations and Acid Lipase Deficiency in Fibroblasts from a Family with Woman's Disease and Their Apparent Correction in Vitro," J. of Lab. Clin. Med., 80:810-816 (1972).
Lian et al., "Lysosomal Acid Lipase Deficiency Causes Respiratory Inflammation and Destruction in the Lung," Am. J. Physio. Lung Cell Mol. Physiol., 286:L801-L807 (2004).
Meyers et al., "The Use of Parenteral Hyperalimentation and Elemental Formula Feeding in the Treatment of Wolman Disease," Nutrition Research, 5:423-429 (1985).
Pagani et al., "New Lysosomal Acid Lipase Gene Mutants Explain the Phynotype of Wolman Disease and Cholestery Ester Storage Disease," J. of Lipid Research, 39:1382-1388 (1998).
Pariyarath et al., "L273S Missense Substitution I Human Lysosomal Acid Lipase Creates A New N-Glycosylation Site," FEBS Letter, 379:79-82 (1996).
Pastores et al., "Enzyme Therapy for the Lysosomal Storage Disorders: Principles, Patents, Practice and Prospects," Expert Opin. Therapeutic Patients. 13(8):1157-1172 (2003).
Pozanansky et al., "Enzyme Replacement Therapy in Fibroblast from a Patient with Cholesteryl Ester Storage Disease," FASEB J., 3:152-156 (1989).
Radar et al., "Expression of Adenoviral Vector Containing the cDNA for Human Lysosomal Acid Lipase in HELA and Wolman Cells," FASEB J. 10(3):Abstract No. 1341 (Annual Meeting of Professional Research Scientists) (1996).
Radar et al., "Gene Therapy for Dyslipidemia: Clinical Prospects," Curr. Atherosc. Rep. 1:58-69 (1999).

(56) References Cited

OTHER PUBLICATIONS

Rothe et al., "Altered Manonuclear Phagocyte Differentiation Associated with Genetic Defects of the Lysosomal Acid Lipase," Atherosclerosis, 130:215-221 (1997).
Sando et al., "Human Lysosomal Acid Lipase/Cholesteryl Ester Hydrolase, Purification and Properties of the Form Secreted by Fibroblasts in Microcarrier Culture," J. of Biological Chem., 260:15186-15193 (1985).
Sando et al., "Recognition and Receptor-Mediated Endocytosis of the Lysosomal Acid Lipase Secreted by Cultured Human Fibroblasts," J. of Lipid Research 23:114-123 (1982).
Stein et al., "Successful Treatment of Wolman Disease by Unrelated Umbilical Cord Blood Transplantation," Europ. J. Pediatrics, 166(7):663-666 (2007).
Wolman et al., "Wolman Disease and It's Treatment," Clin. Pediatr., 34(4):207-212 (1995).
Yoshida et al., "Genetic Lipid Storage Disease with Lysososomal Acid Lipase Deficiency in Rats," Lab. Animal Sci., 40:486-489 (1990).
Zschenker et al., "Characterization of Lysosomal Acid Lipase Mutations in the Signal Peptide and Mature Polypeptide Regions Causing Wolman Disease," Journal of Lipid Research, 42:1033-1040 (2001).
Zschenker et al., "Lysosomal Acid Lipase as a Preproprotein," J. Biochem., 136:65-72 (2004).
Zschenker et a., "Systematic Mutagenesis of Potential Glycosylation Sites of Lysosmal Acid Lipase," J. Biochem., 137:387-394 (2005).
Zhu et al., "Production of Human Monoclonal Antibody in Eggs of Chimeric Chickens," Nature Biotechnology, 23(9):1159-1169 (2005).
International Search Report for PCT/US2011/051096, dated Feb. 2, 2012.
Office Action dated Jan. 18, 2013 from Corresponding U.S. Appl. No. 13/229,558.
GenBank Accession No. AAA59519: Lysosomal Acid Lipase/Cholesteryl Esterase [*Homo sapiens*] 7. (1995).
Skropeta, "The Effect of Individual N-Glycans on Enzyme Activity," Bioorg. Med. Chem., 17:2645-2653.
Pariyarathuparambil, R.: 'Human Lysosomal Acid Lipase: Functional Characterization by Molecular Genetic Analysis and Site-Directed Mutagenesis Studies.' Sissa Digital Library PHD Thesis, [Online] 1995, Retrieved from the Internet: [retrieved on Aug. 5, 2012].
Third Party Pre-issuance Submission in U.S. Appl. No. 13/229,558 dated Dec. 31, 2012. 22 pages.
Lysosomes; http://www.ncbi.nlm.nih.gov/books/NBK9953/, 3 pages downloaded on May 13, 2015.
Tietge et al., "Phenotypic Correction of Lipid Storage and Growth Arrest in Wolman disease Fibroblasts by Gene Transfer of Lysosomal Acid Lipase," Human Gene Therapy, 12(3):279-289 (2001).
Supplementary European Search Report dated Aug. 6, 2014 from Corresponding European Application No. 12746845.
International Preliminary Report of Patentability dated Apr. 30, 2013 from Corresponding International Application No. PCT/US2011/033699.
Carpenter et al., "Peripheral administration of low pH solutions causes activation and sensitisation of convergent dorsal horn neurones in the anaesthetised rat," Neurosci Lett., 298:179-182 (2001).
Thavarungkul et al., "Cholesterol Ester Storage Disease: A Reported Case," J. Med. Assoc. Thai, 78(3): 164-168 (1995).
Pastores, G.M., "Therapeutic approaches for lysosomal storage diseases". Ther Adv Endocrinol Metab (2010), 1(4), 177-188.
Wang, C.S. et al., "Impact of increasing alanine aminotransferase levels within normal range on incident diabetes". Journal of Formosan Medical Association (2012) 111, 201-208.
Quinn, A. et al., "SBC-102, a recombinant enzyme replacement therapy, corrects key abnormalities due to lysosomal acidlipase deficiency", Abstract Submission, American Society of Human Genetics Meeting, Nov. 6, 2010.
Quinn, A. et al., "SBC-102, a recombinant enzyme replacement therapy, corrects key abnormalities due to lysosomal acidlipase deficiency", Poster Presentation, American Society of Human Genetics Meeting, Nov. 6, 2010.
Presentation by Synageva Biopharma Corp., Jefferies Healthcare Conference, "Dedicated to Rare Diseases", Jun. 4, 2012.
Furo Ventures B.V., Opposition Papers submitted in European Patent Application No. EP 11758644.6, pp. 1-162, Nov. 25, 2015.
Summary of Product Characteristics of Kanuma.
Summary of NCT01371825 Clinical Trial, Jul. 19, 2011.
Summary of NCT01307098 Clinical Trial, Mar. 1, 2011.
"Synageva BioPharma Presents Data at the American Society of Human Genetics on SBC-102 for Lysosomal Acid Lipase Deficiency", BusinessWire News, Nov. 4, 2010.
Leavitt, M. et al., "Recombinant Lysosomal Acid Lipase Normalizes Liver Weight, Transaminases And Histopathologcial Abnormalities In An In Vivo Model of Cholesteryl Ester Storage Disease", Journal of Hepatology, 2011, vol. 54, p. S358.
Leavitt, M. et al., "Recombinant Lysosomal Acid Lipase Normalizes Liver Weight, Transaminases And Histopathologcial Abnormalities In An In Vivo Model of Cholesteryl Ester Storage Disease", Poster Presentation, The International Liver Congress, Bedin, Germany, Mar. 30, 2011.
Imanaka et al., "Characterization of Lysosomal Acid Lipase Purified from Rabbit Liver," J. Biochem. 96:1089-1101 (1984).
Shibashi et al., "Hypercholesterolemia in Low Density Lipoprotein Receptor Knockout Mice and its Reversal by Adenovirus-Mediated Gene Delivery," J. Clin Invest., 92:883-893 (1993).
Hatanaka et al., "Human IgA-Binding Peptides Selected from Random Peptide Libraries: Affinity Maturation and Application in IgA Purification," J. Bio. Chem. in Press, M112 389742, pp. 1-12 (2012).
Jirtle et al., "Modulation of Insulin-Like Growth Factor-II/Mannose 6-Phosphate Receptors and Transforming Growth Factor-β1 during Liver Regeneration," The Journal of Biological Chemistry, 266(33):22444-22450 (1991).
Jolly et al., "Lysosomal Storage Diseases of Animals: an Essay in Comparative Pathology," Vet Pathol., 34:527-548 (1997).
Kahana et al., "Primary Familial Xanthomatosis with Adrenal Involvement (Wolman's Disease); Report of a further Case with Nervous System Involvement and pathogenetic Considerations," Pediatrics, 42(1):71-76 (1968).
Kale et al., "End Stage Renal Disease in a Patient with Cholesteryl Ester Storage disease Following Successful Liver Transplantation and Cyclosporine Immunosuppression," Journal of Pediatric Gastroenterology and Nutrition, 20:95-97 (1995).
Kawashiri et al., "Gene Therapy for Lipid Disorders," Curr. Control Trials Cardiovascular Med., 1:120-127 (2000).
Kelly et al., "Characterization of Plasma Lipids and Lipoproteins in Cholesteryl Ester Storage Disease," Biochemical Medicine, 33:29-37 (1985).
Kikuchi et al., "Evaluation of Jejunal Function in Wolman's Disease," Journal of Pediatric Gastroenterology and Nutrition, 12(1): 6569 (1991).
Klima et al., "A Splice Junction Mutation Causes Deletion of a 72-Base Exon from the mRNA for Lysosomal Acid Lipase in a Patient with Cholesteryl Ester Storage Disease," J. Clin Invest, 92:2713-2718 (1993).
Koch et al., "Assignment of LIPA, Associated with Human Acid Lipase Deficiency, to Human Chromosome 10 and Comparative Assignment to Mouse Chromosome 19," Somatic Cell Genetics, 7(3):345-358 (1981).
Kodlitsch et al., "Splice-Site Mutations in Atherosclerosis Candidate Genes Relating Individual Information to Phenotype," Circulation, 100:693-699 (1999).
Kolodny et al., "Current Concepts in Genetics; Lysosomal Storage Disease," The New England Journal of Medicine, 294(22):1217-1220 (1976).
Kostner et al., "Plasma Lipids and Lipoproteins of a Patient with Cholesteryl Ester Storage Disease," J. Inher. Metab. Dis. 8:9-12 (1985).

(56) References Cited

OTHER PUBLICATIONS

Kowel et al., "Low Density Lipoprotein Receptor-Related Protein Mediated Uptake of Cholesteryl Esters Derived from apoprotein E-Enriched Lipoproteins," Proc. Natl. Acad. Sci., 86:5810-5814 (1989).
Krivit et al., "Wolman Disease Successfully Treated by Bone Marrow Transplantation," Bone Marrow Transplantation, 26:567-570 (2000).
Kuriwaki et al., Morphological Characteristics of Lipid Accumulation in Liver-Constituting Cells of Acid Lipase Deficiency Rats (Wolman's Disease Model Rats), Pathology International, 49:291-297 (1999).
Laird et al., "Simplified Mammalian DNA Isolation Procedure," Nucleic Acids Research, 19(15):4293 (1991).
Lake et al., "Wolman's Disease Deficiency of E600-Resistant Acid Esterase Activity with Storage of Lipids in Lysosomes," The Journal of Pediatrics, 76(2):262-266 (1970).
Lake et al., "Histochemical Detection of the Enzyme Deficiency in Blood Films in Wolman's Disease," J. Clin. Path., 24:617-620 (1971).
Lashford et al., "Lysosomal Storage Disorders," Gene Therapy Technologies, Applications and Regulations, John Wiley & Sons, 1999.
Lee et al., "Mannose Receptor-Mediated Regulation of Serum Glycoprotein Homeostasis," Science, 295:1898-1901 (2002).
Lee et al., "Intragenic Deletion as a Novel Type of Mutation in Wolman Disease," Molecular Genetics and Metabolism, 104:703-705 (2011).
Leonova et al., "Proteolytic Processing Patterns of prosaposin in Insect and Mammalian Cells," The Journal of Biological Chemistry, 271(29):17312-17320 (1996).
Leslie et al., "A Mouse Model of Galactose-1-Phosphate Uridyl Transferase Deficiency," Biochemical and Molecular Medicine, 59:7-12 (1996).
Levy et al., "Cholesteryl Ester Storage Disease: Complex Molecular Effects of Chronic Lovastatin Therapy," Journal of Lipid Research, 33:1005-1015 (1992).
Lew et al., "A Mannose Receptor Mediates Mannosyl-Rich glycoprotein-induced Mitogenesis in Bovine Airway Smooth Muscle Cells," J. Clin. Invest., 94:1855-1863 (1994).
Li et al., "Gsh-1, An Orphan Hox Gene, is Required for Normal pituitary Development," The EMBO Journal, 15(4):714-724 (1996).
Lohse et al., "Human Lysosomal Acid Lipase/Cholesteryl Ester Hydrolase and Human Gastric Lipase: Identification of the Catalytically Active Serine, Aspartic Acid, and Histidine Residues," Journal of Lipid Research, 38:892-903 (1997).
Lohse et al., "Human Lysosomal Acid Lipase/Cholesteryl Ester Hydrolase and Human Gastric Lipase:Site-Directed Mutagenesis of Cys227 and Cys236 Results in Substrate-Dependent Reduction of Enzymatic Activity," Journal of Lipid Research,38:1896-1905 (1997).
Lohse et al., "The Acid Lipase Gene Family: Three Enzymes, One Highly Conserved Gene Structure," Journal of Lipid Research, 38:881-891 (1997).
Lohse et al., "Molecular Defects Underlying Wolman Disease Appear to be More Heterogeneous than those Resulting in Cholesteryl Ester Storage Disease," Journal of Lipid Research, 40:221-228 (1999).
Lohse et al., "Compound Heterozygosity for a Wolman Mutation is Frequent Among Patients with Cholesteryl Ester Storage Disease," Journal of Lipid Research, 41:23-31 (2000).
Longhi et al., "Cholesteryl Ester Storage Disease: Risk Factors for Atherosclerosis in a 15-Year-Old Boy," J. Inher. Metab. Dis., 11(2):143-145 (1988).
Lough et al., "Wolman's Disease: An Electron Microscope, Histochemical, and Biochemical Study," Arch. Path, 89:103-110 (1970).
Lowden et al., "Wolman's Disease: A Microscopic and Biochemical Study Showing Accumulation of Ceroid and Esterified Cholesterol," C.M.A. Journal, 102:402-405 (1970).
Lubke et al., "Proteomics of the Lysosome," Biochim Biophys Acta, 1793(4):625-635 (2009).
McCoy et al., "Treatment of Cholesteryl Ester Storage Disease with Combined Cholestyramine and Lovastatin," Ann NY Acad. Sci., pp. 453-454 (1991).
Marsh et al., "Apolipoprotein B Metabolism in Humans: Studies with Stable Isotope-Labeled Amino Acid Precursors," Atherosclerosis, 162:227-244 (2002).
Marshall et al., "Wolman's Disease: A Rare Lipidosis with Adrenal Calcification," Arch. Dis. Childhood, 44:331-341 (1969).
Shome et al., "The Middle-East Connection of Wolman Disease," Saudi. Med. J., 23(5): 597-601 (2002).
Maslen et al., "Occurrence of a mutation associated with Wolman disease in a family with cholesteryl ester storage disease," J Inher. Metab. Dis., 18:620-623 (1995).
Mayatepek et al., "Fatal genetic defect causing Wolman Disease," J. Inher. Metab. Dis., 22:93-94 (1999).
Meikle et al., "Prevalence of Lysosomal Storage Disorders," JAMA, 281(3):249-254 (1999).
Melling et al., "Localised massive tumourous xanthomatosis of the small intestine," Int. J. Colorectal Dis., 22:1401-1404 (2007).
Michels et al., "Pulmonary vascular obstruction associated with cholesteryl ester storage disease," The Journal of Pediatrics, 94:621-622 (1979).
Michels et al., "Cholesteryl Lignocerate Hydrolysis in Adrenoleukodystrophy," Pediat. Res. 14:21-23 (1980).
Mistry et al., "Therapeutic delivery of proteins to macrophages: implications for treatment of Gaucher's disease," The Lancet, 348:1555-1556 (1996).
McPhee et al., "Effects of AAV-2 mediated aspartoacylase gene transfer in the tremor rat model of Canavan disease," Molecular Brain Research, 135:112-121 (2005).
NCBI Reference Sequence: NP_000226, Nov. 3, 2010: Lysosomal acid lipase/cholesteryl ester hydrolase precursor [*Homo sapiens*].
Suzuki, N. et al., "Site-specific N-glycosylation of chicken serum IgG", Glycobiology, vol. 14, No. 3, pp. 275-292, 2004.
Du, "Enzyme therapy for lyposomal acid lipase deficiency in the mouse", Human Molecular Genetics, 2001, vol. 10, Issue 16, 1639-1648 (2001).

* cited by examiner

SEQUENCE LISTING

```
<160> NUMBER OF SEQ ID NOS: 2

<210> SEQ ID NO 1
<211> LENGTH: 378
<212> TYPE: PRT
<213> ORGANISM: Homo sapiens

<400> SEQUENCE: 1

Ser Gly Gly Lys Leu Thr Ala Val Asp Pro Glu Thr Asn Met Asn Val
1               5                   10                  15

Ser Glu Ile Ile Ser Tyr Trp Gly Phe Pro Ser Glu Glu Tyr Leu Val
            20                  25                  30

Glu Thr Glu Asp Gly Tyr Ile Leu Cys Leu Asn Arg Ile Pro His Gly
        35                  40                  45

Arg Lys Asn His Ser Asp Lys Gly Pro Lys Pro Val Val Phe Leu Gln
    50                  55                  60

His Gly Leu Leu Ala Asp Ser Ser Asn Trp Val Thr Asn Leu Ala Asn
65                  70                  75                  80

Ser Ser Leu Gly Phe Ile Leu Ala Asp Ala Gly Phe Asp Val Trp Met
                85                  90                  95

Gly Asn Ser Arg Gly Asn Thr Trp Ser Arg Lys His Lys Thr Leu Ser
            100                 105                 110

Val Ser Gln Asp Glu Phe Trp Ala Phe Ser Tyr Asp Glu Met Ala Lys
        115                 120                 125

Tyr Asp Leu Pro Ala Ser Ile Asn Phe Ile Leu Asn Lys Thr Gly Gln
    130                 135                 140

Glu Gln Val Tyr Tyr Val Gly His Ser Gln Gly Thr Thr Ile Gly Phe
```

```
                145                 150                 155                 160
            Ile Ala Phe Ser Gln Ile Pro Glu Leu Ala Lys Arg Ile Lys Met Phe
                            165                 170                 175

Phe Ala Leu Gly Pro Val Ala Ser Val Ala Phe Cys Thr Ser Pro Met
                            180                 185                 190

Ala Lys Leu Gly Arg Leu Pro Asp His Leu Ile Lys Asp Leu Phe Gly
                            195                 200                 205

Asp Lys Glu Phe Leu Pro Gln Ser Ala Phe Leu Lys Trp Leu Gly Thr
                            210                 215                 220

His Val Cys Thr His Val Ile Leu Lys Glu Leu Cys Gly Asn Leu Cys
            225                 230                 235                 240

Phe Leu Leu Cys Gly Phe Asn Glu Arg Asn Leu Asn Met Ser Arg Val
                            245                 250                 255

Asp Val Tyr Thr Thr His Ser Pro Ala Gly Thr Ser Val Gln Asn Met
                            260                 265                 270

Leu His Trp Ser Gln Ala Val Lys Phe Gln Lys Phe Gln Ala Phe Asp
                            275                 280                 285

Trp Gly Ser Ser Ala Lys Asn Tyr Phe His Tyr Asn Gln Ser Tyr Pro
                290                 295                 300

Pro Thr Tyr Asn Val Lys Asp Met Leu Val Pro Thr Ala Val Trp Ser
            305                 310                 315                 320

Gly Gly His Asp Trp Leu Ala Asp Val Tyr Asp Val Asn Ile Leu Leu
                            325                 330                 335

Thr Gln Ile Thr Asn Leu Val Phe His Glu Ser Ile Pro Glu Trp Glu
                            340                 345                 350

His Leu Asp Phe Ile Trp Gly Leu Asp Ala Pro Trp Arg Leu Tyr Asn
                            355                 360                 365

Lys Ile Ile Asn Leu Met Arg Lys Tyr Gln
                370                 375

<210> SEQ ID NO 2
<211> LENGTH: 21
<212> TYPE: PRT
<213> ORGANISM: Homo sapiens

<400> SEQUENCE: 2

Met Lys Met Arg Phe Leu Gly Leu Val Val Cys Leu Val Leu Trp Thr
1               5                   10                  15

Leu His Ser Glu Gly
            20
```

METHODS FOR TREATING LYSOSOMAL ACID LIPASE DEFICIENCY IN PATIENTS

RELATED APPLICATIONS

This application is a continuation of U.S. patent application Ser. No. 14/851,387, filed Sep. 11, 2015, which is a continuation of U.S. patent application Ser. No. 14/633,240, filed Feb. 27, 2015, which is a continuation of U.S. patent application Ser. No. 14/102,000, filed Dec. 10, 2013, which is a continuation of U.S. patent application Ser. No. 13/229,558, filed Sep. 9, 2011, which claims the benefit of U.S. Provisional Application No. 61/403,011, filed Sep. 9, 2010, U.S. Provisional Application No. 61/456,014, filed Oct. 29, 2010, U.S. Provisional Application No. 61/432,372, filed Jan. 13, 2011, and is a continuation-in-part of PCT/US2011/033699 filed Apr. 23, 2011.

REFERENCE TO SEQUENCE LISTING SUBMITTED ELECTRONICALLY

The content of the electronically submitted sequence listing in ASCII text file (Name SYN080USCON1_ST25.txt; Size 4,096 bytes; and Date of Creation: Sep. 9, 2013) filed with the application is incorporated herein by reference in its entirety.

BACKGROUND OF THE INVENTION

Lysosomal Acid Lipase (LAL) Deficiency is a rare lysosomal storage disease (LSD) characterized by a failure to breakdown cholesteryl esters (CE) and triglycerides (TAG) in lysosomes due to a deficiency of the enzyme. LAL deficiency resembles other lysosomal storage disorders with the accumulation of substrate in a number of tissues and cell types. In LAL deficiency substrate accumulation is most marked in cells of the reticuloendothelial system including Kupffer cells in the liver, histiocytes in the spleen and in the lamina propria of the small intestine. Reticuloendothelial cells express the macrophage mannose/N-acetyl glucosamine receptor (also known as macrophage mannose receptor, MMR, or CD206), which mediates binding, cell uptake and lysosomal internalization of proteins with GlcNAc or mannose terminated N-glycans, and provides a pathway for the potential correction of the enzyme deficiency in these key cell types.

LAL Deficiency is a multi-system disease that most commonly manifests with gastrointestinal, liver and cardiovascular complications and is associated with significant morbidity and mortality. The clinical effects of LAL deficiency are due to a massive accumulation of lipid material in the lysosomes in a number of tissues and a profound disturbance in cholesterol and lipid homeostatic mechanisms, including substantial increases in hepatic cholesterol synthesis. LAL deficiency presents as at least two phenotypes: Wolman Disease (WD) and Cholesteryl Ester Storage Disease (CESD).

Wolman Disease, named after the physician who first described it, is the most aggressive presentation of LAL deficiency. This phenotype is characterized by gastrointestinal and hepatic manifestations including growth failure, malabsorption, steatorrhea, profound weight loss, lymphadenopathy, splenomegaly, and hepatomegaly. Wolman Disease is rapidly progressive and invariably fatal usually within the first year of life. Case report review indicates that survival beyond 12 months of age is extremely rare for patients who present with growth failure due to severe LAL deficiency in the first year of life. In this most aggressive form, growth failure is the predominant clinical feature and is a key contributor to the early mortality. Hepatic involvement as evidenced by liver enlargement and elevation of transaminases is also common in infants.

The diagnosis of Wolman Disease is established through both physical findings and laboratory analyses. Infants are typically hospitalized within the first two months of life due to diarrhea, persistent vomiting, feeding difficulty, stunted growth, and failure to thrive. Physical findings include abdominal distention with hepatomegaly and splenomegaly, and radiographic examination often reveals calcification of the adrenal glands. Laboratory evaluations typically reveal elevated levels of serum transaminases and absent or markedly reduced endogenous LAL enzyme activity. Elevated blood levels of cholesterol and triglycerides are seen in some patients.

Patients with LAL deficiency can also present later in life with predominant liver and cardiovascular involvement, and this is often called Cholesteryl Ester Storage Disease (CESD). In CESD, the liver is severely affected with marked hepatomegaly, hepatocyte necrosis, elevation of transaminases, cirrhosis, and liver fibrosis. Due to increased levels of CE and TAG, the cardiovascular involvement can be characterized by hyperlipidemia. An accumulation of fatty deposits on the artery walls (atherosclerosis) has been reported in some subjects suffering from CESD. The deposits narrow the arterial lumen and can lead to vessel occlusion increasing the risk of significant cardiovascular events including myocardial infarction and strokes. However, not all subjects suffering from LAL deficiency develop atherosclerosis. For example, Wolman Disease patients are overwhelmed with other symptoms associated with the disease, including enlarged liver and spleen, lymphadenopathy, and the malabsorption by the small intestine, but WD is not generally characterized by atherosclerosis (*The Metabolic and Molecular Bases of Inherited Disease* (Scriver, C. R., Beaudet, A. L., Sly, W. S. and Valle D., eds) 7th ed., Volume 2 p. 2570 McGraw-Hill, 1995). Likewise, not all CESD patients exhibit atherosclerosis See, Di Bisceglie et al., *Hepatology* 11: 764-772 (1990), Ameis et al., *J. Lipid Res.* 36: 241-250 (1995). The presentation of CESD is highly variable with some patients going undiagnosed until complications manifest in late adulthood, while others can have liver dysfunction presenting in early childhood. CESD is associated with shortened lifespan and significant ill health. The life expectancy of those with CESD depends on the severity of the associated complications.

Current treatment options for Wolman Disease are very limited. Antibiotics are administered to infants with pyrexia and/or evidence of infection. Steroid replacement therapy for adrenal insufficiency and specialized nutritional support may be prescribed, and while there is no evidence that these interventions prevent death, it is also unclear at present if they have an impact on short term survival. In a series of four patients with LAL deficiency treated with bone marrow transplantation, all four patients died due to complications of the procedure within months of transplantation. Although some success has been described in subsequent case reports, the mortality rate remains high and many patients are not transplanted as they are too ill to survive the pre-transplant conditioning regime. The very small number of reported long-term survivors does indicate that correction of enzyme deficiency in hemopoietic cells alone is sufficient to substantially improve the clinical status in this disease. Typically clinical support is provided through dietary restrictions in an attempt to restrict the build-up of nontransportable and noncatabolizable lipids associated with the acute manifestations of the disease leading to death.

Current treatment options for the CESD phenotype are focused at symptomatic treatment via control of lipid accumulation through diet that excludes foods rich in cholesterol and triglycerides and suppression of cholesterol synthesis and apolipoprotein B production through administration of cholesterol lowering drugs (e.g., statins and cholestyramine). Although some clinical improvement may be seen, the underlying disease manifestations persist and disease progression still occurs.

It has been suggested that enzyme replacement therapy with recombinant LAL may be a viable treatment option for lysosomal acid lipase deficiency and related conditions (see, Meyers et al. (1985) *Nutrition Res.* 5(4):423-442; WO9811206; and Besley (1984) *Clinical Genetics* 26:195-203). Some studies using a mouse model of LAL deficiency have demonstrated correction of some abnormalities of LAL deficient ($LAL^{-/-}$) mice through infusion of high doses (more than 1 milligram per kilogram of body weight) of recombinant human LAL once every 3 days (see, for example, Grabowski US 2007/0264249). These earlier studies to correct the defects within LAL deficient mice suggested that relatively high amounts and frequent dosages of recombinant LAL protein were required in order to correct the underlying phenotypes. It is also important to note that, unlike the $LAL^{-/-}$ rat model described initially by Yoshida and Kuriyama (1990) Laboratory Animal Science, vol 40, p 486-489, the $LAL^{-/-}$ mice model used in the above study does not closely resemble human WD in that the LAL deficient mice do not exhibit growth defects that are seen in human patients.

To date, no exogenous LAL has been administered to humans and there is no effective therapy available for treating LAL deficiencies including WD, CESD, and others. Therefore, there is a dire need for therapies with a minimized frequency of administration in order to improve the quality of life for patients. Further, therapeutically effective doses that restore growth, normalize liver function, increase LAL tissue concentrations, and increase LAL activity in human patients are desirable.

SUMMARY OF THE INVENTION

The present invention is based on the first human clinical cases in which patients were successfully dosed with exogenous LAL. An infant suffering from an otherwise fatal form of LAL Deficiency (Wolman Disease, or early onset LAL Deficiency) was effectively treated by administering exogenous LAL, and safety assessment of LAL enzyme replacement therapy was assessed on a group of human patients suffering from late onset LAL deficiency. The infant with early onset LAL deficiency was administered weekly low doses without eliciting any adverse events or reactions. Dramatic improvements in vital signs and clinical/laboratory measurements for efficacy were observed as early as one to two weeks following the initial administration. After over 4 months of weekly dosing, the treated infant had restored normal growth and exhibited significant improvements in all symptoms related to LAL deficiency including malabsorption, hepatomegaly, and liver function. Late onset adult patients have also been dosed weekly with low amounts of exogenous LAL, with no signs of adverse events. Therefore, the clinical data collected to date show that enzyme replacement therapy using the exogenous LAL of the present invention provides safe and effective treatment for LAL deficiency.

Accordingly, the present invention provides methods of treating diseases or conditions associated with LAL deficiency in human patients by administering an effective amount of exogenous lysosomal acid lipase (LAL). The exogenous LAL can be a recombinant human LAL that has an N-linked glycan structure comprising at least one mannose and/or mannose-6-phosphate. The exogenous LAL is effectively internalized into the lysosome of, e.g., lymphocytes, macrophages, and/or fibroblasts.

In some embodiments, the human patient suffering from LAL deficiency is diagnosed with Wolman disease (WD). In one embodiment, the administration is sufficient to increase growth of a WD patient. In one embodiment, the administration is sufficient to restore normal growth of the WD patient. In other embodiments, the human patient suffering from LAL deficiency is diagnosed with cholesteryl ester storage disease (CESD). The treatment methods according to the present invention can be provided to human patients of any age.

Also provided herein are methods for treating a human patient suffering from LAL deficiency by administering recombinant human LAL to the patient in an effective amount to improve liver function. In some embodiments, the administration is sufficient to normalize liver tests. In one embodiment, the administration is sufficient to decrease serum levels of liver transaminases. For example, the liver transaminases can include serum aspartate transaminase (AST) and/or alanine transaminase (ALT). In one embodiment, the administration is sufficient to minimize hepatomegaly. In one embodiment, the administration is sufficient to decrease liver size of the patient. In one embodiment, the administration is sufficient to decrease serum ferritin levels.

In one embodiment, the administration is sufficient to decrease serum lipid levels, including, for example, cholesteryl ester (CE) and/or triglycerides (TG) levels.

Also provided is a method of increasing LAL activity in a human patient with a LAL deficiency. Such method comprises administering recombinant human LAL to the patient so that the administration results in increased LAL activity, as can be measured, for example, in lymphocytes and/or fibroblasts.

In one embodiment, a method of treating a condition associated with LAL deficiency in a human patient by administering an effective amount of exogenous LAL protein to the patient one time every 5 days to one time every 30 days is described.

In some embodiments, the human patient suffering from LAL deficiency is dosed about 0.1 mg to about 50 mg of exogenous LAL per kilogram of body weight. In one embodiment, the human patient is dosed about 0.1 mg to about 10 mg of exogenous LAL per kilogram of body weight. In one embodiment, the human patient is dosed about 0.1 mg to about 5 mg of exogenous LAL per kilogram of body weight.

In one embodiment, an infusion rate is between about 0.1 mg/kg/hr and about 4 mg/kg/hr.

In some embodiments, the human patient is treated with a second therapeutic. The second therapeutic can include, for example, a cholesterol-reducing drug (e.g., statin or ezetimibe), an antihistamine (e.g., diphenhydramine), or an immunosuppressant.

DETAILED DESCRIPTION OF THE INVENTION

Figure 1A:
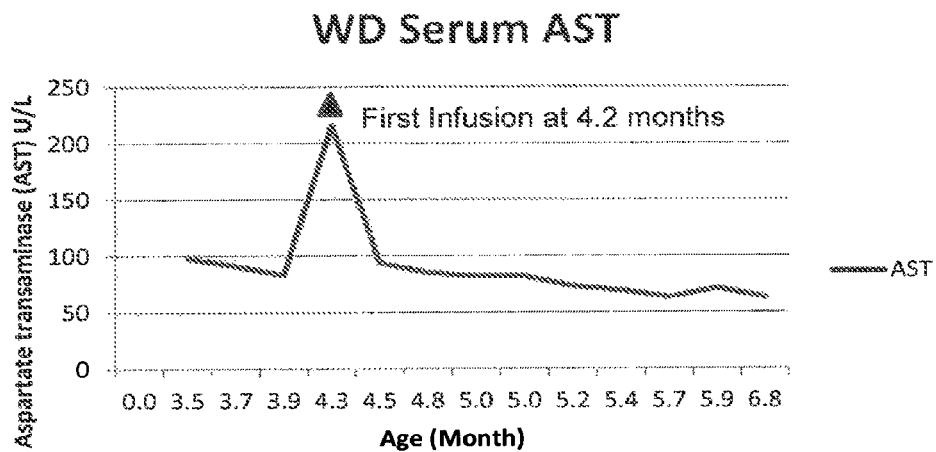
FIG. 1A depicts levels of serum aspartate transaminase (AST) of an infantile male Wolman disease (i.e., early onset LAL deficiency) patient who received weekly dosing of exogenous LAL (SBC-102) (dose: 0.2 mg/kg (initial infusion; week 0); 0.3 mg/kg (week 1); 0.5 mg/kg (week 2); and 1.0 mg/kg (weeks 3-8)).

The present invention provides methods for treating a human suffering from a disease or condition which is responsive to the administration of exogenous lysosomal acid lipase.

Definitions

For convenience, certain terms employed in the specification, examples, and appended claims are set forth herein to illustrate and define the meaning and scope of the various terms used to describe the present invention.

"LAL" as used herein refers to "lysosomal acid lipase," and the two terms are used interchangeably throughout the specification. The LAL can be a human protein, i.e., human lysosomal acid lipase. The term "SBC-102," as used herein, refers to a recombinant human lysosomal acid lipase. LAL is also referred to in the literature as acid cholesteryl ester hydrolase, cholesteryl esterase, Lipase A, LIPA, and sterol esterase.

LAL catalyzes the hydrolysis of cholesterol esters and triglycerides to free cholesterol, glycerol, and tree fatty acids. Thus, "LAL activity" can be measured, for example, by the cleavage of the fluorogenic substrate, 4-methylumbelliferyl oleate (4MUO). Cleavage of 4MUO can be detected, for example, by excitation at about 360 nm and emission at 460 nm of the released flurophore, 4-methylumbelliferone (4MU). Results can be reported in relative fluorescence units (RFU). For example, the amount of substrate cleaved in a 30 minute endpoint assay can be quantified relative to a 4MU standard curve, and one unit (U) of activity can be defined as the amount of enzyme required to cleave 1 micromole of 4MUO per minute at 37° C. Accordingly, functional fragments or variants of LAL include fragments or variants that have LAL activity, e.g., the ability to hydrolyze cholesterol esters and/or triglycerides.

As used herein "exogenous LAL" refers to LAL that is not naturally produced by a patient. For example, exogenous LAL includes recombinant LAL protein that is administered to a patient, LAL protein that is isolated from a person or animal and administered to a patient, and LAL protein that is produced (i.e., expressed) in a patient as a result of administration of LAL-encoding RNA and/or DNA or another treatment that increases expression of endogenous LAL protein.

"Intravenous injection," often medically referred to as IV push or bolus injection, refers to a route of administration in which a syringe is connected to the IV access device and the medication is injected directly, typically rapidly and occasionally up to a period of 15 minutes if it might cause irritation of the vein or a too-rapid effect. Once a medicine has been injected into the fluid stream of the IV tubing, there must be some means of ensuring that it gets from the tubing to the patient. Usually this is accomplished by allowing the fluid stream to flow normally and thereby carry the medicine into the bloodstream. However, in some cases a second fluid injection, sometimes called a "flush," is used following the first injection to facilitate the entering of the medicine into the bloodstream.

"Intravenous infusion" refers to a route of administration in which medication is delivered over an extended period of time. For example, the medication can be delivered to a patient over a period of time between 1 and 8 hours. The medication can also be delivered to a patient over a period of about 1, about 2, about 3, about 4, about 5, about 6, about 7, or about 8 hours. To accomplish an intravenous infusion, an IV gravity drip or an IV pump can be used. IV infusion is typically used when a patient requires medications only at certain times and does not require additional intravenous fluids (e.g., water solutions which can contain sodium, chloride, glucose, or any combination thereof) such as those that restore electrolytes, blood sugar, and water loss.

The term "avian" as used herein refers to any species, subspecies or race of organism of the taxonomic class ayes, such as, but not limited to chicken, turkey, duck, goose, quail, pheasants, parrots, finches, hawks, crows, and ratites including ostrich, emu and cassowary. The term includes the various known strains of *Gallus gallus*, or chickens (for example, White Leghorn, Brown Leghorn, Barred-Rock, Sussex, New Hampshire, Rhode Island, Australorp, Minorca, Amrox, California Gray), as well as strains of turkeys, pheasants, quails, duck, ostriches, and other poultry commonly bred in commercial quantities. It also includes an individual avian organism in all stages of development, including embryonic and fetal stages.

The term "poultry derived" or "avian derived" refers to a composition or substance produced by or obtained from poultry. "Poultry" refers to avians that can be kept as livestock, including but not limited to, chickens, duck, turkey, quail and ratites. For example, "poultry derived" may refer to chicken derived, turkey derived and/or quail derived.

The term "patient" as used herein refers to any person receiving or who has received or is to receive medical care or treatment, e.g, as directed by a medical care provider.

"Therapeutically effective dose" as used herein refers to the dose (e.g., amount and/or interval) of drug required to produce an intended therapeutic response. A therapeutically effective dose refers to a dose that, as compared to a corresponding subject who has not received such a dose, results in improved treatment, healing, prevention, or amelioration of a disease, disorder, or side effect, or a decrease in the rate of the occurrence or advancement of a disease or disorder. The term also includes within its scope, doses effective to enhance physiological functions.

The terms "treat," "treating," and "treatment" refer to methods of alleviating, abating, or ameliorating a disease or symptom, preventing an additional symptom, ameliorating or preventing an underlying cause of a symptom, inhibiting a disease or condition, arresting the development of a disease or condition, relieving a disease or condition, causing regression of a disease or condition, relieving a condition caused by the disease or condition, or stopping a symptom of the disease or condition either prophylactically and/or after the symptom has occurred.

As used herein with reference to a particular dose, "$kg^{-1}$", "per kg", "/kg," and "per kilogram" represent "per kilogram of body weight" of the mammal, and thus the terms can be used interchangeably.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "proteins," "amino acid chains," or any other term used to refer to a chain or chains of two or more amino acids, are included within the definition of "polypeptide," and the teen "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

As used herein, the percent homology between two amino acid sequences or two nucleotide sequences is equivalent to the percent identity between the two sequences. The percent identity between the two sequences is a function of the number of identical positions shared by the sequences (i.e., % homology=# of identical positions/total # of positions ×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)), which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol, Biol.* 48:444-453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated as disclosed herein, as are native or recombinant polypeptides which have been separated, fractionated, or partially or substantially purified by any suitable technique.

Other polypeptides disclosed herein are fragments, derivatives, analogs, or variants of the foregoing polypeptides, and any combination thereof. The terms "fragment," "variant," "derivative" and "analog" when referring to any of the polypeptides disclosed herein include any polypeptides which retain at least some of the activity of the corresponding native polypeptide (e.g., LAL polypeptide fragments, variants, derivatives, and analogs that retain the ability to hydrolyze cholesterol esters and/or triglycerides). Fragments of polypeptides include, for example, proteolytic fragments, as well as deletion fragments. Variants of a polypeptide include fragments as described above, and also polypeptides with altered amino acid sequences due to amino acid substitutions, deletions, or insertions. Variants can occur naturally or be non-naturally occurring. Non-naturally occurring variants can be produced using art-known mutagenesis techniques. Variant polypeptides can comprise conservative or non-conservative amino acid substitutions, deletions, or additions. Derivatives are polypeptides which have been altered so as to exhibit additional features not found on the native polypeptide. Examples include fusion proteins. Variant polypeptides can also be referred to herein as "polypeptide analogs." As used herein, a "derivative" of a subject polypeptide can contain one or more residues chemically derivatized by reaction of a functional side group. Also included as "derivatives" are those peptides which contain one or more naturally occurring amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and/or ornithine can be substituted for lysine.

The terra "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding LAL contained in a vector is considered isolated for the purposes of the present invention. Further examples of an isolated polynucleotide include recombinant polynucleotides maintained in heterologous host cells or purified (partially or substantially) polynucleotides in solution, Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid can be or can include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector can contain a single coding region, or can comprise two or more coding regions. In addition, a vector, polynucleotide, or nucleic acid of the invention can encode heterologous coding regions, either fused or unfused to a nucleic acid encoding a LAL polypeptide or fragment, variant, or derivative thereof. Heterologous coding regions include without limitation specialized elements or motifs, such as a secretory signal peptide or a heterologous functional domain.

A variety of transcription control regions are known to those skilled in the art. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., the MKMRFLGLVVCLVLWTLHSEG (SEQ ID NO:2) signal peptide of human LAL is used, or a functional derivative of that sequence that retains the ability to direct the secretion of the polypeptide that is operably associated with it. Alternatively, a heterologous signal peptide (e.g., a heterologous mammalian or avian signal peptide), or a functional derivative thereof, may be used. For example, the wild-type leader sequence may be substituted with the leader sequence of human tissue plasminogen activator (TPA) or mouse β-glucuronidase.

"Vector" means a polynucleotide comprised of single strand, double strand, circular, or supercoiled DNA or RNA. A typical vector can be comprised of the following elements operatively linked at appropriate distances for allowing functional gene expression: replication origin, promoter, enhancer, 5' mRNA leader sequence, ribosomal binding site, nucleic acid cassette, termination and polyadenylation sites, and selectable marker sequences. One or more of these elements can be omitted in specific applications. The nucleic acid cassette can include a restriction site for insertion of the nucleic acid sequence to be expressed. In a functional vector the nucleic acid cassette contains the nucleic acid sequence to be expressed including translation initiation and termination sites. An intron optionally can be included in the construct, for example, 5" to the coding sequence. A vector is constructed so that the particular coding sequence is located in the vector with the appropriate regulatory sequences, the positioning and orientation of the coding sequence with respect to the control sequences being such that the coding sequence is transcribed under the "control"

of the control or regulatory sequences. Modification of the sequences encoding the particular protein of interest can be desirable to achieve this end. For example, in some cases it can be necessary to modify the sequence so that it can be attached to the control sequences with the appropriate orientation, or to maintain the reading frame. The control sequences and other regulatory sequences can be ligated to the coding sequence prior to insertion into a vector. Alternatively, the coding sequence can be cloned directly into an expression vector which already contains the control sequences and an appropriate restriction site which is in reading frame with and under regulatory control of the control sequences.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, "host cells" refers to cells that harbor vectors constructed using recombinant DNA techniques and encoding at least one heterologous gene.

As used herein the terms "N-glycan," "oligosaccharide," "oligosaccharide structure," "glycosylation pattern," "glycosylation profile," and "glycosylation structure" have essentially the same meaning and each refer to one or more structures which are formed from sugar residues and are attached to glycosylated proteins.

As used herein, the term "pharmaceutical composition" refers to a mixture of a compound described herein with other chemical components, such as carriers, stabilizers, diluents, dispersing agents, suspending agents, thickening agents, and/or excipients.

Patients with Insufficient LAL Activity

Without wishing to limit the invention to the treatment of any particular condition or group of conditions, the invention includes the treatment of lysosomal acid lipase (LAL) deficiencies in patients. As used herein, a patient with a LAL deficiency is any patient that has insufficient LAL activity. The insufficient LAL activity in the patient can, for example, be the result of low RNA levels, low protein levels, or low protein activity. The insufficient LAL activity can result from a mutation in the LAL coding sequence, a LAL regulatory sequence, or in another gene (e.g., a gene that regulates LAL). Insufficient LAL activity can also be the result of environmental factors.

The present invention can be used to treat a wide array of conditions in a subject or patient. Therefore, any condition that can be beneficially treated by exogenous LAL in accordance with the invention is included within the scope of the invention.

One embodiment of the invention focuses on the treatment of lysosomal storages diseases (LSDs) that result from a deficiency in lysosomal acid lipase, specifically Wolman Disease (WD) and Cholesteryl Ester Storage Disease (CESD). Without wishing to limit the invention to any particular theory or mechanism of operation, both WD and CESD can be due to mutations at the LAL locus and result in a massive accumulation of lipid material in the lysosomes in a number of tissues and a profound disturbance in cholesterol and lipid homeostatic mechanisms which can be treated by administration of exogenous LAL in accordance with the methods of the invention. Thus, in one embodiment, the LAL deficiency treated in accordance with the invention is WD. In another embodiment, the LAL deficiency treated in accordance with the invention is CESD. In some embodiments, a diagnosis of WD or CESD is based on genetic analysis (e.g. identification of a functional mutation in a LAL-encoding sequence). In other embodiments, a diagnosis of WD or CESD is based on clinical findings (e.g., physical examination and/or laboratory tests).

In some embodiments, exogenous LAL can be used to treat complications in a variety of conditions such as Non-Alcoholic Fatty Liver Disease (NAFLD) and Non-Alcoholic Steatohepatitis (NASH). NAFLD refers to a disease of the liver which has similar histopathology to liver disease that is due to excessive intake of alcohol. It is characterized by macrovesicularsteatosis which causes enlargement of the liver. NAFLD can progress into NASH which refers to liver disease that is similar to NAFLD with the addition of inflammation and damage to the liver which can lead to fibrosis and cirrhosis.

In some embodiments, exogenous LAL can be used to treat conditions including pancreatitis, for example, chronic pancreatitis and/or acute pancreatitis as well as alcohol induced pancreatic injury such as alcohol induced pancreatitis.

Exogenous LAL produced by any useful method can be used to treat diseases due to alcohol induced cell injury including, but not limited to, those alcohol induced cell injuries that result in accumulation of lipid esters in body tissue such as, but not limited to, liver, spleen, gut, and cardiovascular tissue. According to the invention, malabsorption can also be treated by administering exogenous LAL. Exogenous LAL is also useful for the treatment of patients with Tangier disease and familial hypoalphalipoproteinemia. Tangier disease/familial hypoalphalipo-proteinemia is associated with the accumulation of cholesterol esters in macrophages accompanied by hepatosplenomegaly and/or lymphadenopathy along with low HDL levels which can be treated by the administration of exogenous LAL. For example, without wishing to limit the invention to any particular theory or mechanism of operation, impaired LAL activity can decrease ABCA1 expression and conversely an increased LAL activity obtained by the administration of exogenous LAL to a patient with Tangier disease/familial hypoalphalipoproteinemia will increase ABCA1 expression to overcome the effects of an ABCA1 gene with a reduced functional activity as a result of polymorphism.

In some embodiments, the level of LAL activity in a patient prior to treatment is about 1%, about 2%, about 3%, about 5%, about 10%, about 15%, about 20%, about 30%, about 40%, about 50%, about 60%, about 70%, or about 80% of normal levels of LAL activity. In one embodiment, the level of LAL activity in a patient prior to treatment is about 50% or less of normal levels of LAL activity. In one embodiment, the level of LAL activity in a patient prior to treatment is about 40% or less of normal levels of LAL activity. In some embodiments, the level of LAL activity in a patient prior to treatment is about 30% or less of normal levels of LAL activity. In some embodiments, the level of LAL activity in a patient prior to treatment is about 30% or less of normal levels of LAL activity. In some embodiments, the level of LAL activity in a patient prior to treatment is about 20% or less of normal levels of LAL activity. In some embodiments, the level of LAL activity in a patient prior to treatment is about 10% or less of normal levels of LAL activity. In some embodiments, the level of LAL activity in a patient prior to treatment is about 5% or less of normal levels of LAL activity. In some embodiments, a patient shows no measurable LAL activity prior to treatment.

In some embodiments, the level of LAL activity is measured in cultured fibroblast obtained from a human patient suffering from LAL deficiency. In some embodiments, the level of LAL activity is measured in lymphocytes (e.g., leukocytes) of a human patient suffering from LAL deficiency. The lymphocytes include, but are not limited to, peripheral blood mononuclear cells (PMBC). Methods for the measurement are described, for example, in Burton et al., (1980) *Clinica Chimica Acta* 101: 25-32, and in Anderson et al., (1999) *Mol. Genet. & Metab.*, 66: 333-345, both of which are incorporated herein in their entireties. LAL deficient patients who are to be treated with exogenous LAL can exhibit fibroblast LAL enzymatic activity that is less than about 30, about 20, about 10, about 5, about 4, about 3, about 2 or about 1 pmol/mg/min as measured using triolein as a substrate. LAL deficient patients who are to be treated with exogenous LAL can exhibit leukocyte LAL enzymatic activity that is less than about 30, about 20, about 10, about 5, about 4, about 3, about 2 or about 1 pmol/mg/min as measured by triolein as a substrate. LAL deficient patients who are to be treated with exogenous LAL can exhibit fibroblast LAL enzymatic activity that is less than about 30, about 20, about 10, about 5, about 4, about 3, about 2 or about 1 pmol/mg/min as measured using cholesteryl oleate as a substrate. LAL deficient patients who are to be treated with exogenous LAL can exhibit leukocyte LAL enzymatic activity that is less than about 30, about 20, about 10, about 5, about 4, about 3, about 2 or about 1 pmol/mg/min as measured using cholesteryl oleate as a substrate.

Administration of Exogenous LAL

The invention provides methods of treating human patients with exogenous LAL comprising administering exogenous LAL to the patient, wherein the administration is sufficient to restore growth, to improve liver function, to reduce liver damage, to increase tissue levels of LAL, and/or increase LAL activity in the patient. The invention provides useful and previously uncharacterized frequencies of administration (i.e., dosing schedules) of exogenous LAL to treat conditions stemming from LAL deficiency, including WD and CESD, as well as previously uncharacterized dosing amounts for treatment of these conditions.

The invention provides for a therapeutically effective dose of exogenous LAL to be administered to a patient between one time every 5 days and one time every 30 days for a period of time determined by a practitioner of skill in the art of medical sciences. In one embodiment, the period of time will be the remainder of the patient's life span. In one embodiment, the dosing frequency is between one time every 5 days and one time every 25 days. In one embodiment, the dosing frequency is between one time every 5 days and one time every 21 days. In another embodiment, the dosing frequency is between one time every 7 days and one time every 14 days. The exogenous LAL can be administered one time every 5 days, one time every 6 days, one time every 7 days, one time every 8 days, one time every 9 days, one time every 10 days, one time every 11 days, one time every 12 days, one time every 13 days, or one time every 14 days. In some embodiments, the exogenous LAL is administered about weekly. In other embodiments, the exogenous LAL is administered about bi-weekly. In one embodiment, the dosing frequency is about one time every 30 days.

For the treatment of a condition, generally, the amount of exogenous LAL administered can vary depending on known factors such as age, health, and weight of the recipient, type of concurrent treatment, frequency of treatment, and the like. Usually a dosage of active ingredient can be about 0.01 to about 50 mg per kilogram of body weight. In one embodiment, dosage of exogenous LAL in accordance with the invention is about 0.1 to 0.5 mg per kilogram of body weight. In one embodiment, the dose is about 0.1 mg to about 5.0 mg per kilogram. In one embodiment, the dose is about 0.1 mg to about 5.0 mg per kilogram. In one embodiment the dose is about 0.1, about 0.2, about 0.25, about 0.30, about 0.35, about 0.40, about 0.45, about 0.50 mg per kilogram. In one embodiment, the dose is about 1 mg to about 5 mg per kilogram. In one embodiment, the dose is about 1 mg per kilogram. In one embodiment, the dose is about 3 mg per kilogram. For example, 0.1 mg per kilogram of body weight, 0.2 mg per kilogram of body weight, 0.3 mg per kilogram of body weight, 0.4 mg per kilogram of body weight, 0.5 mg per kilogram of body weight, 1 mg per kilogram of body weight, 2 mg per kilogram of body weight, 3 mg per kilogram of body weight, 4 mg per kilogram of body weight, or 5 mg per kilogram of body weight can be administered. In one embodiment, the dose is about 1 mg to about 20 mg per kilogram of body weight.

The invention also includes other dosages when employing a dosing schedule of the invention. For example in accordance with a dosing schedule of the invention, between about 0.1 mg and about 50 mg per kilogram of body weight is administered to a patient.

In some embodiments, about 0.5 to about 50 mg of exogenous LAL are administered, e.g. to a patient with Wolman disease at the age between 1 month and 24 months. In one embodiment the patient is less than 1 year of age. In another embodiment, the patient is less than 2 years of age. In some embodiments, about 0.1 mg, about 0.2 mg, about 0.3 mg, about 0.4 mg, about 0.5 mg, about 1 mg, about 2 mg, about 3 mg, about 5 mg, about 10 mg, about 15 mg, about 20 mg, about 25 mg, about 30 mg, about 35 mg, about 40 mg, or about 45 mg of exogenous LAL is administered to the patient with Wolman disease. In some embodiments, about 0.5 to about 30 mg, about 0.5 to about 20 mg, about 0.5 to about 10 mg, or about 0.5 to about 5 mg are administered to the patient with Wolman disease. In some embodiments, about 1 to about 30 mg, about 1 to about 20 mg, about 1 to about 10 mg, or about 1 to about 5 mg are administered.

In some embodiments, about 1 mg to about 350 mg of exogenous LAL are administered, e.g. to a patient diagnosed with CESD. Thus, in some embodiments, about 1, 5, 10, 25, 50, 75, 100, 125, 150, 175, 200, 225, 250, 275, 300, 325, or 350 mg of exogenous LAL is administered to the patient with CESD. In some embodiments, about 5 to about 350 mg, about 5 to about 300 mg, about 5 to about 250 mg, or about 5 to about 200 mg are administered to the patient with CESD. In some embodiments, about 10 to about 350 mg, about 10 to about 300, about 10 to about 250, or about 10 to about 200 mg are administered to the patient with CESD.

Combination Treatments

The therapeutic proteins disclosed herein can be used in combination with other therapeutic agents. The invention provides for a pretreatment procedure to minimize or prevent any potential anaphylactic reactions that can be incurred by administration of exogenous LAL in accordance with the invention. In one embodiment, to pretreat a potential anaphylactic reaction, an H-1 receptor antagonist, also known as an antihistamine (e.g., diphenhydramine) is administered to the patient. In one embodiment, the H-1 receptor antagonist is administered in a dose of about 1 mg to about 10 mg per kilogram of body weight. For example, an antihistamine can be administered in a dose of about 5 mg per kilogram. Administration of the antihistamine can be prior to the administration of exogenous LAL in accordance with the invention. In one embodiment, the H-1 receptor antagonist is administered about 10 to about 90 minutes, for example, about 30 to about 60 minutes prior to the administration of exogenous LAL. The H-1 receptor antagonist can be administered using an ambulatory system connected to a vascular access port. In one embodiment, the antihistamine is administered about 90 minutes prior to the administration of exogenous LAL. In one embodiment, the antihistamine is administered between about 10 and about 60 minutes prior to the administration of exogenous LAL. In another embodiment, the antihistamine is administered between about 20 and about 40 minutes prior to administering exogenous LAL. For example, the antihistamine can be administered 20, 25, 30, 35, or 40 minutes prior to the administration of exogenous LAL. In one embodiment, the antihistamine administered is diphenhydramine. Any useful antihistamine can be used. Such antihistamines include, without limitation, clemastine, doxylamine, loratidine, desloratidine, fexofenadine, pheniramine, cetirizine, ebastine, promethazine, chlorpheniramine, levocetirizine, olopatadine, quetiapine, meclizine, dimenhydrinate, embramine, dimethidene, and dexchlorpheniramine.

In one embodiment, the antihistamine is administered in a dose of between about 0.1 mg and about 10 mg per kilogram of body weight. In one embodiment, the antihistamine is administered in a dose between about 1 mg and about 5 mg per kilogram of body weight. For example the dose can be 1 mg, 2 mg, 3 mg, 4 mg, or 5 mg per kilogram of body weight. The antihistamine can be administered by any useful method. In one embodiment, the antihistamine is administered intravenously. In another embodiment, the antihistamine is administered in pharmaceutically acceptable capsules.

In another embodiment, with reference to intravenous infusion, the potential for anaphylactic reactions can be reduced by administering the infusions using a ramp-up protocol. In this context, a ramp-up protocol refers to slowly increasing the rate of the infusion over the course of the infusion in order to desensitize the patient to the infusion of the medication.

Immunosuppresants such as, but not limited to, antihistamines, corticosteroids, sirolimus, voclosporin, ciclosporin, methotrexate, IL-2 receptor directed antibodies, T-cell receptor directed antibodies, TNF-alpha directed antibodies or fusion proteins (e.g., infliximab, etanercept, or adalimumab), CTLA-4-Ig (e.g., abatacept), anti-OX-40 antibodies can also be administered before, during, or after exogenous LAL administration, for example, if an anaphylactic reaction or adverse immune response is expected or experienced by a patient.

The invention also encompasses therapy involving administration of exogenous LAL-containing compositions in combination with one or more cholesterol lowering agents (e.g., HMG-CoA reductase inhibitors). Non-limiting examples of such agents include: atorvastatin (Lipitor® and Torvast®), fluvastatin (Lescol®), lovastatin (Mevacor®, Altocor®, Altoprev®), pitavastatin (Livalo®, Pitava®), pravastatin (Pravachol®, Selektine®, Lipostat®), rosuvastatin (Crestor®), and simvastatin (Zocor®, Lipex).

Effects of Exogenous LAL

The present invention provides for a correction or normalization of disease-related symptoms following treatment with exogenous LAL. The clinical progression (i.e., improvement of the condition) in response to exogenous LAL can be monitored by any useful method or procedure.

In some embodiments, administration of exogenous LAL is sufficient to achieve a Cmax of about 200 ng/mL to about 1,500 ng/mL. In some embodiments, administration of exogenous LAL is sufficient to achieve a Cmax of about 200 ng/mL to about 1,000 ng/mL. In some embodiments, administration of exogenous LAL is sufficient to achieve a Cmax of about 200 ng/mL to about 800 ng/mL. In some embodiments, administration of exogenous LAL is sufficient to achieve a Cmax of about 200 ng/mL, about 300 ng/mL, about 400 ng/mL, about 500 ng/mL, about 600 ng/mL, about 700 ng/mL, about 800 ng/mL, about 900 ng/mL, about 1,000 ng/mL, about 1,250 ng/mL, or about 1,500 ng/mL. In some embodiments, Cmax is reached during infusion.

In some embodiments, administration of exogenous LAL is sufficient to achieve a LAL half-life ($t_{1/2}$) that is less than 40 minutes. In some embodiments, administration of exogenous LAL is sufficient to achieve a LAL half-life ($t_{1/2}$) that is less than 30 minutes. In some embodiments, administration of exogenous LAL is sufficient to achieve a LAL half-life ($t_{1/2}$) that is less than 20 minutes. In some embodiments, administration of exogenous LAL is sufficient to achieve a LAL half-life ($t_{1/2}$) that is less than 15 minutes. In some embodiments, administration of exogenous LAL is sufficient to achieve a LAL half-life ($t_{1/2}$) that is less than 10 minutes. In some embodiments, administration of exogenous LAL is sufficient to achieve a LAL half-life ($t_{1/2}$) of about 6, 7, 8, 9, 10, 11, 12, 13, 14, 15, 16, 17, 18, 19, 20, 25, 30, 35, or 40 minutes.

In some embodiments, exogenous LAL increases LAL activity in a patient. LAL activity can be increased, for example, in liver, spleen, lymph nodes, aorta, peripheral blood leukocytes, and/or skin fibroblasts. In some embodiments, LAL activity is measured in extracts of lymphocytes isolated from blood samples.

Exogenous LAL can increase LAL activity to at least about 1.5, about 2, about 2.5, about 3, about 4, about 5, about 6, about 7, about 8, about 9, about 10, about 15, or about 20 times the activity prior to LAL administration. Exogenous LAL can increase LAL activity to at least about 10, about 11, about 12, about 13, about 14, about 15, about 16, about 17, about 18, about 19, about 20 times the activity prior to LAL administration. LAL activity can be assessed using methods known in the art including, for example, assays using cholesteryl [1-$^{14}$C]oleate, triolein (glycerol tri [1-$^{14}$C] oleate), p-nitropheny myristate or 4-MUO (4-methylumbelliferyl oleate) substrates.

In one embodiment, organ and tissue volume and characterization is employed to determine the improvement of the condition following administration of exogenous LAL in accordance with the invention.

In one embodiment, clinical progression in liver function/injury following administration of exogenous LAL is monitored by the quantification of blood transaminases such as aspartic acid aminotransferase (AST) and/or alanine transaminase (ALT), and/or other biomarkers, such as albumin, alkaline phosphatase, and bilirubin (direct and total), over time.

In one embodiment, clinical progression is monitored using imaging technology. For example, and without limitation, the imaging technology used can be ultrasound, CT scanning, magnetic resonance imaging, and nuclear magnetic resonance spectroscopy.

In some embodiments, administration of exogenous LAL with the doses described herein is sufficient to restore growth and/or increase body weight in human patients. Administration of exogenous LAL can also increase the rate of growth (i.e., body weight increase) in an infant or child patient suffering from early onset LAL deficiency. For example, administration of exogenous LAL can increase the rate of body weight increase by at least about 10%, about 20%, about 30%, about 40%, about 50%, about 60%, about 70%, about 80%, about 90%, about 100%, about 200%, about 300%, about 400%, or about 500% of the growth rate/velocity seen prior to the administration. In some embodiments, administration of exogenous LAL restores normal growth rate in a child patient suffering from early onset LAL deficiency (e.g., Wolman Disease) whose age is between about 1 month and about 24 months. "Normal" in this context refers to normal growth rate for the patient being treated as determined by a practitioner of ordinary skill in the art of medical sciences.

In one embodiment, for example with reference to WD and CESD or other LAL deficiencies, hepatomegaly is reversed significantly with liver size returning to a size of which is within about 1% to about 60% larger than that of normal. "Normal" in this context refers to a liver of normal size for the patient being treated as determined by a practitioner of ordinary skill in the art of medical sciences. In one embodiment, liver size is reduced to between about 1% and about 50% greater than normal. In another embodiment, liver size is reduced to between about 1% and about 40% greater than normal. In one embodiment, liver size is reduced to between about 1% and about 30% greater than normal. In another embodiment, liver size is reduced to between about 1% and about 20% greater than normal. In another embodiment, liver size is reduced to between about 10% and about 20% greater than normal. For example, the liver can be 10%, 11%, 12% 13% 14%, 15%, 16%, 17%, 18%, 19%, or 20% larger than the normal size. In still another embodiment, liver size is reduced to between about 0% and about 10% greater than normal. For example, the liver can be 0%, 1%, 2%, 3%, 4%, 5%, 6%, 7%, 8%, 9%, or 10% larger than the normal size of the liver.

Treatment with exogenous LAL can also improve liver function. Thus, in some embodiments, treatment with exogenous LAL is sufficient to restore normal liver function and/or normalize liver tests. In some embodiments, treatment with exogenous LAL is sufficient to decrease serum levels of liver transaminases, e.g., by at least about 20%, about 30%, about 40%, about 50%, about 60%, about 70%, about 80%, and/or to at least about 90%. In one embodiment, treatment with exogenous LAL is sufficient to decrease serum levels of liver transaminases by at least about 40%. In one embodiment, treatment with exogenous LAL is sufficient to decrease serum levels of liver transaminases by at least about 50%. In one embodiment, treatment with exogenous LAL is sufficient to decrease serum levels of liver transaminases by at least about 60%. In one embodiment, treatment with exogenous LAL is sufficient to decrease serum levels of liver transaminases by at least about 70%. In one embodiment, treatment with exogenous LAL is sufficient to decrease serum levels of liver transaminases by at least about 80%. In one embodiment, treatment with exogenous LAL is sufficient to decrease serum levels of liver transaminases by at least about 90%.

In some embodiments, the liver transaminase is alanine aminotransferase (ALT). In one embodiment, administration of exogenous LAL is sufficient to reduce serum ALT. For example, administration of exogenous LAL can reduce serum ALT, e.g., by at least about 50%, 60%, 70%, 80% or 90%. Serum ALT level can serve an indication of liver injury. Thus, the present invention also contemplates methods of reducing liver injury in a human patient suffering from LAL deficiency by administering an effective amount of exogenous LAL to reduce serum ALT.

In some embodiments, the liver transaminase is serum aspartate transaminase (AST). In one embodiment, administration of exogenous LAL is sufficient to reduce serum AST. For example, administration of exogenous LAL can reduce serum AST, e.g., by at least about 50%, 60%, 70%, 80% or 90%. Serum AST level can serve an indication of liver injury. Accordingly, the present invention also contemplates a method of reducing liver injury in a patient suffering from LAL deficiency by administering an effective amount of exogenous LAL to reduce serum AST.

In some embodiments, treatment with exogenous LAL can decrease serum ferritin levels. Thus, in some embodiments, treatment with exogenous LAL is sufficient to decrease serum ferritin, e.g., by at least about 20%, 30%, 40%, 50%, 60%, 70%, 80%, 90%, or 95% as compared to pretreatment levels. In one embodiment, treatment with exogenous LAL is sufficient to decrease serum levels of ferritin by at least 50%. In yet another embodiment, treatment with exogenous LAL is sufficient to decrease serum levels of ferritin by at least about 60%. In one embodiment, treatment with exogenous LAL is sufficient to decrease serum levels of ferritin by at least about 70%. In one embodiment, treatment with exogenous LAL is sufficient to decrease serum levels of ferritin by at least about 80%. In one embodiment, treatment with exogenous LAL is sufficient to decrease serum levels of ferritin by at least about 90%. In one embodiment, treatment with exogenous LAL is sufficient to decrease serum levels of ferritin by at least about 95%.

In one embodiment, for example, with reference to Wolman Disease and CESD or other LAL deficiencies, splenomegaly is reversed significantly with spleen size returning to a size of which is within about 1% to about 60% larger than that of normal. "Normal" in this context refers to a spleen of normal size for the patient being studied as determined by a practitioner of ordinary skill in the art of medical sciences. In one embodiment, spleen size is reduced to between about 1% and about 50% greater than normal. In another embodiment, spleen size is reduced to between about 1% and about 40% greater than normal. In one embodiment, spleen size is reduced to between about 1% and about 30% greater than normal. In another embodiment, spleen size is reduced to between about 1% and about 20% greater than normal. In another embodiment, spleen size is reduced to between about 10% and about 20% greater than normal. For example, the spleen can be 10%, 11%, 12% 13% 14%, 15%, 16%, 17%, 18%, 19%, or 20% larger than the normal size. In still another embodiment, spleen size is reduced to between about 0% and about 10% greater than normal. For example, the spleen can be 0%, 1%, 2%, 3%, 4%, 5%, 6%, 7%, 8%, 9%, or 10% larger than the normal size of the spleen.

In one embodiment, administration of exogenous LAL is sufficient to decrease lymphadenopathy (i.e., enlarged lymph nodes). Thus, in some embodiments, lymph nodes are reduced to about a size of which is within about 1% to about 60% larger than that of normal. "Normal" in this context refers to lymph nodes of normal size for the patient being studied as determined by a practitioner of ordinary skill in the art of medical sciences. In one embodiment, lymph node size is reduced to about 1% to about 50% greater than normal. In another embodiment, lymph node size is reduced to about 1% to about 40% greater than normal. In one embodiment, lymph node size is reduced to about 1% to about 30% greater than normal. In another embodiment, lymph node size is reduced to about 1% to about 20% greater than normal. In another embodiment, lymph node size is reduced to about 10% to about 20% greater than normal. For example, the lymph nodes can be 10%, 11%, 12% 13% 14%, 15%, 16%, 17%, 18%, 19%, or 20% larger than the normal size. In still another embodiment, lymph node size is reduced to about 0% to about 10% greater than normal. For example, the lymph node can be 0%, 1%, 2%, 3%, 4%, 5%, 6%, 7%, 8%, 9%, or 10% larger than the normal size of the lymph nodes. In another embodiment, lipid analysis is performed to monitor improvement of the condition. For example, lipid analysis can be done to evaluate the therapeutic effect of the exogenous LAL. The lipid analysis can be conducted on a tissue sample of a patient (e.g., a blood sample, liver biopsy sample) by any useful method such as, but not limited to high-performance liquid chromatography, gas chromatography, mass spectroscopy, or thin-layer chromatography, or any combination thereof as deemed appropriate by one skilled in the art. In one embodiment, lipid analyses performed in accordance with the invention, demonstrate the levels of total cholesterol, triglycerides, low-density lipoproteins, high-density lipoproteins and/or cholestryl ester.

In one embodiment, for example, with reference to Wolman Disease and CESD or other LAL deficiencies, lipid analysis of a patient treated in accordance with the invention shows a normalization of lipid concentrations in the liver, spleen, intestine, lymph nodes, and/or aorta as can determined by a practitioner of ordinary skill in the field of medical sciences.

Lipid levels can be assessed using plasma lipid analyses or tissue lipid analysis. In plasma lipid analysis, blood plasma can be collected, and total plasma free cholesterol levels can be measured using, for example colormetric assays with a COD-PAP kit (Wako Chemicals), total plasma triglycerides can be measured using, for example, a Triglycerides/GB kit (Boehringer Mannheim), and/or total plasma cholesterol can be determined using a Cholesterol/HP kit (Boehringer Mannheim). In tissue lipid analysis, lipids can be extracted, for example, from liver, spleen, and/or small intestine samples (e.g., using the Folch method provided in Folch et al. *J. Biol. Chem* 226: 497-505 (1957)). Total tissue cholesterol concentrations can be measured, for example, using O-phthalaldehyde.

In some embodiments, administration of exogenous LAL is sufficient to increase nutrient absorption. In one embodiment, administration of exogenous LAL increases nutrient absorption as measured by levels of serum alpha tocopherol, 250H vitamin D, serum retinol, didehydroretinol, or transthyretin.

In some embodiments, for example with reference to WD and CESD or other LAL deficiencies, administration of exogenous LAL is sufficient to increase serum hemoglobin levels (Hb). In one embodiment, the hemoglobin level is increased at least about 10% or about 20% as compared to that observed prior to administration with exogenous LAL.

In some embodiments, the exogenous LAL can be administered using methods to minimize side effects. For example, the administration of exogenous LAL can minimize immune responses to the exogenous LAL.

LAL and Pharmaceutical Compositions Comprising Exogenous LAL

The present invention encompasses treating any of the LAL deficiency-related conditions described herein and other conditions not previously mentioned, but which would benefit from the treatment. Exogenous LAL employed in accordance with the invention includes recombinant LAL which can be produced in any useful protein expression system including, without limitation, cell culture (e.g., CHO cells, COS cells), bacteria such as *E. coli*, transgenic animals such as mammals and avians (e.g., chickens, duck, and turkey) and in plant systems (e.g., duck weed and tobacco plants). One aspect of the invention relates to recombinant LAL produced in accordance with U.S. Pat. No. 7,524,626, issued Oct. 3, 2006; U.S. patent application Ser. No. 11/973, 853, filed Oct. 10, 2007; Ser. No. 11/978,360, filed Oct. 29, 2007; and Ser. No. 12/319,396, filed Jan. 7, 2009, the disclosures of which are incorporated in their entirety herein by reference. One aspect of the invention relates to recombinant LAL produced as described in Du et al., (2005) *Am. 1 Hum. Genet.* 77: 1061-1074, and Du et al., (2008) *J. Lipid Res.*, 49: 1646-1657, the disclosures of which are incorporated in their entirety herein by reference. In one useful embodiment, the exogenous LAL is produced in the oviduct of a transgenic avian (e.g., a transgenic chicken), for example, according to a method described in PCT/US2011/033699, filed Apr. 23, 2011, which is incorporated by reference herein in its entirety. In some embodiments, the recombinant LAL is produced in an avian cell line. In some embodiments, the recombinant LAL is produced in a mammalian (e.g., a human) cell line.

In one embodiment, exogenous lysosomal acid lipase used in accordance with the invention contains glycans having substantial N-acetylglucosamine (GlcNAc) and mannose terminated N-linked structures. GlcNAc and mannose terminated glycans on exogenous LAL can be specifically recognized and internalized by macrophages and fibroblast. Mannose-6-phosphate (M6P), which can target proteins to the GlcNAc/mannose receptors which are expressed on cells implicated in conditions treatable by exogenous LAL administration, is also typically present on exogenous LAL used in accordance with the invention.

Typically, the exogenous LAL of the invention discussed and disclosed herein is human LAL. In one embodiment, the exogenous LAL has the amino acid sequence provided in Genbank RefSeq NM_000235.2). In one embodiment, the mature exogenous LAL has the amino acid sequence:

```
                                         (SEQ ID NO: 1)
SGGKLTAVDPETNMNVSEIISYWGFPSEEYLVETEDGYILCLNRIPHGRK

NHSDKGPKPVVFLQHGLLADSSNWVTNLANSSLGFILADAGFDVWMGNSR

GNTWSRKHKTLSVSQDEFWAFSYDEMAKYDLPASINFILNKTGQEQVYY

VGHSQGTTIGFIAFSQIPELAKRIKMFFALGPVASVAFCTSPMAKLGRLPD

HLIKDLFGDKEFLPQSAFLKWLGTHVCTHVILKELCGNLCFLLCGFNERN

LNMSRVDVYTTHSPAGTSVQNMLHWSQAVKFQKFQAFDWGSSAKNYF

HYNQSYPPTYNVKDMLVPTAVWSGGHDWLADVYDVNILLTQITNLVFH

ESIPEWEHLDFIWGLDAPWRLYNKIINLMRKYQ
```

In some embodiments, the exogenous LAL comprises amino acids 1-378 of SEQ ID NO:1, amino acids 3-378 of SEQ ID NO:1, amino acids 6-378 of SEQ ID NO:1, or amino acids 7-378 of SEQ ID NO:1. In some embodiments, the exogenous LAL comprises a mixture of at least two polypeptides selected from the group consisting of amino acids 1-378 of SEQ ID NO:1, amino acids 3-378 of SEQ ID NO:1, amino acids 6-378 of SEQ ID NO:1, and amino acids 7-378 of SEQ ID NO:1. In some embodiments, the exogenous LAL comprises a mixture of a polypeptide comprising amino acids 1-378 of SEQ ID NO:1, a polypeptide comprising amino acids 3-378 of SEQ ID NO:1, and a polypeptide comprising amino acids 6-378 of SEQ ID NO:1. In some embodiments, the exogenous LAL comprises a polypeptide that is identical to amino acids 1-378 of SEQ ID NO:1, amino acids 3-378 of SEQ ID NO:1, amino acids 6-378 of SEQ ID NO:1, or amino acids 7-378 of SEQ ID NO:1. In other embodiments, the exogenous LAL comprises a polypeptide that is at least about 70%, about 75%, about 80%, about 85%, about 90%, about 95%, about 96%, about 97%, about 98%, or about 99% identical to amino acids 1-378 of SEQ ID NO:1, amino acids 3-378 of SEQ ID NO:1, amino acids 6-378 of SEQ ID NO:1, or amino acids 7-378 of SEQ ID NO:1. In some embodiments, the exogenous LAL comprises a polypeptide that is a functional fragment of SEQ ID NO:1 or is at least about 70%, about 75%, about 80%, about 85%, about 90%, about 95%, about 96%, about 97%, about 98%, or about 99% identical a functional fragment of SEQ ID NO:1.

In some embodiments the exogenous LAL is a recombinant LAL protein described in PCT/US2011/033699, filed Apr. 23, 2011, which is incorporated by reference herein in its entirety.

It is recognized that amino acid positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity can be adjusted upwards to correct for the conservative nature of the substitution. Means for making this adjustment are well known to those of skill in the art. The scoring of conservative substitutions can be calculated according to, for example, the algorithm of Meyers & Millers, Computer Applic. Biol. Sci. 4:11-17 (1988).

A "comparison window" refers to a segment of contiguous positions, such as between about 25 and about 400 positions, or between about 50 to 200 positions, or between about 100 and 150 positions, over which a sequence may be compared to a reference sequence of the same number of contiguous positions after the two sequences are optimally aligned. Methods of alignment of sequences for comparison are well known in the art. Optimal alignment of sequences for comparison can be conducted, for example, by a local homology algorithm (Smith & Waterman, Adv. Appl. Math. 2:482 (1981), by a global alignment algorithm (Needleman & Wunsch, J. Mol. Biol. 48:443 (1970), by search for similarity methods (Pearson & Lipman, Proc. Natl. Acad. Sci. U.S.A. 85:2444 (1988); Altschul et al., Nucl. Acids Res. 25:3389-402 (1997), by computerized implementations of these algorithms (e.g., GAP, BESTFIT, FASTA, and BLAST in the Wisconsin Genetics Software Package, Genetics Computer Group, 575 Science Dr., Madison, Wis.), typically using the default settings, or by manual alignment and visual inspection (see, e.g., Current Protocols in Molecular Biology, Ausubel et al. (eds.), 1994). For example, BLAST protein searches can be performed using the XBLAST program, score=50, wordlength=3 to obtain amino acid sequences that are more than 80% identical to the amino acid sequence of SEQ ID NO:1 or a fragment thereof.

One example of a useful algorithm implementation is PILEUP. PILEUP creates a multiple sequence alignment from a group of related sequences using progressive pairwise alignments. It can also plot a dendrogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-3 (1989). The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. A series of such pairwise alignments that includes increasingly dissimilar sequences and clusters of sequences at each iteration produces the final alignment.

In some embodiments, exogenous LAL polypeptides of the invention include variants of the wild-type sequences. These variants fall into one or more of three classes: substitutional, insertional, or deletional variants. These variants can be naturally occurring allelic or interspecies variants or they can be prepared by site-specific mutagenesis of nucleotides in the DNA encoding protein. Site-specific mutagenesis can be performed using cassette or PCR mutagenesis or other techniques well known in the art to produce DNA encoding the variant and, thereafter, expressing the DNA in recombinant cell culture. Variant target protein fragments having up to about 100-150 amino acid residues can be prepared by in vitro synthesis using established techniques. Conservative substitution tables providing functionally similar amino acids are well known in the art (Henikoff & Henikoff, Proc. Natl. Acad. Sci. U.S.A. 89:10915-10919 (1992)).

Amino acid substitutions are typically of single residues. Insertions usually will be on the order of from about 1 to about 20 amino acids, although considerably longer insertions can be tolerated. Deletions range from about 1 to about 20 residues, although in some cases, deletions can be much longer. Substitutions, deletions, and insertions or any combinations thereof can be used to arrive at a final derivative.

In some embodiments, the exogenous LAL has a specific activity of at least about 100 U/mg. In some embodiments, the exogenous LAL has a specific activity of at least about 200 U/mg. In some embodiments, the exogenous LAL has a specific activity of at least about 250 U/mg. In some embodiments, the exogenous LAL has a specific activity of about 100 to about 1,000 U/mg. In some embodiments, the exogenous LAL has a specific activity of about 100 to about 500 U/mg. In some embodiments, the exogenous LAL has a specific activity of about 100 to about 350 U/mg. In some embodiments, the exogenous LAL has a specific activity of about 200 to about 350 U/mg. In some embodiments, the exogenous LAL has a specific activity of about 250 to about 350 U/mg. In some embodiments, the exogenous LAL has a specific activity of about 250 U/mg. In some embodiments, the exogenous LAL has a specific activity of about 275 U/mg. In some embodiments, the exogenous LAL has a specific activity of about 300 U/mg. Human LAL has 6 potential sites in its amino acid sequence for N-linked glycosylation: Asn36, Asn72, Asn101, Asn161, Asn273, and Asn321 as set forth in SEQ ID NO:1. In some embodiments, at least 1, 2, 3, 4, or 5 of the 1-linked glycosylation sites are glycosylated. In some embodiments all six glycosylation sites are glycosylated. In some embodiments, Asn36, Asn101, Asn161, Asn273, and Asn321 are glycosylated. In some embodiments, Asn36, Asn101, Asn161, Asn273, and Asn321 are glycosylated, and Asn72 is not glycosylated. In some embodiments, the N-glycan structures comprise bi, tri-, and tetraantennary structures with N-acetylglucosamine (GlcNAc), mannose, and/or mannose-6-phosphate (M6P). In some embodiments, the exogenous LAL comprises M6P-modified N-glycans at Asn101, Asn161, and Asn273. In some embodiments, the exogenous LAL does not comprise O-linked glycans. In some embodiments, the exogenous LAL does not comprise sialic acid. In some embodiments, the exogenous LAL has a glycosylation pattern as described in PCT/US2011/033699, filed Apr. 23, 2011, which is incorporated by reference herein in its entirety.

In some embodiments, the molecular weight of the exogenous LAL is about 55 kD.

In certain embodiments, a subject may be treated with a nucleic acid molecule encoding exogenous LAL, e.g., in a vector. Doses for nucleic acids encoding polypeptides range from about 10 ng to 1 g, 100 ng to 100 mg, 1 μg to 10 mg, or 30-300 μg DNA per patient. Doses for infectious viral vectors vary from 10-100, or more, virions per dose.

In some embodiments of the present invention exogenous LAL is administered in a treatment method that includes: (1) transforming or transfecting an implantable host cell with a nucleic acid, e.g., a vector, that expresses LAL or an active fragment, variant, or derivative thereof; and (2) implanting the transformed host cell into a mammal. In some embodiments of the invention, the implantable host cell is removed from a mammal, temporarily cultured, transformed or transfected with an isolated nucleic acid encoding exogenous LAL, and implanted back into the same mammal from which it was removed. The cell can be, but is not required to be, removed from the same site at which it is implanted. Such embodiments, sometimes known as ex vivo gene therapy, can provide a continuous supply of the exogenous LAL polypeptide, for a limited period of time.

While it is possible for the therapeutic protein provided for in this invention, recombinant LAL, to be administered in raw form, it is preferable to administer the therapeutic protein as part of a pharmaceutical formulation.

The invention thus further provides pharmaceutical formulations comprising avian derived glycosylated therapeutic proteins or a pharmaceutically acceptable derivative thereof together with one or more pharmaceutically acceptable carriers thereof and, optionally, other therapeutic and/or prophylactic ingredients and methods of administering such pharmaceutical formulations. The invention also provides pharmaceutical formulations comprising mammalian derived glycosylated therapeutic proteins or a pharmaceutically acceptable derivative thereof together with one or more pharmaceutically acceptable carriers thereof and, optionally, other therapeutic and/or prophylactic ingredients and methods of administering such pharmaceutical formulations.

The carriers) must be "acceptable" in the sense of being compatible with the other ingredients of the formulation and not deleterious to the recipient thereof. Methods of treating a patient (e.g., quantity of pharmaceutical protein administered, frequency of administration and duration of treatment period) using pharmaceutical compositions of the invention can be determined using standard methodologies known to physicians of skill in the art.

Pharmaceutical formulations include those suitable for oral, rectal, nasal, topical (including buccal and sub-lingual), vaginal or parenteral. The pharmaceutical formulations include those suitable for administration by injection including intramuscular, sub-cutaneous and intravenous administration. The pharmaceutical formulations also include those for administration by inhalation or insufflation. The formulations can, where appropriate, be conveniently presented in discrete dosage units and can be prepared by any of the methods well known in the art of pharmacy. The methods of producing the pharmaceutical formulations typically include the step of bringing the therapeutic proteins into association with liquid carriers or finely divided solid carriers or both and then, if necessary, shaping the product into the desired formulation.

Pharmaceutical formulations suitable for oral administration can conveniently be presented as discrete units such as capsules, cachets or tablets each containing a predetermined amount of the active ingredient; as a powder or granules; as a solution; as a suspension; or as an emulsion. The active ingredient can also be presented as a bolus, electuary or paste. Tablets and capsules for oral administration can contain conventional excipients such as binding agents, fillers, lubricants, disintegrants, or wetting agents. The tablets can be coated according to methods well known in the art. Oral liquid preparations can be in the form of, for example, aqueous or oily suspensions, solutions, emulsions, syrups or elixirs, or can be presented as a dry product for constitution with water or other suitable vehicle before use. Such liquid preparations can contain conventional additives such as suspending agents, emulsifying agents, non-aqueous vehicles (which can include edible oils) or preservatives.

Therapeutic proteins of the invention can also be formulated for parenteral administration (e.g., by injection, for example bolus injection or continuous infusion) and can be presented in unit dose form in ampoules, pre-filled syringes, small volume infusion or in multi-dose containers with an added preservative. The therapeutic proteins can be injected by, for example, subcutaneous injections, intramuscular injections, and intravenous (IV) infusions or injections. In one embodiment, the exogenous LAL is administered intravenously by IV infusion by any useful method. In one example, the exogenous LAL can be administered by intravenous infusion through a peripheral line. In another example, the exogenous LAL can be administered by intravenous infusion through a peripherally inserted central catheter. In another example, the exogenous LAL can be administered by intravenous infusion facilitated by an ambulatory infusion machine attached to a venous vascular access port. In one embodiment, of intravenous infusion, the medication is administered over a period of 1 to 8 hours depending on the amount of medication to be infused and the patient's previous infusion-related reaction history, as determined by a physician skilled in the art. In another embodiment, the exogenous LAL is administered intravenously by IV injection. In another embodiment, the exogenous LAL can be administered via intraperitoneal injection. In still another embodiment, the exogenous LAL is administered via a pharmaceutically acceptable capsule of the therapeutic protein. For example, the capsule can be an enteric-coated gelatin capsule.

In some embodiments, the therapeutic proteins are administered by infusion, and the infusion can occur over an extended time period, for example, 30 minutes to 10 hours. Thus, the infusion can occur, for example, over a period of about 1 hour, about 2 hours, about 3 hours, about 4 hours, or about 5 hours. The infusion can also occur at various rates. Thus, for example, the infusion rate can be about 1 mL per hour to about 20 mL per hour. In some embodiments, the infusion rate is 5 mL to 10 mL per hour. In one embodiment, the infusion rate is 1, 2, 3, 4, 5, 6, 7, 8, 9, 10, 11, 12, 13, 14, 15, 16, 17, 18, 19 or 20 mL per hour. In one embodiment, the infusion rate is 0.1 to 5 mg/kg/hr. In one embodiment, the infusion rate is about 0.1, about 0.2, about 0.3, about 0.5, about 1.0, about 1.5, about 2.0, or about 3 mg/kg/hr, The therapeutic proteins can take such forms as suspensions, solutions, or emulsions in oily or aqueous vehicles, and can contain formulatory agents such as suspending, stabilizing and/or dispersing agents. The therapeutic proteins can be in powder form, obtained by aseptic isolation of sterile solid or by lyophilization from solution, for constitution with a suitable vehicle, e.g., sterile, pyrogen-free water, before use.

For topical administration to the epidermis, the therapeutic proteins can be formulated as ointments, creams or lotions, or as a transdermal patch. Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents or coloring agents.

Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier. Pharmaceutical formulations suitable for rectal administration wherein the carrier is a solid are most preferably represented as unit dose suppositories. Suitable carriers include cocoa butter and other materials commonly used in the art, and the suppositories can be conveniently formed by a mixture of the active compound with the softened or melted carrier(s) followed by chilling and shaping in molds.

Formulations suitable for vaginal administration can be presented as pessaries, tampons, creams, gels, pastes, foams or sprays containing in addition to the active ingredient, such carriers as are known in the art to be appropriate.

For intra-nasal administration the therapeutic proteins of the invention can be used as a liquid spray or dispersible powder or in the form of drops.

Drops can be formulated with an aqueous or non-aqueous base also comprising one or more dispersing agents, solubilizing agents or suspending agents. Liquid sprays are conveniently delivered from pressurized packs.

For administration by inhalation, therapeutic proteins according to the invention can be conveniently delivered from an insufflator, nebulizer or a pressurized pack or other convenient means of delivering an aerosol spray. Pressurized packs can comprise a suitable propellant such as dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount.

For administration by inhalation or insufflation, the therapeutic proteins according to the invention can take the form of a dry powder composition, for example a powder mix of the compound and a suitable powder base such as lactose or starch. The powder composition can be presented in unit dosage form in, for example, capsules or cartridges or, e.g., gelatin or blister packs from which the powder can be administered with the aid of an inhaler or insufflator. When desired, the above described formulations adapted to give sustained release of the active ingredient, can be employed.

The pharmaceutical compositions according to the invention can also contain other active ingredients such as antimicrobial agents, or preservatives.

In some embodiments, the concentration of exogenous LAL in the pharmaceutical composition is about 0.5 to about 10 mg/ml. In some embodiments, the concentration of LAL is about 1 to about 5 mg/mL. In some embodiments, the concentration of LAL is about 1, about 1.5, about 2, about 2.5, about 3, about 3.5, about 4, about 4.5, about 5, about 5.5, about 6, about 6.5, or about 7.5 mg/mL.

In some embodiments, a pharmaceutical composition comprising exogenous LAL further comprises a buffer. Exemplary buffers include acetate, phosphate, citrate and glutamate buffers. Exemplary buffers also include lithium citrate, sodium citrate, potassium citrate, calcium citrate, lithium lactate, sodium lactate, potassium lactate, calcium lactate, lithium phosphate, sodium phosphate, potassium phosphate, calcium phosphate, lithium maleate, sodium maleate, potassium maleate, calcium maleate, lithium tartarate, sodium tartarate, potassium tartarate, calcium tartarate, lithium succinate, sodium succinate, potassium succinate, calcium succinate, lithium acetate, sodium acetate, potassium acetate, calcium acetate, and mixtures thereof. In some embodiments, the buffer is trisodium citrate dihydrate. In some embodiments, the buffer is citric acid monohydrate. In some embodiments, a pharmaceutical composition comprises trisodium citrate dehydrate and citric acid monohydrate.

In some embodiments, a pharmaceutical composition comprising exogenous LAL further comprises a stabilizer. Exemplary stabilizers include albumin, trehalose, sugars, amino acids, polyols, cyclodextrins, salts such as sodium chloride, magnesium chloride, and calcium chloride, lyoprotectants, and mixtures thereof. In some embodiments, a pharmaceutical composition comprises human serum albumin.

In a specific example, recombinant human LAL produced as disclosed herein, is employed in a pharmaceutical formulation wherein each 1 milliliter contains exogenous LAL (e.g., 2 mg LAL), trisodium citrate dehydrate (e.g., 13.7 mg), citric acid monohydrate (e.g., 1.57 mg), and human serum albumin (e.g., 10 mg), and is formulated to an acidic pH such as 5.9±0.1. The present invention encompasses any route of administration which facilitates the uptake of the exogenous LAL into the lysosomes of pertinent organs and tissues.

EXAMPLES

The following specific examples are intended to illustrate the invention and should not be construed as limiting the scope of the claims.

Example 1

Treatment of Early Onset LAL Deficiency (Wolman Disease) by Administration of Recombinant LAL At 15 weeks of age, a male infant was admitted to the hospital because of poor weight gain since birth (birth weight, 3.88 kg). The infant presented with vomiting, feeding problems, poor nutritional status, diarrhea, increasing abdominal distension and anemia. The patient was diagnosed with Wolman Disease.

At the initial physical examination, the patient weighed 5.62 kg placing him below the $5^{th}$ percentile of weight-for-age. Over the next 4 weeks from the initial examination at 15 weeks of age and prior to the initial infusion at 19 weeks of age, the patient failed to gain weight. The estimated growth velocity was calculated to be less than the $1^{st}$ percentile for weight-for-age. The abdomen was markedly distended, with significant hepatomegaly and splenomegaly. Abdominal ultrasound and CT scan confirmed hepatosplenomegaly and bilateral symmetrically enlarged adrenal glands with calcification. The level of serum alanine transaminase (ALT) was elevated at 119 U/L (normal 10-50 U/L), as was the aspartate transaminase (AST) at 216 U/L (normal 10-45 U/L). Before treatment initiation, serum ferritin, a marker of inflammation, was approximately 1,500 µg/L (normal 7-144 µg/L). The patient was persistently anemic prior to treatment with hemoglobin values ranging between 7.2 and 8.3 g/dL.

At 19 weeks of age, once weekly IV infusions of rhLAL (SBC-102) were initiated at an initial dose of 0.2 mg/kg. The patient was pretreated with 1 mg/kg of diphenhydramine approximately 90 minutes prior to the SBC-102 infusion in order to counteract potential infusion reactions. The infusion duration was approximately 4 hours. The infusions were well tolerated, and the patient did not experience any adverse events or infusion related reactions.

Seven days after the initial infusion, the second infusion was administered to the patient. The patient was dosed with 0.3 mg/kg of SBC-102 approximately for 4 hours and tolerated the infusion without exhibiting any signs of adverse events.

Figure 1B:
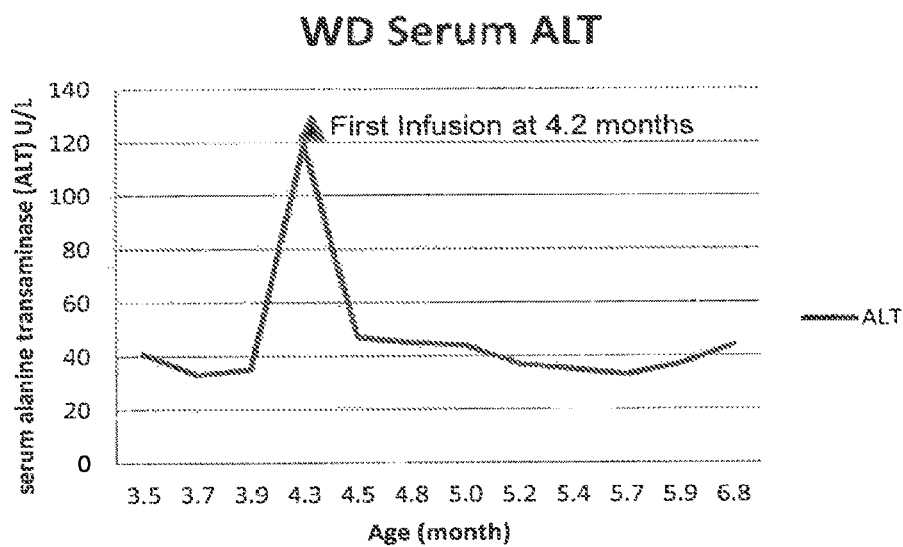
FIG. 1B depicts levels of serum alanine transaminase (ALT) of the same patient. The patient was 4 months and 1 week old at the initial infusion.
Figure 3:
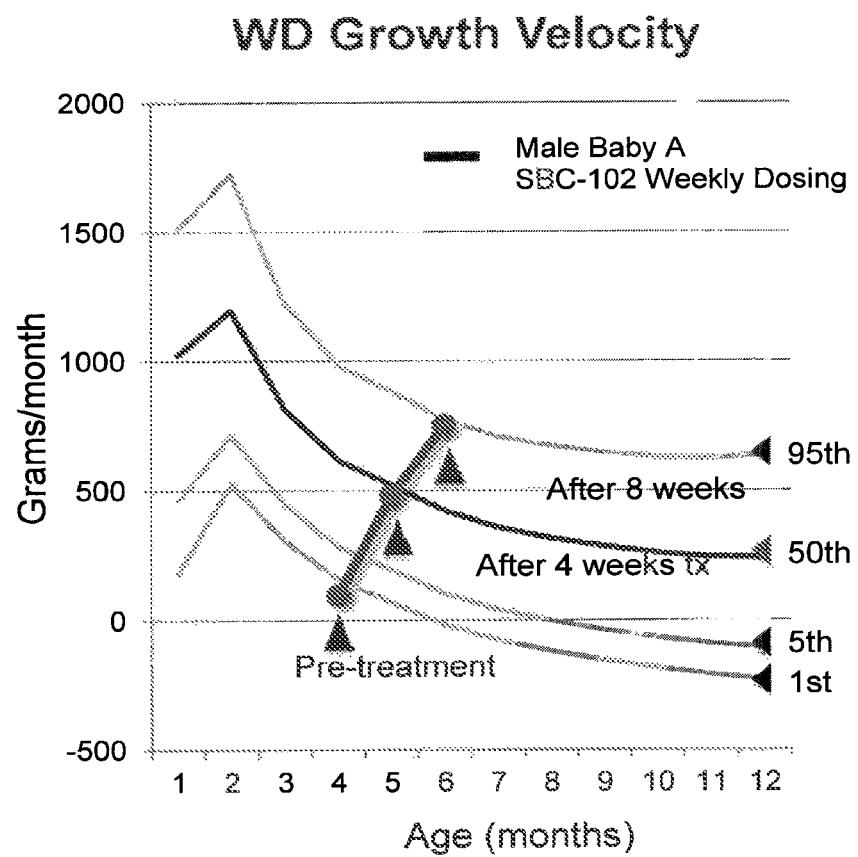
FIG. 3 depicts growth velocity of the Wolman disease patient who received weekly dosing of exogenous LAL (SBC-102) (dose: 0.2 mg/kg (initial infusion; week 0); 0.3 mg/kg (week 1); 0.5 mg/kg (week 2); and 1.0 mg/kg (weeks 3-8)).
Figure 4:
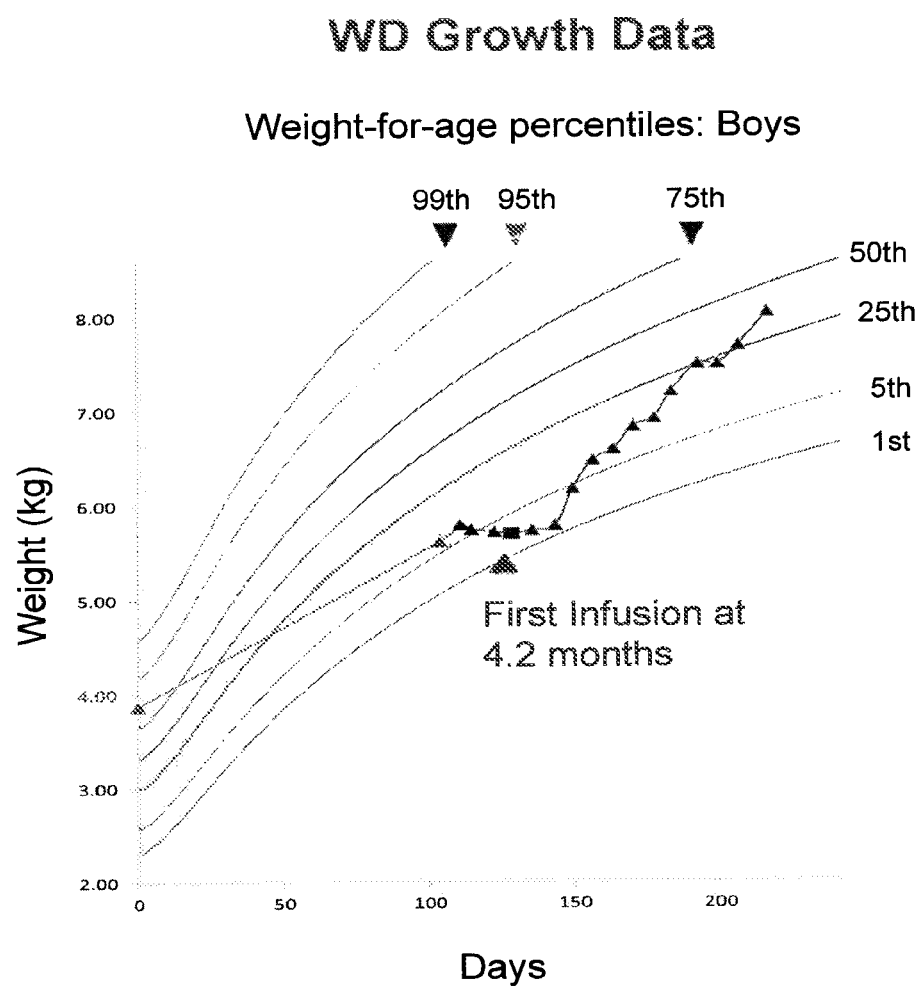
FIG. 4 depicts a growth curve of the Wolman disease patient (kg, weight-for-age percentiles for boys).
Figure 5:
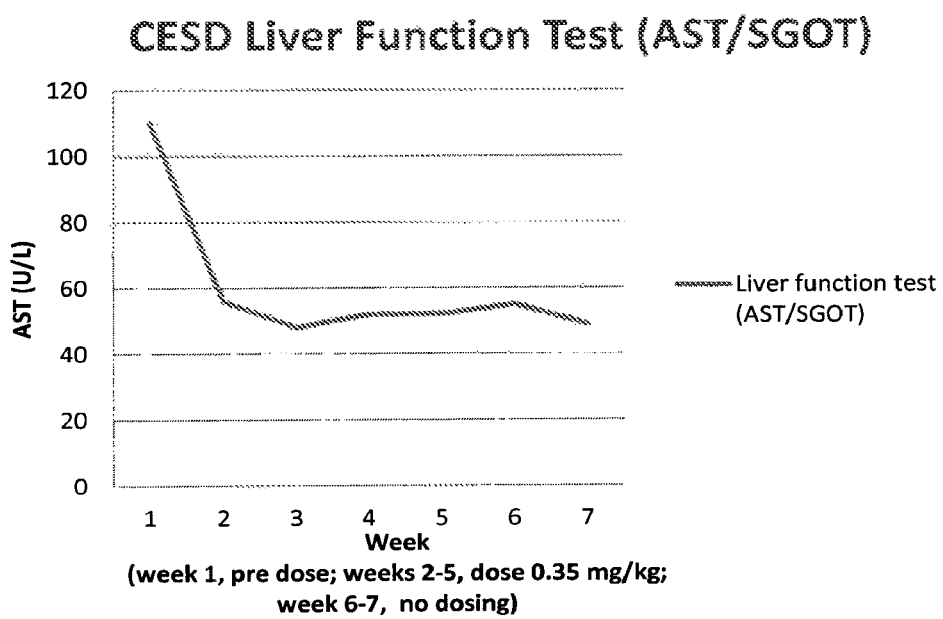
FIG. 5 depicts serum AST levels of a 41-year old white male CESD patient who received weekly doses of 0.35 mg/kg of exogenous LAL.
Figure 6:
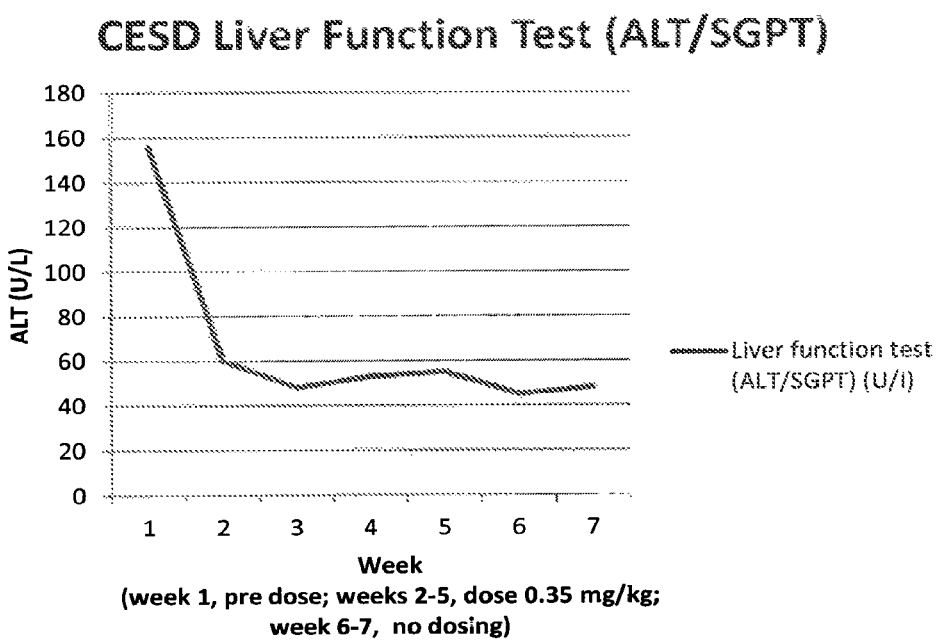
FIG. 6 depicts serum ALT levels of a 41-year old white male CESD patient who received weekly doses of 0.35 mg/kg of exogenous LAL.
Figure 7:
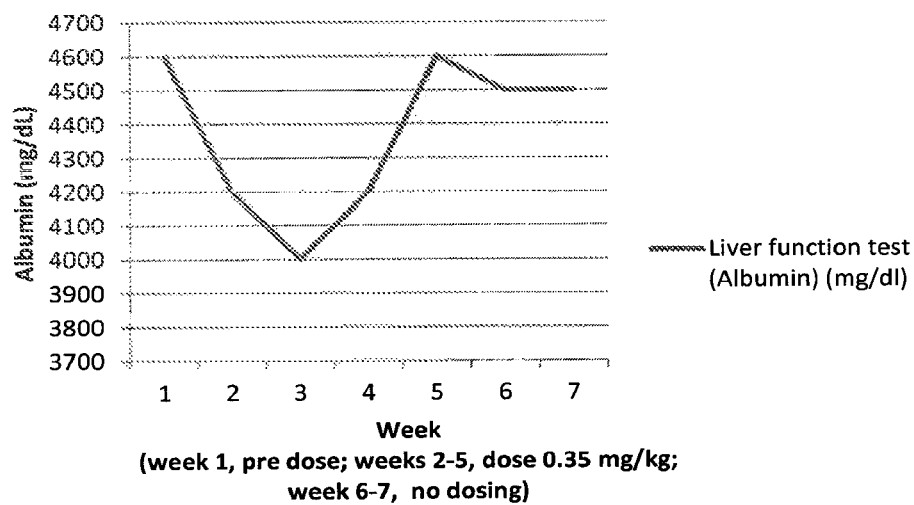
FIG. 7 depicts serum albumin levels of a 41-year old white male CESD patient who received weekly doses of 0.35 mg/kg of exogenous LAL.
Figure 8:
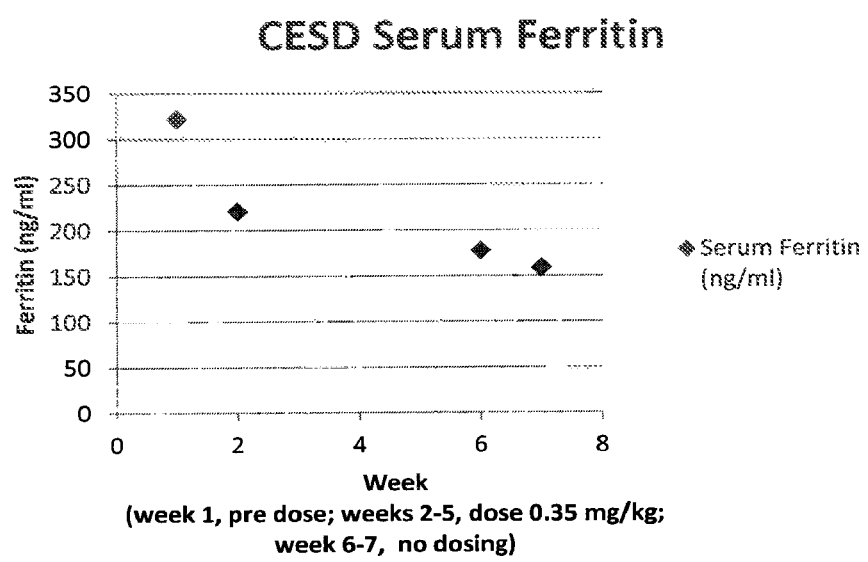
FIG. 8 depicts serum ferritin levels of a 41-year old white male CESD patient who received weekly doses of 0.35 mg/kg of exogenous LAL.

Within two weeks of starting treatment, the patient exhibited significant improvement in general well-being, including increased alertness and responsiveness. The diarrhea and vomiting were stabilized. The patient began to gain weight and exhibited marked reduction in serum transaminases (e.g., AST and ALT), essentially to normal levels (FIGS. 1A and 1B). Growth velocity of the patient rapidly normalized (FIGS. 3 and 4). Abdominal distension decreased, corresponding with a reduction in abdominal girth. Liver function tests showed continued improvements (FIGS. 1A and 1B).

Figure 2:
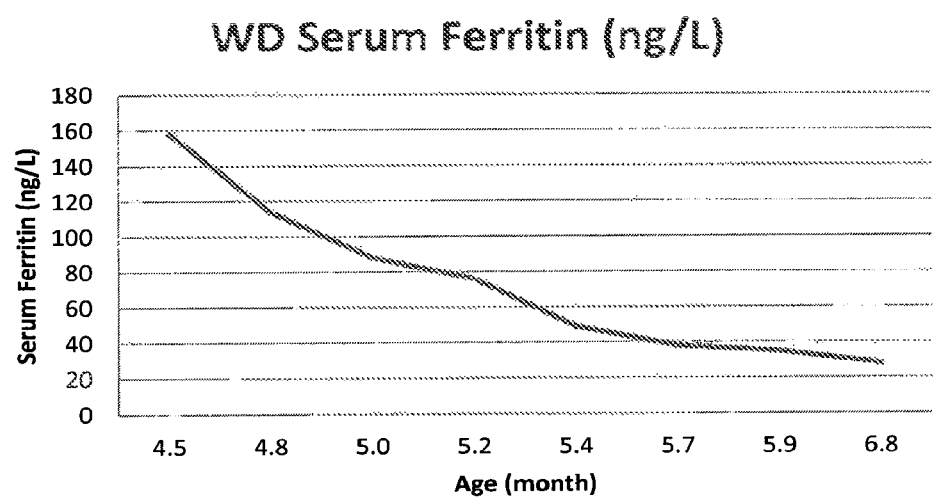
FIG. 2 depicts levels of serum ferritin of the Wolman disease patient who received weekly dosing of exogenous LAL (SBC-102) (dose: 0.2 mg/kg (initial infusion; week 0); 0.3 mg/kg (week 1); 0.5 mg/kg (week 2); and 1.0 mg/kg (weeks 3-8)). The patient was 4 months and 1 week old at the initial infusion. The serum ferritin levels are shown from the week 1 following the initial dosing at week 0.

At the third visit, the patient received SBC-102 at 0.5 mg/kg. The infusions continued to be well tolerated. Clinical status showed continued improvement, with a weight gain of 150 g in 7 days, and a 1.5 cm increase in arm circumference since the treatment initiation (FIGS. 3 and 4). Liver tests were stable, hemoglobin levels increased (10-11 g/dL), and ferritin levels continued to decrease (FIG. 2). Alkaline phosphatase was at the low range of normal prior to treatment 137 U/L (normal 110-300 U/L) and increased with treatment (204 U/L). This effect with SBC-102 administration was consistent with observations made in the preclinical disease model.

Beginning with the fourth infusion, the patient began receiving a weekly dose of 1.0 mg/kg. Two months following the treatment initiation, the patient's growth was substantially improved with an estimated growth velocity close to the $95^{th}$ percentile. This increase in growth resulted in a gain of 1.25 kg, or 2.79 pounds in 63 days with a weight of 7.21 kg, placing him at the 30 percentile of weight-for-age (FIGS. 3 and 4). Both AST and ALT levels decreased rapidly following the first infusion.

Three months into the treatment, the AST and ALT were normal. In addition to improvements in liver function, a marked reduction in ferritin was also observed (FIG. 2).

Over the course of 4 months of treatment, the patient's GI symptoms resolved and the patient's nutritional status was excellent. The patient continued to gain weight (FIGS. 3 and 4) and demonstrated physical signs of a normal, healthy infant. The patient continued to tolerate the infusions without exhibiting any infusion reactions or other side effects. The patient received the $21^{st}$ dose at 1.0 mg/kg as an out-patient.

Example 2

Study Design for Early Onset LAL Deficiency

SBC-102, an rhLAL produced in transgenic *Gallus*, is administered by weekly IV infusion. The study is designed to evaluate the safety, tolerability and efficacy of two dose regimens of SBC-102 administered by weekly IV infusions. As such, the main outcome variables in this study determine safety and tolerability of SBC-102 in children with growth failure due to LAL Deficiency, and include: vital signs and physical examination findings; clinical laboratory tests; anti-drug antibodies tests; and use of concomitant medications. Considering that a growth failure is a universal clinical feature of LAL Deficiency/Wolman phenotype, a successful therapy for this disorder should be able to address the growth failure seen in children affected by LAL Deficiency. Parameters directly related to the child's growth and nutritional status are evaluated as secondary or exploratory objectives: e.g., incremental growth velocity for weight; weight gain; and rate of linear growth. This study also investigates the effects of SBC-102 on pharmacodynamic biomarkers; liver and spleen size; lymphadenopathy; hemoglobin and platelets; laboratory assessments of liver function and nutrition; abdominal girth, mid-upper arm circumference, and head circumference. This study also describes the preliminary pharmacokinetics of SBC-102 in children with growth failure due to LAL Deficiency, including plasma Cmax and estimated clearance.

TABLE 1

Schedule of Assessments: Screening through Week 24

| Assessments | Initial Diagnosis Pre-infusion | Week 1 ±2 days | Week 2 ±2 days | Week 3 ±2 days | Week 4 ±2 days | Week 6 ±2 days | Week 8 ±2 days | Week 10 ±2 days | Week 12 ±2 days | Week 14 ±2 days | Week 16 ±2 days | Week 18 ±2 days | Week 20 ±2 days | Week 22 ±2 days | Week 24 ±2 days |
|---|---|---|---|---|---|---|---|---|---|---|---|---|---|---|---|
| Informed Consent | X | | | | | | | | | | | | | | |
| Inclusion/Exclusion | X | | | | | | | | | | | | | | |
| Medical History | X | | | | | | | | | | | | | | |
| Sample for molecular genetic analysis | | | | | | | | | | | | | | | |
| Dried Blood Spot | | | | | | | | | | | | | | | |
| Health-Related | X | | | | | | | | | | $X$ | | | | X |
| 12-lead ECG [1] | X | | | | | | | | | | $X^P$ | | | | |
| Physical Examination [2] | X | | | $X^P$ | | | | | | | $X^P$ | | | | |
| Pregnancy Test [3] | X | | | $X^P$ | | | | | | | $X^P$ | | $X^P$ | $X^P$ | $X^P$ |
| Clinical Laboratory | X | | | $X^P$ | | | | | | | $X^P$ | | | | $X^P$ |
| Liver, Lipid, and | X | $X^P$ | | $X^P$ | | | | | | | $X^P$ | | | | $X^P$ |
| Acute Phase [4] | X | $X^P$ | | $X^P$ | | | | | | | $X^P$ | | | | $X^P$ |
| Anti SBC 102 | X | | | $X^P$ | | $X^P$ | | | $X^P$ | | $X^P$ | | $X^P$ | | $X^P$ |

TABLE 1-continued

Schedule of Assessments: Screening through Week 24

| Assessments | Initial Diagnosis Pre-infusion | Week 1 ±2 days | Week 2 ±2 days | Week 3 ±2 days | Week 4 ±2 days | Week 6 ±2 days | Week 8 ±2 days | Week 10 ±2 days | Week 12 ±2 days | Week 14 ±2 days | Week 16 ±2 days | Week 18 ±2 days | Week 20 ±2 days | Week 22 ±2 days | Week 24 ±2 days |
|---|---|---|---|---|---|---|---|---|---|---|---|---|---|---|---|
| Serum and Urine Exploratory Biomarker Collection | X | | | | $X^P$ | | $X^P$ | | $X^P$ | | $X^P$ | | $X^P$ | | $X^P$ |
| Abdominal MRI/MRS[6] | X | | | | | | | | | X | | | | | |
| Vital Signs[7] | | X | X | X | X | X | X | X | X | $X^9$ | X | X | X | X | X |
| SBC-102 Infusion | | X | X | X | X | X | X | X | X | $X^{10}$ | X | X | X | X | X |
| Adverse Events | | | | | | | Continuous | | | | | | | | |
| Concomitant Meds/Therapies | | | | | | | Continuous | | | | | | | | |

[P]Pre-infusion
[1] Age appropriate HRQOL.
[2]Physical examination will include measurement of weight (height only at screening), assessment of liver and spleen size, lymphadenopathy and arterial disease.

Subjects are enrolled in two sequential cohorts of equal size (4 subjects each). Dosing is staggered within each cohort and between cohorts, with dosing commencing with the first subject in the lower-dose cohort (Cohort 1; starting dose 0.35 mg·kg$^{-1}$). Dosing of additional subjects in Cohort 1 and initiation of dosing in the higher-dose cohort (Cohort 2; starting dose 1 mg·kg$^{-1}$) is based on acceptable safety and tolerability in preceding subjects.

Cohort 1

The first four subjects enrolled in the study constitute Cohort 1. The first subject in this cohort receives a single dose of SBC-102 0.35 mg·kg$^{-1}$ and, if approved for continued dosing based on a safety review through at least 24 hours post-dose, the subject then receives a second dose of SBC-102 0.35 mg·kg$^{-1}$ one week later. After the subject receives the second dose of SBC-102, all available safety data are reviewed, at which point the acceptability is decided with respect to whether to escalate the dose for the first subject to 1 mg·kg$^{-1}$ and to initiate dosing of the other subjects in Cohort 1. Dosing of the other 3 subjects from Cohort 1 proceeds in a similar manner. If the safety review does not warrant a subject's dose escalation from 0.35 mg·kg$^{-1}$ to 1 mg·kg$^{-1}$, but deems it safe for the subject to continue treatment at the starting dose, the subject may continue to receive a dose of 0.35 mg·kg$^{-1}$. If any subject in Cohort 1 exhibits a suboptimal response to treatment after receiving at least 4 doses of SBC-102 1 mg·kg$^{-1}$, a further dose escalation to 3 mg·kg$^{-1}$ is considered.

Cohort 2

Commencement of dosing in Cohort 2 occurs after Cohort 1 is fully enrolled and the safety reviewed for at least 2 subjects who received 2 or more doses of 1 mg·kg$^{-1}$ SBC-102 in Cohort 1. The last 4 subjects entering the study are enrolled and dosed in Cohort 2. The first subject in this cohort receives a single dose of SBC-102 1 mg·kg$^{-1}$ and, if approved for continued dosing based on safety review through at least 24 hours post-dose, the subject then receives a second dose of SBC-102 1 mg·kg$^{-1}$ one week later. After the subject receives the second dose of SBC-102, all available safety data are to be reviewed on the acceptability of the following: escalating the dose for the first subject to 3 mg·kg$^{-1}$ and initiating dosing of the other subjects in Cohort 2. Dosing of the other 3 subjects from Cohort 2 is performed in a similar manner, with a safety review. If the safety reviewer does not approve a subject's dose escalation from 1 mg·k$^{-1}$ to 3 mg·kg$^{-1}$, but deems it safe for the subject to continue treatment at the starting dose, the subject may continue to receive a dose of 1 mg·kg$^1$. If the starting dose of 1 mg·kg$^{-1}$ is not well-tolerated by a subject, a reduced dose of 0.35 mg·kg$^{-1}$ may be considered.

The study consists of approximately 22 scheduled visits: Visit 1 (screening), Visit 2 (baseline assessment, start of study drug) through Visit 21 (weekly administration of study drug), Visit 22 (end of study follow-up). Given the severity and life threatening nature of early onset growth failure due to LAL Deficiency, it is likely that these subjects will be hospitalized.

The target population for the study is male and female children with growth failure due to LAL Deficiency. A subject is eligible to participate in this study if the following criteria are met: (1) subject's parent or legal guardian understands the full nature and purpose of the study, including possible risks and side effects, and provides written informed consent/permission prior to any study procedures being performed; (2) male or female child with a documented decreased LAL activity relative to the normal range of the lab performing the assay or documented result of molecular genetic testing confirming a diagnosis of LAL Deficiency; and (3) growth failure with onset before 6 months of age.

Safety

The primary safety endpoints includes the incidence of adverse events (AEs) and infusion related reactions (IRRs); changes from baseline in vital signs (blood pressure, heart rate, respiratory rate, and temperature), physical examination findings, and clinical laboratory tests (CBC/hematology, serum chemistry, and urinalysis); use of concomitant medications/therapies; and characterization of anti-SBC-102 antibodies (ADAs) including seroconversion rate, time to seroconversion, median and peak immunoglobulin G (IgG) ADA titer, and time to peak IgG ADA titer.

Efficacy

Efficacy endpoints include: (1) change and/or percent change from baseline in liver and spleen size (by ultrasound) and liver and spleen volume and fat content (by magnetic resonance imaging [MRI]); and (2) change from baseline in serum transaminases, serum lipids (total cholesterol, triglycerides, high density lipoprotein [HDL], and low density lipoprotein [LDL]), hemoglobin and platelet count. Growth parameters, including change from baseline in percentile and z-scores, are also evaluated for subjects ≤18 years of age. These growth parameters are based on Centers for Disease Control (CDC) growth charts and include weight-for-age (WFA), weight-for-length (WFL), length-for-age (LFA), and head circumference-for-age (HCFA) in subjects <30 months of age and WFA, stature-for-age (SFA; Note: stature refers to a subject's height.), and weight-for-stature (WFS) in subjects ≥36 months to 18 years of age, as well as the corresponding growth status indicators of underweight, wasting, and stunting in all subjects.

Example 3

Physical Assessments of Early Onset LAL Deficiency Patients

Patients who are clinically stable enough to tolerate general anesthesia should be considered for central line placement for long-term vascular access. In subjects receiving general anesthesia and/or sedation for other procedures, a baseline abdominal magnetic resonance imaging (MRI) scan is considered. In the event of new procedures requiring general anesthesia and/or sedation, a follow-up MRI is considered if it is no earlier than 3 months after the first infusion. Anthropometrics (weight, height, abdominal circumference, mid-upper arm circumference, and head circumference) are measured. A general physical examination is performed. A complete physical examination is conducted. The examination includes an assessment of the subject's general appearance, skin, head, eyes, ears, nose, and throat, heart, lungs, abdomen, extremities/joints, and neurological status. Every physical examination also includes the following:

Liver size: A clinical assessment of liver size (palpable/non palpable and centimeters below costal margin), regularity (smooth/nodular) and sensitivity (tender/non tender) is made.

Spleen size: A clinical assessment of spleen size (palpable/non palpable and centimeters below costal margin), regularity (smooth/nodular) and sensitivity (tender/non-tender) is made.

Lymphadenopathy: An assessment of the size, location, and character of any palpable lymph nodes is made. Areas to be examined include: cephalic (occipital, preauricular, postauricular, submental, submandibular), cervical, clavicular, axillary, and inguinal. Any enlarged nodes are characterized as tender or non-tender.

Photograph: A digital image of the subject in supine position (full length and abdominal close up) is taken.

Hepatic/Spleen Ultrasound and MRI

Abdominal ultrasonography can be performed to measure the liver and spleen size. Abdominal MRI can provide a better quantification of liver and spleen volume, and be considered at baseline and at a visit at least 3 months after the first infusion.

Vital Signs

Vital signs include pulse rate, respiratory rate, systolic and diastolic blood pressure and core body temperature (rectal or oral). Assessment of pulse rate and blood pressure are taken after the subject has been in a supine position. Vital signs are measured at all study visits. On dosing days, vital signs are recorded pre-infusion, every 15 minutes (±10) during infusion and for 2 hours after the infusion and then every 30 minutes (±15) between 2 and 4 hours after the infusion is completed.

Example 4

Laboratory Assessments

The following laboratory assessments are performed as diagnostic tests and efficacy:
  1) CBC/Hematology: White blood cell count, red blood cell count hemoglobin, hematocrit, mean corpuscular volume (MCV), mean corpuscular hemoglobin (MCH), mean corpuscular hemoglobin concentration (MCHC), platelet count, neutrophil, lymphocytes, monocytes, eosinophils, basophils, peripheral smear for examination of cell morphology
  2) Chemistry Panel: Glucose, urea nitrogen, creatinine, sodium, potassium, chloride, calcium (total and ionized), magnesium, inorganic phosphorus, total protein, lactate dehydrogenase
  3) Liver Function Tests: AST/serum glutamic oxaloacetic transaminase (SGOT), ALT/serum glutamic pyruvic transaminase (SGPT), alkaline phosphatase, gamma-glutamyl transpeptidase (GGTP), albumin, bilirubin (direct, total)
  4) Anti-drug Antibody: Anti-SBC-102 antibody
  5) Urinalysis: pH, glucose, ketones, blood, protein, nitrite
  6) Coagulation Studies: leukocytes (microscopic examination can be done if blood, nitrite and/or leukocytes are abnormal)
  7) Laboratory Nutrition Assessments: serum alpha tocopherol:cholesterol ratio, 25OH vitamin D, serum retinol, didehydroretinol, transthyretin, serum ferritin.
  8) Lipid Panel: Total cholesterol, triglyceride, HDL, LDL
  9) Genetic Profile DNA sequences, including both the protein coding sequence and sequences that regulate gene transcription, messenger ribonucleic acid (mRNA) stability and the efficiency of protein translation that can be identified include:
  1. Lysosomal Acid Lipase (LIPA gene)
  2. Genes coding for other proteins involved in lipid biology that may contribute to and/or modify the disease phenotype of LAL Deficiency, e.g. ABCA1
  3. Genes that may modify susceptibility to any SBC-102
  10) Pharmacokinetic Assessments To reduce risk of iatrogenic anemia, PK sampling may be limited. In order of importance, samples are collected to derive the following parameters: 1) Cmax and 2) estimation of CL. Sampling for measurement of SBC-102 serum levels on Day 0 (Dose 1) and Day 105 (Lose 16) are collected. In all subjects, samples are collected pre-dose (within 30 minutes of dosing); at 90(±5) minutes after the start of the infusion; and at 110(±5) minutes after the start of the infusion. All PK samples, at time points that coincide with a vital sign assessment, are to be taken before cuff inflation for BP assessment on the non-infusion arm. PK samples at other time points are taken at least 5 minutes after cuff deflation.

Example 5

Dose Preparation and Infusion

SBC-102 is provided in single dose 10 mL glass vials as a clear liquid. The solution (total 10.5 mL including 5% overfill) has a concentration of 2 mg·mL$^{-1}$. All SBC-102 vials were stored at a controlled temperature of 2-8° C. Vials are frozen and protected from light during storage. The syringe containing SBC-102 diluted in 0.9% saline was prepared immediately before infusion. When the syringe of SBC-102 had been prepared in advance, the diluted solution was labeled and used within 4 hours of preparations.

The patient's weight, as recorded prior to dosing on the morning of the infusion and rounded to the nearest 0.1 kg, was used for calculating SBC-102 volume for each infusion. The total infusion volumes used in the study are based on the dosing regimen shown in Table 2.

TABLE 2

| Dose | Infusion Volume |
|---|---|
| 0.35 mg/kg | 10 mL |
| 1 mg/kg | 10 mL |
| 3 mg/kg | 20 mL |

Dose preparation and administration should be performed using sterile, non-pyrogenic disposable materials including, but not restricted to syringes, needles, transfer tubing and stopcocks.

The infusion rate on the flow-regulating device should be set to administer the total volume over approximately 120 minutes as shown in Table 3.

TABLE 3

| Dose | Infusion Rate per Hour | Infusion Rate per minute | Infusion Rate per kilogram per hour |
|---|---|---|---|
| 0.35 mg/kg | 5 mL | 0.083 mL | 0.175 mg/kg/hr |
| 1 mg/kg | 5 mL | 0.083 mL | 0.5 mg/kg/hr |
| 3 mg/kg | 10 mL | 0.167 mL | 1.5 mg/kg/hr |

Example 6

Adverse Events (AEs)

In subjects who experience AEs or infusion related reactions (IRR) with clinically significant cardiovascular, respiratory, or other effects, the infusion should be discontinued and the subject must be treated for an anaphylactic reaction according to institutional guidelines for severe infusion reaction management in children less than 2 years of age. This may include intravenous antihistamines, corticosteroids, and epinephrine, if necessary. For related biological products, the majority of delayed IRRs occur more than 24 hours after the infusion. Symptoms include arthralgia, myalgia, influenza-like symptoms, headache, tiredness, and rash or urticaria. Delayed reactions can be treated with analgesics or antihistamines as clinically indicated. IRRs are classified as either acute (occurring within 24 hours of the start of the infusion) or delayed (occurring between 1 and 6 days after the infusion). Medications and equipment for the treatment of hypersensitivity reactions must be available for immediate use in case of unexpected, severe hypersensitivity reactions. These supplies include, but are not restricted to, oxygen, acetaminophen, antihistamines (e.g., diphenhydramine, parenteral and PO), corticosteroids, epinephrine and cardiopulmonary resuscitation devices. In similar biological products, most acute IRRs occur within 24 hours of the infusion (Cerezyme®, VPRIV®, Fabrazyme® prescribing information). Signs of a possible acute IRR can be categorized as: mild to moderate IRRs: hyperemia, flushing, fever and/or chills, nausea, pruritus, urticaria, gastro-intestinal symptoms (vomiting, diarrhea, abdominal cramping). Mild reactions are defined as self limiting, spontaneously resolving reactions after temporary cessation or a reduction in the infusion rate. Moderate reactions are defined as reactions which do not resolve with simple measures, require extended observation and therapy discontinuation. Severe IRR entails chest pain, dyspnea, wheezing, stridor, hypotension or hypertension, respiratory arrest, apnea, dyspnea, bradycardia or tachycardia. If any of the above signs and symptoms are observed during the infusion and the subject remains hemodynamically stable, the infusion rate can be slowed (reduced to half the rate being given at the onset of the event, e.g. from 10 mL·hr$^{-1}$ to 5 mL·hr$^{-1}$) and the infusion time extended. Once the event has resolved, the infusion should continue for a minimum of 30 minutes at the reduced rate before the rate is increased to 75% of the original rate on the infusion schedule. If the subject continues to show signs of hypersensitivity, an IM or slow IV dose of an antihistamine may be administered according to institutional guidelines for infusion reaction management in children less than 2 years of age.

Example 7

Administration of rhLAL to a Human Patient with Late Onset LAL Deficiency

The primary objective of the study is to evaluate the safety and tolerability of SBC-102 in patients with liver dysfunction due to late onset LAL Deficiency (vital signs, physical examination, clinical laboratory tests, immunogenicity tests, adverse event assessment, concomitant therapies). The secondary objective is to characterize the pharmacokinetics of SBC-102 delivered by IV infusion after single and multiple doses (pre and post infusion Day 0 and 21). Inclusion criteria for late onset LAL deficiency subjects are as follows:

1. Patient understands the full nature and purpose of the study, including possible risks and side effects, and is willing and able to comply with all study procedures and provide informed consent;
 2. Male or female patients ≥18 and ≤65 years of age;
 3. Documented decreased LAL activity relative to the normal range of the lab performing the assay or documented result of molecular genetic testing confirming diagnosis of LAL Deficiency;
 4. Evidence of liver involvement based on clinical presentation (hepatomegaly) and/or laboratory test results (ALT or AST≥1.5×ULN);
 5. If on a statin or ezetimibe, the patient must be on a stable dose for at least 4 weeks prior to screening;
 6. All women must have negative serum pregnancy test at screening and cannot be breast feeding; and
 7. Female patients of childbearing potential must agree to use a highly effective and approved contraceptive method(s) for the duration of the study and continue to use for 30 days after last dose.

Clinical assessments include physical examinations, urinalysis, clinical chemistry analyses, CBC/hematology, acute phase reactants, coagulation studies, 12-lead ECG, Anti-SBC-102 antibodies, and PK to derive Cmax, $AUC_{inf}$, $T_{1/2}$, Cl and $V_{SS}$.

The patients are given 0.35 mg·kg$^{-1}$, 1 mg·kg$^{-1}$ or 3 mg·kg$^{-1}$ of LAL once weekly via intravenous (IV) infusion over 2 hours. The first subject is dosed and monitored for tolerability for at least 24 hours before proceeding to dosing the other subjects in the cohort. Each subject remains in-patient for 24 hours following their first infusion of SBC-102. Subjects continue with an additional 3 doses of once weekly IV infusions of the SBC-102 dose provided that tolerability and safety remain acceptable.

Pharmacokinetics

PK data are analyzed using all subjects entered into the study receiving at least one dose of study medication excluding any data points which may have been influenced by a major protocol deviation. PK analysis are performed using a one compartment infusion model. The following PK parameters are derived and presented by cohort (Cmax, $AUC_{inf}$, $T_{1/2}$, Cl and $V_{SS}$). Single and multiple dose PK parameters are compared using Visit 2 and Visit 6 data.

The proposed increment between doses in this study can be 3, 4, 5 or 6-fold, which may allow assessment of initial safety, tolerability, and pharmacokinetics in humans across a 6-fold range of doses on a mg·kg$^{-1}$ basis. In a relevant preclinical rat model, the pharmacodynamic effects of 1 mg·kg$^{-1}$ once weekly, 3 mg·kg$^{-1}$ every other week, and 5 mg·kg$^{-1}$ once weekly are comparable. Thus, although it is not anticipated that doses greater than 3 mg·kg$^1$ once weekly subjects are required, dose more than 3 mg·kg$^1$, such as 4, 5, 6, 7, 8, 9 or 10 mg·kg$^{-1}$ can be considered depending on the severity of the disease.

Study Design

Given the rarity of patients with this condition, the targeted number for this study is 9 evaluable subjects. Subjects are enrolled in three sequential cohorts of 3 subjects per cohort. Subjects assigned to cohort 1 commence dosing first, followed by those assigned to cohort 2, then those in cohort 3.

Cohort 1

Three subjects receive IV infusions of 0.35 mg·kg$^{-1}$ of SBC-102. The first subject is dosed and monitored for tolerability for at least 24 hours before proceeding to dosing the other 2 subjects in the cohort. Each subject remains in-patient for 24 hours following their first infusion of SBC-102. Subjects continue with 3 additional IV infusions of 0.35 mg·kg$^{-1}$ provided that tolerability and safety are acceptable.

Cohort 2

Three subjects receive IV infusions of 1 mg·kg$^{-1}$ of SBC-102. The first subject in Cohort 2 is dosed and monitored for tolerability for at least 24 hours before proceeding to dosing the other 2 subjects in the cohort. Each subject remains in-patient for 24 hours following their first infusion of SBC-102. Subjects continue with 3 additional IV infusions of 1 mg·kg$^{-1}$ provided that tolerability and safety are acceptable.

Cohort 3

Three subjects receive IV infusions of 3 mg·kg$^{-1}$ of SBC-102. The first subject in Cohort 3 is dosed and monitored for tolerability for at least 24 hours before proceeding to dosing the other subjects in the cohort. Each subject remains in-patient for 24 hours following their first infusion

TABLE 4

Late Onset LAL Deficiency Study Schedule: Visits, Assessments, and Intervals

| Assessments | Pre-treatment Visit 1 (Day-28 to-7) | Active Phase | | | | | | | | Post Active Phase | | |
|---|---|---|---|---|---|---|---|---|---|---|---|---|
| | | Visit 2 (Day 0) | Visit 3 (Day 1) | Visit 4 (Day 7 ± 1) | TC Day 8 | Visit 5 (Day 14 ± 1) | TC Day 15 | Visit 6 (Day 21 ± 1) | TC Day 22 | Visit 7 (Day 28 ± 1) | Visit 7.1 (Day 35 ± 1) | Visit 8 (Day 52 ± 1) |
| Informed Consent | X | | | | | | | | | | | |
| Inclusion/Exclusion Criteria | X | X | | | | | | | | | | |
| Demographic Information | X | | | | | | | | | | | |
| Patient Health Outcomes | X | | | | | | | | | | | |
| Medical History[1] | X | | | | | | | | | | | |
| 12-lead ECG | X | | | | | | | | | | | X |
| Physical Examination | X[2] | X | | | | | | X | | X[2] | | X |
| Vital Signs[3] | X | X[3] | X | X[3] | | X[3] | | X[3] | | X | | X |
| Urinalysis | X | X[P] | X[P] | X | | X | | X | | X | | X |
| Pregnancy Test[4] | X | X[P] | | | | | | X[P] | | | | X |
| CBC/Hematology | X | X[P] | X[P] | X[P] | | X[P] | | X[P] | | X | | X |
| Chemistry Panel | X | X[P] | X[P] | X[P] | | X[P] | | X[P] | | X | | X |
| Liver Panel | X | X[P] | X[P] | X[P] | | X[P] | | X[P] | | X | X | X |
| Lipid Panel | X | X[P] | | | | | | | | X | | |
| Acute Phase Reactants | X | X[P] | | | | | | | | X | | X |
| Coagulation Tests | X | | | | | | | | | | | X |
| Viral Hepatitis Screen | X | | | | | | | | | | | |
| Autoimmune Hepatitis Screen | X | | | | | | | | | | | |
| DNA Sample | X | | | | | | | | | | | |
| Blood PBMC LAL activity | X | | | | | | | X[P] | | | | X |
| Anti SBC-102 Ab (ADA) | X | X[P] | | | | | | | | X | X | X |
| Exploratory Biomarker Sample | X | X[P] | | | | | | | | X | X | X |
| PK Sample[5] | | X | | | | | | X | | | | |
| SBC-102 Dosing | | X | | X | | X | | X | | | | |
| Adverse Events | X | X | X | X | X | X | X | X | X | X | X | X |
| Concomitant Therapies | X | X | X | X | X | X | X | X | X | X | X | X |

TC = Telephone Call
[P]Pre-dose
[1]Including alcohol history (AUDIT questionnaire)
[2]Including height and weight
[3]Pre-dose, every 15 minutes during infusion, every 15 minutes for the 2 hours after the infusion and every 30 minutes for hours 2-4 after the infusion
[4]Serum at Visit 1 and Visit 8; urine at Visit 2 and Visit 6
[5]Pre-dose, 10, 15, 20, 40, 60, 90 minutes during the infusion, at the end of the infusion (approx. 120 minutes) and at 5, 10, 20, 30, 40, 60 and 120 minutes after the infusion of SBC-102. Subjects continue with 3 additional doses of once weekly IV infusions of 3 mg·kg$^{-1}$, provided that tolerability and safety are acceptable.

The Safety Committee (SC) may suspend dosing for an entire cohort or for an individual subject at any point due to poor tolerability or potential safety risks.

If the subject is discontinued from study treatment at a scheduled visit other than Visit 8 (End of Study) or at an unscheduled visit, the subject should return no earlier than 7 days after the last dose of SBC-102 for the End of Study assessments conducted at Visit 8.

SBC-102 is administered by IV infusion on Visits 2, 4, 5 and 6. Concomitant therapies are recorded throughout the study. Adverse events are recorded from the time of signing of the informed consent.

Each subject receives a total of four weekly doses of SBC-102 provided that tolerability and safety remain acceptable.

Study Duration

The study involves 4-weeks of dosing with SBC-102 and a wash-out period to support evaluation of safety and dosing scheduling for subsequent clinical trials. After completion of this study, subjects may be eligible to resume SBC-102 under a separate protocol to assess the long-term safety and efficacy of SBC-102 in patients with LAL Deficiency/CESD phenotype.

Physical Examination

A general physical examination is performed by a medically qualified person. Systems (including, but not limited to, the cardiovascular, respiratory, gastrointestinal and neurological systems) should be specified and recorded. Any abnormalities should be stated each time the examination is performed. Diagnosis of new abnormalities should be recorded as adverse events, if applicable.

Additional physical examination assessments to be performed at the Screening Visit:
  a) Liver size: A clinical assessment of liver size (palpable/non palpable and centimeters below costal margin), regularity (smooth/nodular) and sensitivity (tender/non tender) is made.
  b) Lymphadenopathy: An assessment of the size, location, and character of any palpable lymph nodes is made. Areas to be examined include: cephalic (occipital, preauricular, postauricular, submental, submandibular), cervical, clavicular, axillary, and inguinal. Any enlarged nodes is characterized as tender or non-tender.
  c) Arterial disease: Right and left Posterior Tibialis and Dorsalis Pedis pulses are assessed clinically and right and left ankle brachial indexes (ABI) are recorded. ABI is defined as the ratio of the systolic pressure at the dorsalis pedis or posterial tibial artery divided by the right or left arm brachial systolic pressure (whichever is higher).

Vital Signs

Vital signs, including pulse rate, respiratory rate, systolic and diastolic blood pressure and temperature, are measured. Assessment of pulse rate and blood pressure are taken after the subject has been in a semi-supine position for at least 5 minutes. On dosing days, vital signs are recorded pre-infusion, every 15 minutes (±5) during infusion and for 2 hours after the infusion and then every 30 minutes (±10) between 2 and 4 hours after the infusion is completed. Additional readings may be taken at the discretion of the Investigator in the event of an infusion related reaction (IRR). 12-lead electrocardiogram (ECGs) with formal recordings are taken after the subject has been supine for at least 5 minutes.

Laboratory Assessments

Samples for laboratory tests are collected at the time points indicated in the Schedule of Assessments. The following analyses (with the exception of ESR, coagulation studies and anti-SBC-102 antibodies) are performed.
  CBC/Hematology: White blood cell count, red blood cell count, hemoglobin, hematocrit, mean corpuscular volume (MCV), mean corpuscular hemoglobin (MCH), mean corpuscular hemoglobin concentration (MCHC), platelet count, neutrophil, lymphocytes, monocytes, eosinophils, basophils
  Chemistry Panel: Glucose, urea nitrogen, creatinine, sodium, potassium, chloride, calcium, magnesium, inorganic phosphorus, total protein, lactate dehydrogenase, uric acid
  Liver Function Test: AST/SGOT, ALT/SGPT, alkaline phosphatase, GGTP, albumin, bilirubin (direct, total)
  Lipid Panel: Total cholesterol, triglyceride, HDL, LDL
  Coagulation Studies: Prothrombin time (PT) international normalized ratio (INR), activated partial thromboplastin time (aPTT)
  Urinalysis: Glucose, ketones, blood, pH, protein, nitrite, and leukocytes (microscopic examination will only be done if blood, protein, nitrite and/or leukocytes are abnormal)
  Viral Hepatitis Screen: HBsAg and HCV serology (at screening or if clinically indicated during trial)
  Autoimmune Hepatitis Screen: anti-smooth muscle antibody (ASMA), anti-nuclear antibodies (ANA), anti-LKM1 antibody, anti-SLA antibody
  Anti-drug Antibody: Anti-SBC-102 antibody
  Acute Phase Reactants: High sensitivity C-reactive protein (CRP), erythrocyte sedimentation rate (ESR) and serum ferritin
  Pregnancy Test: All women have, at a minimum, monthly pregnancy tests. These are performed using serum at Visit 1 and Visit 8 and urine at Visit 2 and Visit 6.

Pharmacokinetic (PK) assessments: PK samples are taken from the arm opposite the infusion cannula. Intensive sampling for measurement of SBC-102 serum levels on Day 0 (Dose 1, Visit 2) and Day 21 (Dose 4, Visit 6) is collected: immediately pre-dose (within 30 minutes of dosing); At 10(±1), 15(±1), 20(±1), 40(±2), 60(±2) and 90(±2) minutes during the infusion and at the end of the infusion (approximately 120 minutes); and at 5(±1), 10(±1), 20(±1), 30(±1), 40(±2), 60(±2) and 120(±2) minutes after completion of the infusion.

Preparation of SBC-102

The subject's weight recorded on Visit 1 is used for calculating SBC-102 volume for each infusion. SBC-102 drug product for IV infusion is prepared by dilution using the following steps:
  1. Vials are removed from the refrigerator.
  2. It is confirmed that the expiration date on the vial has not passed.
  3. The calculated total volume of SBC-102 required for dosing is determined.

Example:
Subject Wt (in kg): 70 kg
Subject dose level: 3 mg·kg$^{-1}$
Drug concentration: 2.0 mg·mL$^{-1}$
  1. Calculation of Subject Dose:

$$\text{Weight (in kg)} \times \text{Dose Level} = \text{Total Dose}$$
$$70 \text{ kg} \times 3 \text{ mg·kg}^{-1} = 210 \text{ mg}$$

2. Calculation of Injection Volume:

$$\text{Total daily dose} \div \frac{\text{Drug concentration in vial}}{} = \frac{\text{Total Injection Volume}}{}$$

$$210 \text{ mg} \div 2.0 \text{ mgmL}^{-1} = 105 \text{ mL}$$

4. The following 0.9% saline infusion bags are used based on the dosing group assignment:

| Cohort | Dose (mg · kg$^{-1}$) | Infusion Bag Volume (mL) |
|---|---|---|
| 1 | 0.35 | 100 |
| 2 | 1 | |
| 3 | 3 | 250 |

5. A volume equivalent to the volume of SBC-102 required for dosing (as calculated in step 3 above) is removed from either a 100 mL or 250 mL infusion bag of 0.9% saline (i.e., using the example above, 105 mL of saline is removed from a 250 mL infusion bag).
6. The calculated total volume of SBC-102 to the 0.9% saline infusion bag is drawn up and transferred (i.e., using the example above, 105 mL of SBC-102 solution is drawn up and transferred to the infusion bag).
7. Gentle inversion is used to mix the bag.

Administration of rhLAL
1. The IV infusion tubing is attached to the diluted bag of SBC-102.
2. The tubing is primed, and all air is expelled.
3. The infusion rate on the flow-regulating device is set to administer the total volume at the following rates over approximately 100 minutes:

| Cohort | Dose (mg · kg$^{-1}$) | Infusion Rate (per hour) | Infusion Rate (per minute) |
|---|---|---|---|
| 1 | 0.35 | 60 mL | 1 mL |
| 2 | 1 | | |
| 3 | 3 | 150 mL | 2.5 mL |

4. The IV infusion site, which varies by subject and can include antecubital or wrist veins (or a central venous catheter) is selected.
5. The IV tubing is attached to the angiocatheter. Saline is injected into the IV line to assess patency and to verify that the saline flushes easily.
6. The IV line is secured with tape.
7. SBC-102 infusion is begun using a flow-regulating device.
8. Infusion is monitored regularly.
9. When the bag is empty, 25 mLs of 0.9% saline is immediately injected into the infusion bag using the injection port.
10. The line is flushed at the same infusion rate (60 mL per hour [1 mL per minute] for the 0.35 mg·kg$^{-1}$ and 1 mg·kg$^{-1}$ dose and 150 mL per hour [2.5 mL per minute] for the 3 mg·kg$^{-1}$ dose) until completion of the infusion. The end of the infusion is defined when the infusion and flush has completed and is documented.

Infusion Reactions

An infusion-related reaction (IRR) is defined as any immunologically-mediated adverse event that is at least possibly related to infusion. IRRs are classified as either acute (occurring within 24 hours of the start of the infusion) or delayed (occurring between 1 and 14 days after the infusion).

Medications and equipment for the treatment of hypersensitivity reactions must be available for immediate use in case of unexpected severe hypersensitivity reactions. They include, but are not restricted to, oxygen, acetaminophen, antihistamines (e.g. diphenhydramine, parenteral and PO), corticosteroids, epinephrine (adrenaline) and cardiopulmonary resuscitation devices.

Signs of a possible acute IRR can be hyperemia, flushing, fever and/or chills, nausea, pruritus, urticaria, gastro-intestinal symptoms (vomiting, diarrhea, abdominal cramping), cardiopulmonary reactions, including chest pain, dyspnea, wheezing, stridor, hypotension or hypertension. If any of the above signs and symptoms is observed during the infusion and the subject remains hemodynamically stable: the infusion rate must be slowed or stopped. If the subject continues to show signs of hypersensitivity, an IM or slow IV dose of an antihistamine should be administered. In subjects who experience severe infusion reactions with clinically significant cardiovascular or respiratory effects, the infusion is discontinued. In such an anaphylactic reaction, subject can be treated with intravenous antihistamines, corticosteroids and epinephrine.

Example 8

Administration of Recombinant LAL in a Rat Model

The effects of repeat-dosing with recombinant human LAL on weight, tissue triglycerides and cholesterol, hepatomegaly, splenomegaly, lymphadenopathy, intestinal weight, and other parameters were evaluated in LAL Deficient Donryu rats described in Yoshida and Kuriyama (1990) Laboratory Animal Science, vol 40, p 486-489 (see also Kuriyama et al (1990) Journal of Lipid Research, vol 31, p 1605-1611; Nakagawa et al, (1995) Journal of Lipid Research, vol 36, p 2212-2218), the disclosure of which is incorporated in its entirety herein by reference. At 4 weeks of age, Donryu rats which are homozygous for the LAL deletion (LAL-/-), were assigned into groups to either be dosed with recombinant human LAL produced in a transgenic chicken oviduct system or a saline placebo. Wild-type, age-matched, littermate rats were used as controls. The LAL-/- rats were dosed once a week for four weeks (four doses total) or once every two weeks for four weeks (two doses total) by tail-vein injection as a single dose or in two equal doses given 30 minutes apart. Doses of recombinant LAL were 1 mg/kg or 5 mg/kg. Dosing schedule is shown in Table 5. The rats were pretreated with diphenhydramine (5 mg/kg) to counteract potential anaphylactic reactions, a procedure which is based on previous experiences in animal models of enzyme replacement therapy for the treatment of lysosomal storage disease (Shull et al. (1994) Proceedings of the National Academy of Science, vol 91, p. 12937; Bielicki et al. (1999) The Journal of Biological Chemistry, 274, p. 36335; Vogler et al. (1999) Pediatric Research, 45, p. 838.), the disclosure of which is incorporated in its entirty herein by referernce.

Figure 9:
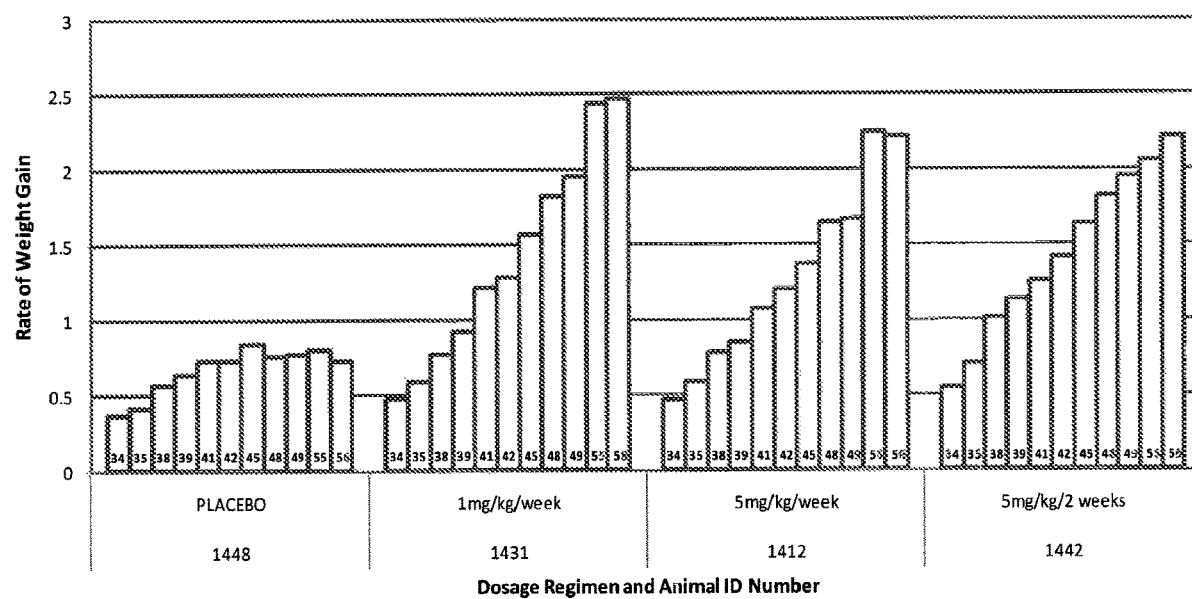
FIG. 9 illustrates the rate of weight gain in four age-matched, male rats each assigned to one of the following four exogenous LAL dosage regimes: 1 mg per kilogram once a week, 5 mg per kilogram once a week, 5 mg per kilogram once every 2 weeks, or placebo. Numbers inside the columns represent days post birth.

FIG. 9 shows the daily progress in weight gain of rats which were administered either 1 mg/kg of recombinant LAL per week or 5 mg/kg of recombinant LAL per week or 5 mg/kg of recombinant LAL per two weeks. It can be seen in the figure that there is little or no difference in therapeutic effect between the two dose sizes and frequencies.

TABLE 5

Weighing and Dosing Schedule of LAL Deficient Donryu rats

| Day from Birth | Assessments/Injections Performed |
|---|---|
| Day 13 | WEIGHED |
| Day 14 | |
| Day 20 | |
| Day 21 | Pups Weaned |
| Day 24 | |
| Day 25 | |
| Day 27 | |
| Day 28 | First Injection for administration once every week and once every two weeks |
| Day 31 | |
| Day 32 | |
| Day 34 | |
| Day 35 | Second Injection for administration once every week |
| Day 38 | |
| Day 39 | |
| Day 41 | |
| Day 42 | Third Injection for administration once every week; Second administration for once every two weeks |
| Day 45 | |
| Day 48 | |
| Day 49 | Fourth injection for administration once every week |
| Day 55 | |
| Day 56 | Necropsy |

Example 9

Pathologic Examination of LAL−/− Rats Treated with Recombinant LAL

At the termination of the study described in Example 8, study animals were humanely euthanized and necropsied to examine gross pathology, histopathology, and clinical chemistry. The gross necropsy included examination of the external surface of the body, all orifices, and the cranial, thoracic, and abdominal cavities and their contents. Mass of internal organs and tissues were determined for the rats and the organs and tissues were harvested and fixed in 10% neutral-buffered formalin. Following fixation, the tissues were processed and histological slides of hematoxylin and eosin-stained sections were prepared and evaluated.

Figure 10:
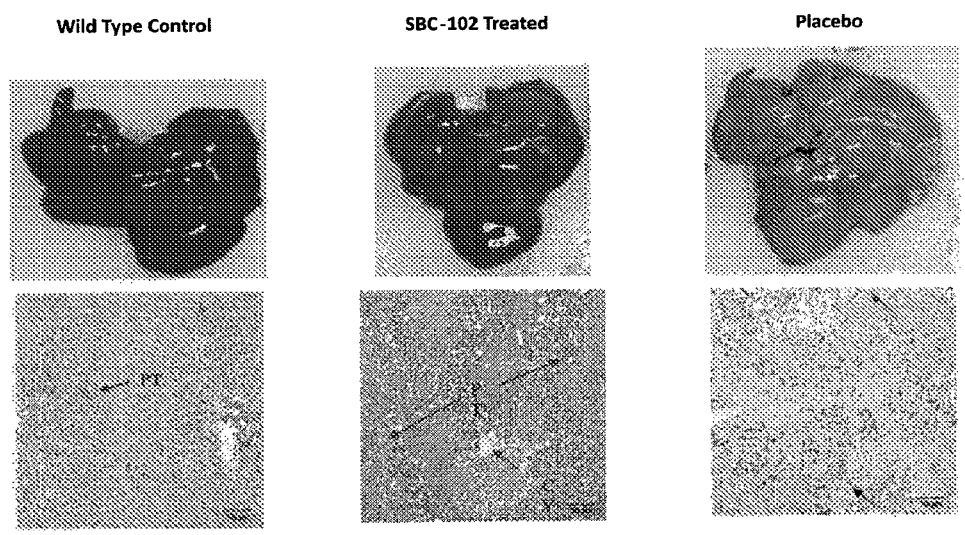
FIG. 10 depicts the results of pathological and histopathological examination of a wild-type control, an LAL deficient rat treated with exogenous LAL, and an LAL deficient placebo-treated rat. Gross pathology demonstrates a normalization of color and size of the liver in rats treated with exogenous LAL. Histopathology of liver tissue from rats treated with exogenous LAL shows essentially normal liver histology in marked contrast to the substantial accumulation of foamy macrophages in the placebo-treated animals.

The gross pathological examination of treated animals analyzed showed a substantial normalization in liver size and color as can be seen in the dissection shown in FIG. 10. Organ-to-body weight ratios were determined and demonstrated a reduction in the relative organ size for liver, spleen, mesenteric tissue, duodenum, jejunum and ileum in successfully treated animals which were dissected, as compared to the placebo treated rats. Histopathology of liver tissue from recombinant LAL-treated rats analyzed shows essentially normal liver histology in marked contrast to the substantial accumulation of foamy macrophages in the placebo-treated animals (FIG. 10).

Example 10

Internalization of Recombinant Human LAL in Macrophage and Fibroblast Lysosomes

The ability of transgenic avian derived recombinant human LAL ("SBC-102") to bind to cells and be internalized to the lysosomal compartment, was examined in vitro using macrophage and fibroblast cells. When incubated with macrophage cells, fluorescently-labeled SBC-102 was found to localize to the lysosomes. This effect could be attenuated by using a mannose polysaccharide competitor, implicating the N-acetylglucosamine/mannose (GlcNAc/mannose) receptor as a mechanism of recognition and uptake by these cells. SBC-102 increased the cell-associated LAL activity in both LAL-deficient human fibroblasts and normal murine fibroblasts after incubation in vitro, indicating that exposure to SBC-102 can result in substantial replacement of deficient enzymatic activity.

Mannose-6-phosphate (M6P) is present in the oligosaccharide structures of SBC-102 which have been shown to be involved in the delivery of lysosomal enzymes to a wide variety of cells types via the ubiquitous M6P receptor.

Recombinant LAL was purified from the egg white of transgenic hens. Oregon Green NHS was obtained from Invitrogen™ (#0-10241). The rat alveolar macrophage line, NR8383, and the mouse fibroblast line, NIH-3T3, were obtained from ATCC. LAL-deficient Wolman's fibroblasts were obtained from Coriell Institute for Medical Research and LysoTracker® Red was obtained from Invitrogen™.

Enzyme labeling: 4 mg of transgenic avian derived LAL in PBS was labeled with Oregon Green, according to the manufacture's recommendations and reaction was subsequently dialyzed against PBS then concentrated.

Macrophage uptake: Fluorescently-labeled transgenic avian derived LAL (5 µg/mL) and LysoTracker® Red were incubated with NR8383 cells for 2 hours. Cells were examined by co-focal fluorescence microscopy using a sequential scanning mode at 488 nm and then 514 nm.

Competitive inhibition with, mannan: Fluorescently-labeled SBC-102 (5 ug/mL) and mannan were incubated with NR8383 cells for 2 hours. Cells were trypsinized, and recombinant LAL uptake was measured by florescence-activated cell sorting using median fluorescence intensity as the endpoint.

Figure 11:
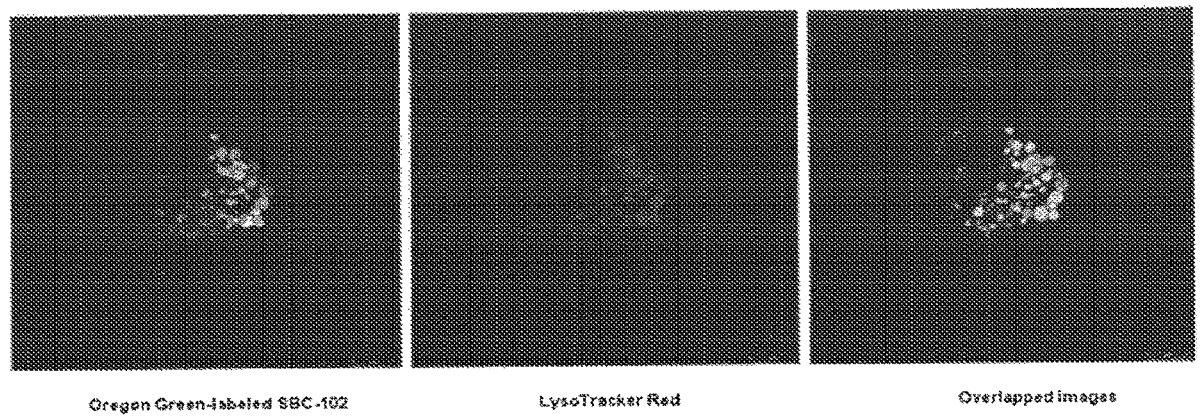
FIG. 11 depicts the co-localization of recombinant human LAL (SBC-102) and lysosomal marker in the lysosomes of cells examined by confocal fluorescence microscopy using a sequential scanning mode.

The ability of transgenic avian derived LAL to be taken up and subsequently incorporated into the lysosomes of target cells was examined using the macrophage cell line, NR8383. Fluorescently-labeled transgenic avian derived LAL and the lysosomal marker, "LysoTracker® Red" (Invitrogen™), were incubated with cells for 2 hours. The co-localization of transgenic avian derived LAL and lysosomal marker in the lysosomes of these cells was subsequently examined by confocal fluorescence microscopy using a sequential scanning mode (FIG. 11). The recombinant LAL demonstrated localization to lysosomes, which is consistent with similar in vitro studies using recombinant human (rhLAL) from a variety of sources.

Figure 12:
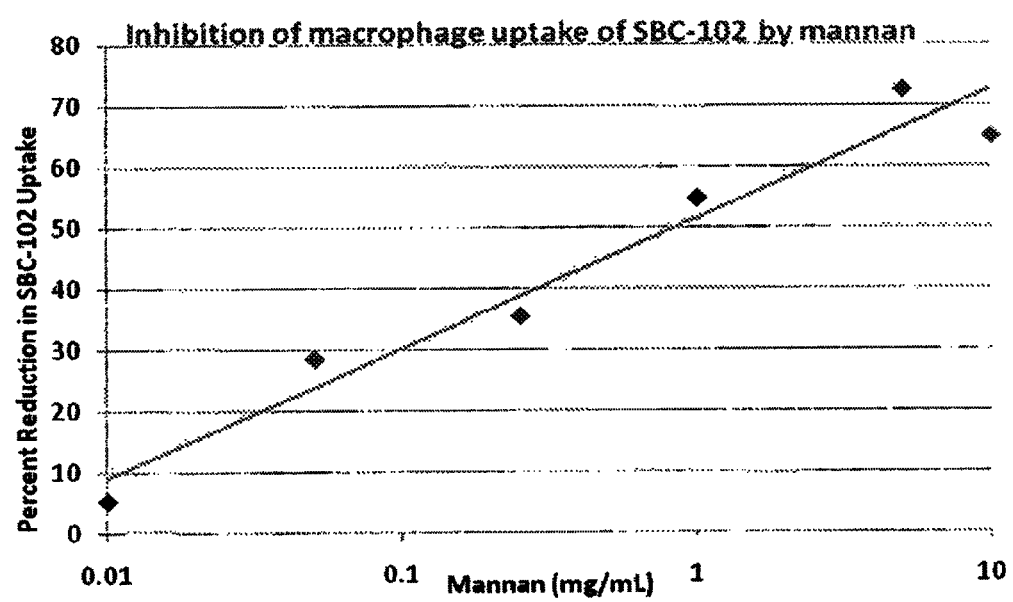
FIG. 12 depicts the binding specificity of recombinant human LAL (SBC-102) to the GlcNAc/mannose receptor assessed by competitive binding assays using the macrophage cell line, NR8383.

The binding specificity of transgenic avian derived LAL to the GlcNAc/mannose receptor has been assessed by competitive binding assays using the macrophage cell line, NR8383 (FIG. 12). Fluorescently-labeled (Oregon Green) transgenic avian derived LAL at 5 µg/mL and various concentrations of the mannose-containing oligosaccharide, mannan, were co-incubated with cells for 2 hours. The relative inhibition of transgenic avian derived LAL uptake by mannan, as compared with no mannan control, was quantified by fluorescence-activated cell sorting analysis using median fluorescence intensity as the endpoint. A mannose dose dependent inhibition in transgenic avian derived LAL binding/uptake was observed, which is consistent with transgenic avian derived LAL: GlcNAcR interaction.

In addition, mannose-6-phosphate mediated uptake in fibroblast cells was demonstrated by competition experiments with mannose-6-phosphate.

Example 11

Increase of LAL Activity in Treated Cells

LAL catalyzes the hydrolysis of cholesterol esters and triglycerides to free cholesterol, glycerol, and free fatty acids. Thus, LAL activity can be measured, for example, by the cleavage of the fluorogenic substrate, 4-methylumbelliferyl oleate (4MUO).

Fibroblasts

Figure 13:
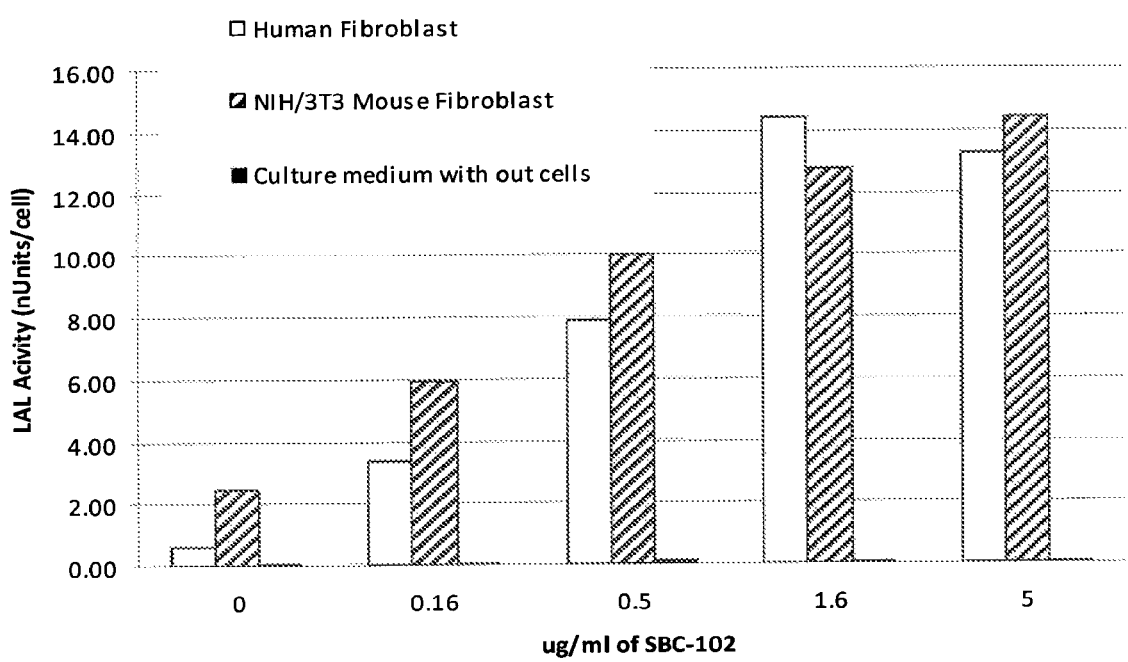
FIG. 13 depicts the activity of recombinant human LAL in cells in normal and LAL-deficient cells in vitro.

The ability of transgenic avian derived LAL exposure to increase LAL activity in cells has been examined using both normal and LAL-deficient cells in vitro. Fibroblasts were isolated from a Wolman's patient and a normal murine fibroblasts (NIH-3T3) were incubated in the presence of transgenic avian derived LAL at concentrations of either 0, 0.16, or 0.5 micrograms/mL for 5 hours. Cells were then washed to remove non-specific signal, and cell lysates were assayed for LAL activity using 4-methylumbelliferyl oleate (4-MUO) substrate. FIG. 13 demonstrates that endogenous cell-associated LAL activity was lower in Wolman's fibroblasts compared to NIH-3T3, and dose-dependent increases in LAL activity were observed in both cell types after incubation with transgenic avian derived LAL (FIG. 13).

Leukocytes

Serum monocuclear leukocytes were obtained from LAL deficient patients pre- and post-administration. Blood samples were stored refrigerated without loss of enzyme activity. Mononuclear leukocytes (lymphocytes) were isolated from blood using a preparation of Ficoll and sodium diatrizoate. 4-8 mL blood, previously diluted 1:1 with Hanks' balanced salt solution, was layered gently over 3 mL Ficoll-Paque and centrifuged. The mononuclear cell ring was aspirated and washed once with Hanks' solution, then at least twice by resuspending the pellet in 1-2 mL water. Pellets were frozen at −20° C. before use. Prior to assay, pellets were thawed, resuspended in distilled water and sonicated on ice. The preparation was then centrifuged at 20,000×g for 15 min at 4° C. The supernatant (containing 0.5-1.5 mg protein/mL) was kept on ice, prior to assay.

The substrate for the acid lipase assay was prepared by adding 1 ml 10 mM 4MUO (4-methylumbelliferyl oleate) in hexane to 1 mL 16 mM L-α-phosphatidylcholine in $CHCl_3$. The solvents were evaporated under $N_2$ and 25 ml 2.4 mM taurodeoxycholic acid (sodium salt) in water were added. The mixture was sonicated on ice for 1-2 min at 30-40 W. Prior to assay, 1 vol. substrate stock was diluted with 7 vols. 200 mM sodium acetate/acetic acid buffer (pH 4.0). Each 2 mL reaction cuvette contained 100 nmol 4-methylumbelliferyl oleate, 160 nmol L-α-phosphatidylcholine and 600 nmol sodium taurodeoxycholate.

The reaction was started by adding 5-100 μL enzyme and was monitored at 37° C. using a spectrophotofluorimeter. Cleavage of 4MUO was detected, for example, by excitation at about 360 nm and emission at about 460 nm of the released flurophore, 4-methylumbelliferone (4MU). The change in fluorescence with time was recorded.

Example 12

In Vivo Analysis of Recombinant Human LAL (SBC-102)

LAL-deficient Yoshida Rats (i.e., Homozygous) (see Kuriyama et al. (1990), Journal of Lipid Research, vol. 31, p 1605-1611; Nakagawa et al., (1995) Journal of Lipid Research, vol. 36, p 2212-2218; and Yoshida and Kuriyama (1990) Laboratory Animal Science, vol. 40, p 486-489) were treated with either SBC-102 (5 mg/kg, IV) or placebo, once/week for four weeks beginning at four weeks of age. For each administration the SBC-102 was injected into the rat tail vein in two equal doses (2.5 mg/kg) 30 minutes apart. Rats and aged-matched wild-type controls were examined one week after the final dose. Analyses were done in triplicate.

Gross pathologic examination of the SBC-102 treated animals demonstrated normalization in liver color in addition to reduction in organ size. The SBC-102 treated rats showed essentially normal liver histology in marked contrast to the substantial accumulation of foamy macrophages in the vehicle-treated animals. Serum alanine and aspartate transferase levels, which are elevated in $LAL^{-/-}$ rats, were also reduced in SBC-102 treated rats.

Figure 14:
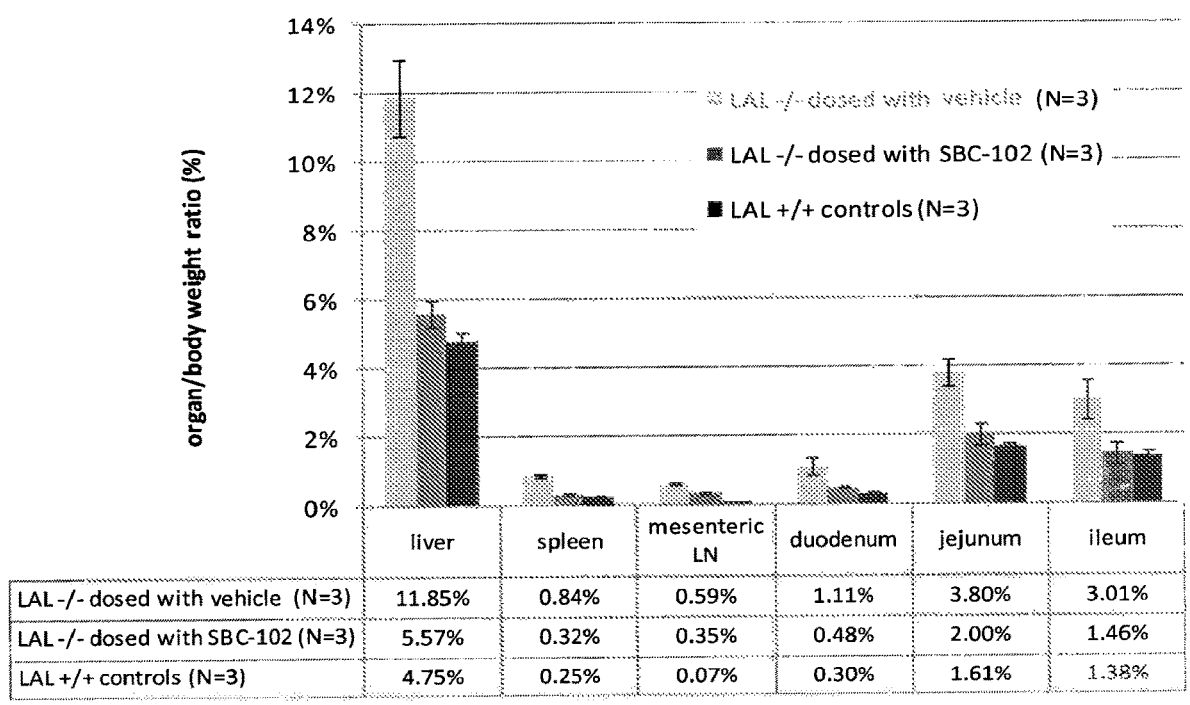
FIG. 14 illustrates the effect of recombinant human LAL (SBC-102) treatment on internal organs mass of LAL deficient rats. Organ size is represented as percent of body weight determined at 8 weeks of age, in $LAL^{-/-}$ rats and $LAL^{+/+}$ rats after weekly administration of vehicle or SBC-102 at 5 mg/kg for 4 weeks.

Mass of internal organs and tissue was determined for each rat and the data is shown in FIG. 14. Organ size is represented as percent of body weight determined at 8 weeks of age, in $LAL^{-/-}$ rats and $LAL^{+/+}$ rats after weekly administration of vehicle or SBC-102 at 5 mg/kg for 4 weeks.

Figure 15:
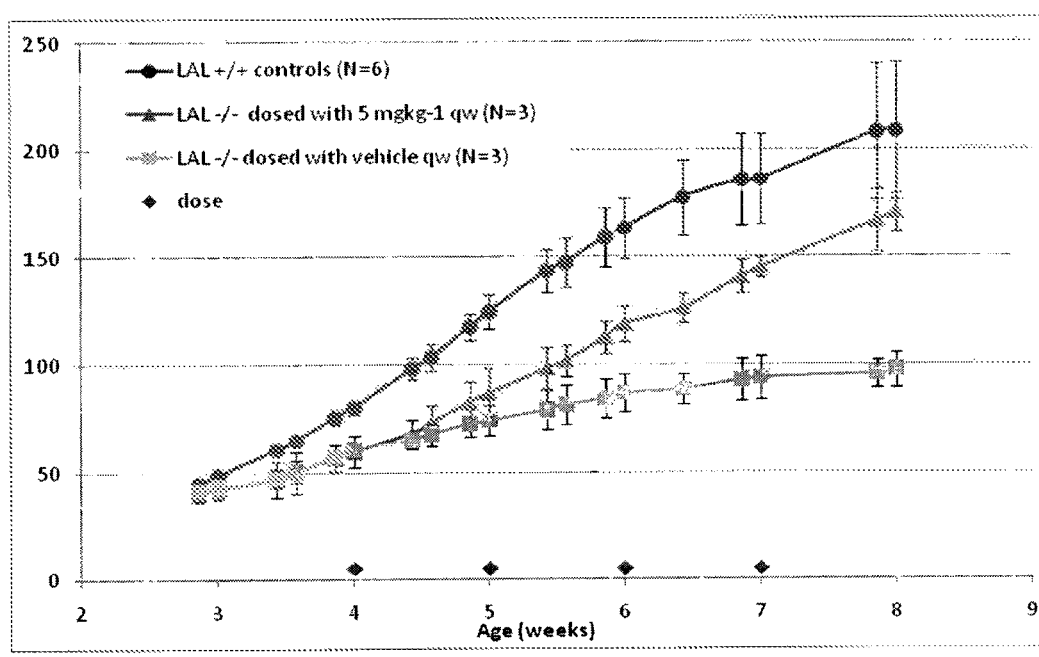
FIG. 15 illustrates body weight in wild type and LAL-deficient rats after weekly dose of vehicle or SBC-102 at 5 mg·kg$^{-1}$ for 4 weeks. Dose administration is highlighted on X-axis by diamonds starting at 4 week.

Body weights of SBC-102- or vehicle-treated Yoshida rats were compared with wild type rats, as is shown in FIG. 15. SBC-102 (5 mg/kg) or vehicle was administered by IV injection either as a single dose or as split doses (given within 4 hour period) to $LAL^{-/-}$ rats. $LAL^{+/+}$ rats were age-matched littermate controls.

Example 13

Triglyceride Analysis

Triglyceride analysis was performed on liver and spleen tissue from wild type, homozygous placebo and homozygous SBC-102 treated animals. The triglyceride analyses were performed using standard methodologies (i.e., MBL International's Triglyceride Quantification Kit Catalog #JM-K622-100) and were done in triplicate.

TABLE 6

Liver and Spleen Triglyceride levels in wild-type and LAL deficient rats
Triglyceride (ug/mg wet tissue)

|  | Wild Type (n = 3) | Placebo (n = 3) | SBC-102 (n = 3) |
|---|---|---|---|
| Liver | 48 | 84 | 57 |
| Spleen | 3 | 22 | 4 |

Liver Substrate Levels

Figure 16:
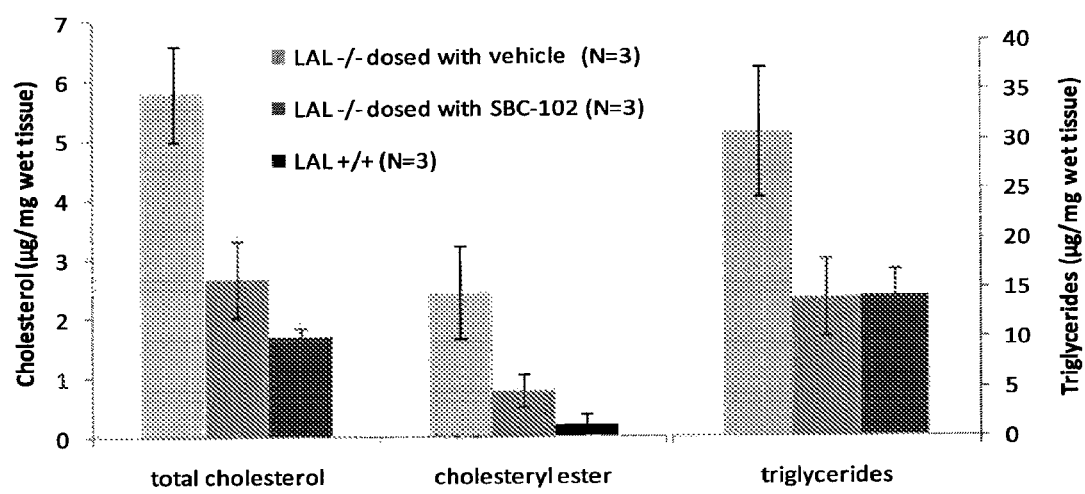
FIG. 16 depicts levels of liver cholesterol, cholesteryl ester and triglyceride determined at 8 weeks of age in WT and LAL deficient rats after weekly dose of vehicle or SBC-102 at 5 mg·kg$^{-1}$ for 4 weeks.

FIG. 16 shows liver cholesterol, cholesteryl ester and triglyceride levels determined at 8 weeks of age, in WT and LAL deficient rats after weekly administration of vehicle or SBC-102 at 5 mg·kg$^{-1}$ for 4 weeks.

Example 14

Rat Dose Response Study

Figure 17:
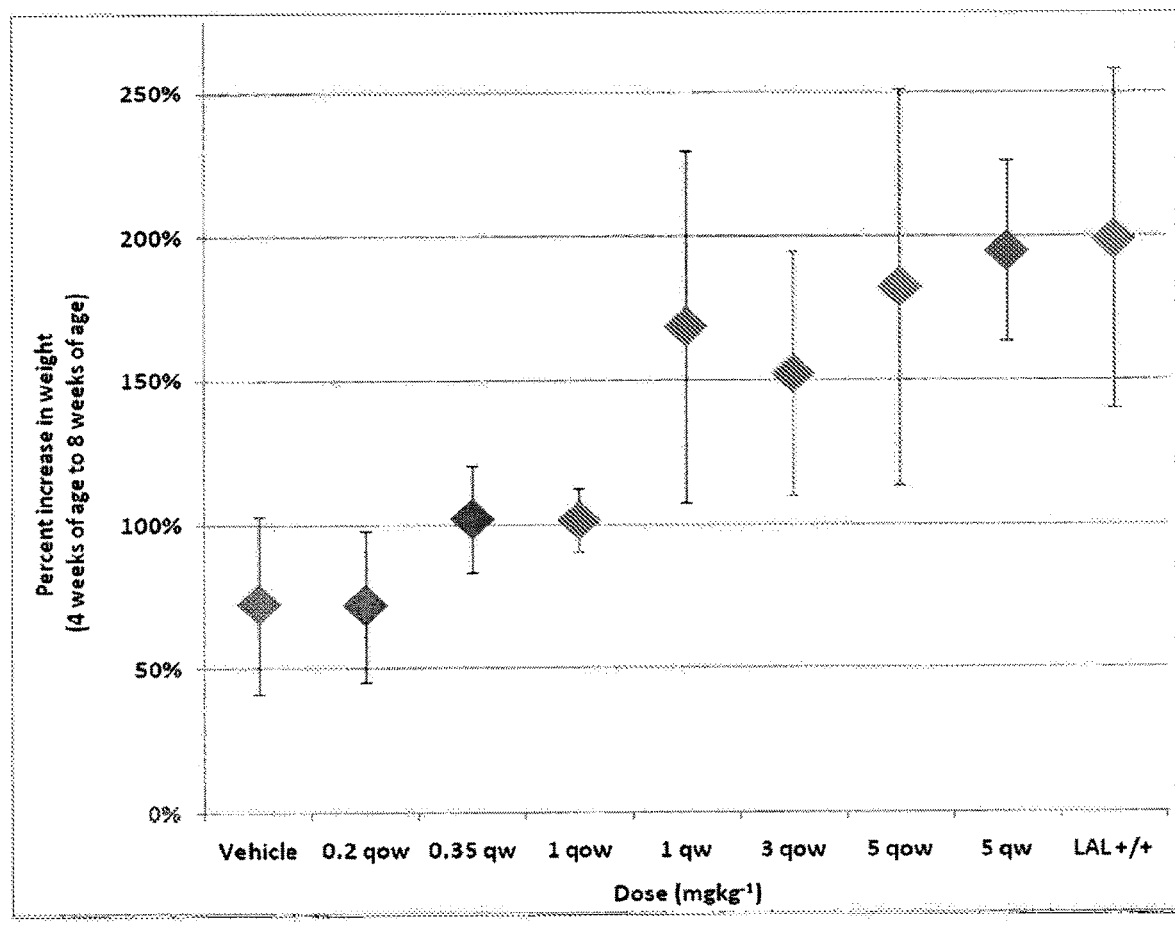
FIG. 17 depicts percent increase of body weight in LAL-deficient rats.
Figure 18:
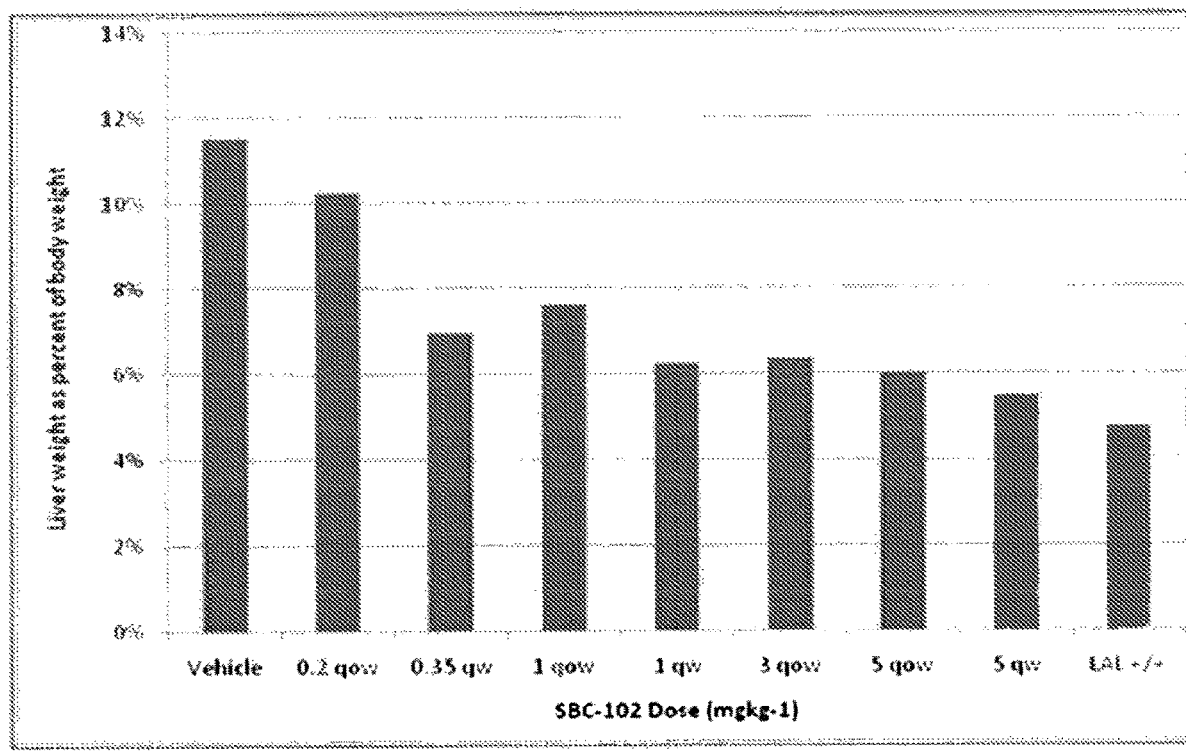
FIG. 18 depicts liver weight, as a percent of body weight, in LAL-deficient rats after administration of SBC-102 for 4 weeks.
Figure 19:
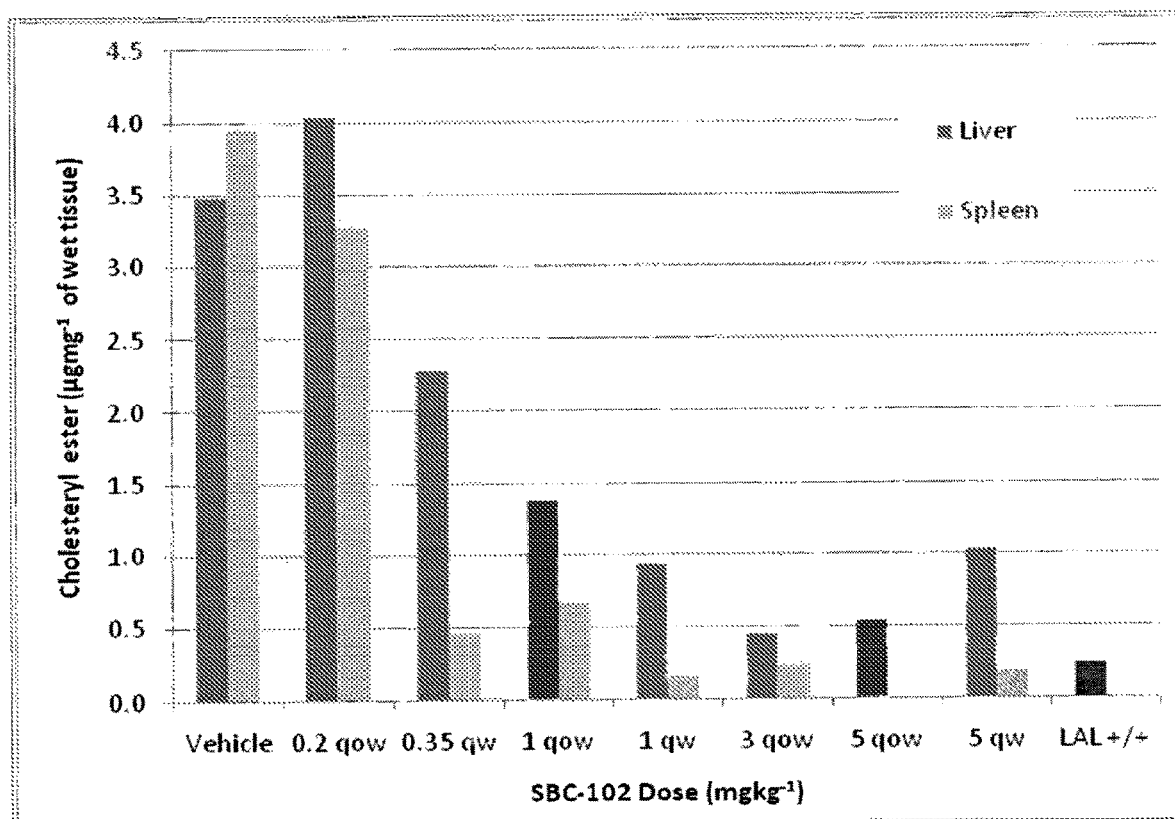
FIG. 19 illustrates levels of tissue cholesteryl ester in LAL-deficient rats after administration of SBC-102 for 4 weeks.

Based on the studies performed above, the pharmacodynamic (PD) effects of a range of doses and dose schedules (qw and qow) of LAL ("SBC-102") were examined in LAL rats. In these studies, SBC-102 was administered by IV injections at dosages of 0.2, 1, 3 and 5 mg/kg, qow, or 0.35, 1.0 and 5.0 mg/kg, qw, for 1 month, beginning at 4 weeks of age. Results demonstrate improvements in body weight (BW) gain (FIG. 17), organomegaly (FIG. 18), and tissue substrate levels (FIG. 19). Serum transaminase levels were also reduced as the SBC-102 dose increased, with levels reaching essentially wild-type levels at the higher doses.

Example 15

Pharmacokinetics of SBC-102 a. Sampling

PK samples were taken from adult patients suffering from late onset LAL deficiency. The patients were dosed with 0.35 mg/kg for two hours. Serum samples on Day 0 (Dose 1, Visit 2) and Day 21 (Dose 4, Visit 6) were collected immediately pre-dose (within 30 minutes of dosing); at 10(±1), 15(±1), 20(±1), 40(±2), 60(±2) and 90(±2) minutes during the infusion (DI) and at the end of the infusion (EOI) (approximately 120 minutes from the beginning of the infusion); and at 5(1), 10(±1), 20(±1), 30(±1), 40(±2), 60(±2) and 120(±2) minutes after completion of the infusion (AI).

b. Serum Enzymatic Assay

4-MUO (4 mM) kept in −20° C. freezer was thawed in a 4° C. refrigerator in the dark and placed in a 25° C. incubator for 1.5 hours in the dark prior to use. Standard was prepared by diluting SBC-102 drug product to 1.56 ng/mL. A blank assay buffer was included. All samples were diluted to 50 ng/mL for the first dilution. Standards and samples were plated immediately after making dilutions. After standards and samples were prepared, 62.5 uL of Assay Buffer (0.2 mol/L sodium acetate trihydrate, pH 5.5) was added to each well. 12.5 uL of standards and samples were added each well, in duplicate. 4-MUO (4 mM) was diluted to 1.6× with 4% Triton X-100 and added 25 uL per well. The multi-well plate was tapped a few times to mix, sealed tightly, and placed in a 37° C. incubator for 30 minutes. After incubation, 50 uL of stop solution (0.77M Tris pH 8.0) was added to each well to make a final volume of 150 uL/well. The plate was placed on microplate leader and levels of fluorescence were measured from the bottom of the plate at excitation of 360 nm and emission 460 nm.

As shown in Tables 7-11, serum $C_{max}$ of the recombinant LAL administered to adult patients suffering from late onset LAL deficiency ranged from approximately 270 ng/mL to 720 ng/mL. Half-life ($t_{1/2}$) ranged from 7.6 minutes to 16.7 minutes, and the mean $t_{1/2}$ was approximately 13 minutes (standard deviation, 3.812).

TABLE 7

| Patient ID (Dose: 0.35 mg/kg) | Visit # | Concentration (ng/mL) | Nominal Time |
|---|---|---|---|
| 02-001 | 2 | 5.63 | Pre-infusion |
| 02-001 | 2 | 241.88 | 10 min DI |
| 02-001 | 2 | 369.44 | 15 min DI |
| 02-001 | 2 | 369.93 | 20 min DI |
| 02-001 | 2 | 359.64 | 40 min DI |
| 02-001 | 2 | 294.64 | 60 min DI |
| 02-001 | 2 | 71.85 | 90 min DI |
| 02-001 | 2 | 71.20 | EOI |
| 02-001 | 2 | 37.95 | 5 min AI |
| 02-001 | 2 | 24.91 | 10 min AI |
| 02-001 | 2 | 14.16 | 20 min AI |
| 02-001 | 2 | 9.76 | 30 min AI |
| 02-001 | 2 | 9.02 | 40 min AI |
| 02-001 | 2 | 7.20 | 60 min AI |
| 02-001 | 2 | 7.51 | 120 min AI |

$C_{max}$ = 369.93 ng/mL;
$t_{1/2}$ = 16.8 min;
LLOQ = 4.68 ng/ml

TABLE 8

| Patient ID (Dose: 0.35 mg/kg) | Visit # | Concentration (ng/mL) | Nominal Time |
|---|---|---|---|
| 03-001 | 2 | 8.23 | Pre |
| 03-001 | 2 | 199.80 | 10 min DI |
| 03-001 | 2 | 215.10 | 15 min DI |
| 03-001 | 2 | 228.12 | 20 min DI |
| 03-001 | 2 | 237.25 | 40 min DI |
| 03-001 | 2 | 210.73 | 60 min DI |
| 03-001 | 2 | 262.41 | 90 min DI |
| 03-001 | 2 | 102.39 | EOI |
| 03-001 | 2 | 52.20 | 5 min AI |
| 03-001 | 2 | 33.75 | 10 min AI |
| 03-001 | 2 | 17.60 | 20 min AI |
| 03-001 | 2 | 12.17 | 30 min AI |
| 03-001 | 2 | 10.82 | 40 min AI |
| 03-001 | 2 | 9.39 | 60 min AI |
| 03-001 | 2 | 8.72 | 120 min AI |

$C_{max}$ = 262 ng/mL;
$t_{1/2}$ = 15.3 min;
LLOQ = 4.68 ng/ml

TABLE 9

| Patient ID (Dose: 0.35 mg/kg) | Visit # | Concentration (ng/mL) | Nominal Time |
|---|---|---|---|
| 03-002 | 2 | <4.68 | Pre-infusion |
| 03-002 | 2 | 480.55 | 10 min DI |
| 03-002 | 2 | 531.16 | 15 min DI |
| 03-002 | 2 | 613.85 | 20 min DI |
| 03-002 | 2 | 717.75 | 40 min DI |
| 03-002 | 2 | 84.46 | 60 min DI |
| 03-002 | 2 | 54.34 | 90 min DI |
| 03-002 | 2 | 171.41 | EOI |
| 03-002 | 2 | 87.95 | 5 min AI |
| 03-002 | 2 | 49.70 | 10 min AI |
| 03-002 | 2 | 16.47 | 20 min AI |
| 03-002 | 2 | 11.01 | 30 min AI |
| 03-002 | 2 | 9.76 | 40 min AI |
| 03-002 | 2 | 6.28 | 60 min AI |
| 03-002 | 2 | 5.19 | 120 min AI |

$C_{max}$ = 718 ng/mL;
$t_{1/2}$ = 10.8 min;
LLOQ = 4.68 ng/ml

TABLE 10

| Patient ID (Dose: 0.35 mg/kg) | Visit # | Concentration (ng/mL) | Nominal Time |
|---|---|---|---|
| 02-001 | 6 | 5.12 | Pre-infusion |
| 02-001 | 6 | 249.91 | 10 min DI |
| 02-001 | 6 | 294.37 | 15 min DI |
| 02-001 | 6 | 313.75 | 20 min DI |
| 02-001 | 6 | 330.04 | 40 min DI |
| 02-001 | 6 | 245.48 | 60 min DI |
| 02-001 | 6 | 262.78 | 90 min DI |
| 02-001 | 6 | 81.09 | EOI |
| 02-001 | 6 | 32.10 | 5 min AI |
| 02-001 | 6 | 20.39 | 10 min AI |
| 02-001 | 6 | 10.74 | 20 min AI |
| 02-001 | 6 | 8.08 | 30 min AI |
| 02-001 | 6 | 6.38 | 40 min AI |
| 02-001 | 6 | 5.82 | 60 min AI |
| 02-001 | 6 | <4.68 | 120 min AI |

$C_{max}$ = 330 ng/mL;
$t_{1/2}$ = 15.3 min;
LLOQ = 4.68 ng/ml

TABLE 11

| Patient ID (Dose: 0.35 mg/kg) | Visit # | Concentration (ng/mL) | Nominal Time |
|---|---|---|---|
| 03-001 | 6 | 6.63 | Pre-infusion |
| 03-001 | 6 | 317.45 | 10 min DI |
| 03-001 | 6 | 333.46 | 15 min DI |
| 03-001 | 6 | 310.83 | 20 min DI |
| 03-001 | 6 | 378.68 | 40 min DI |
| 03-001 | 6 | 234.49 | 60 min DI |
| 03-001 | 6 | 246.07 | 90 min DI |
| 03-001 | 6 | 206.06 | EOI |
| 03-001 | 6 | 253.80 | 5 min AI |
| 03-001 | 6 | 70.81 | 10 min AI |
| 03-001 | 6 | 24.61 | 20 min AI |
| 03-001 | 6 | 12.32 | 30 min AI |
| 03-001 | 6 | 9.03 | 40 min AI |
| 03-001 | 6 | 7.18 | 60 min AI |
| 03-001 | 6 | 5.56 | 120 min AI |

$C_{max}$ = 379 ng/mL;
$t_{1/2}$ = 7.7 min;
LLOQ = 4.68 ng/ml

Example 16

Immunogenicity Analysis: Measurement of Anti-SBC-102

Each unknown, positive and negative sample was diluted 1:20 in 5% dry milk in 1×PBS and incubated at 4° C. for 12-18 hours on a rotator (500 rpm). Prior to assay, the samples were centrifuged at 2000×g for 20 minutes and the supernatant was removed to a new 1.5 ml tube.

SBC-102 was diluted in 1×PBS buffer to a concentration of 0.5 ug/mL, and 100 uL was placed to each well of a 96-well ELISA plate. The plate was covered with adhesive cover and incubated at room temperature for 8 hours or overnight at 4° C. After incubation, wells were washed three times with 1× wash buffer. 200 uL of 5% BSA-IgG free was added to each well and the plate was sealed and incubated at 4° C. for 12-18 hours or room temperature for 2 hours. After incubation, the wells were washed three times with 1× wash buffer. 100 uL of each control sample, unknown sample, and negative sample was added to wells in triplicate. The plate was incubated at room temperature for 1.5 hours on microplate shaker (500 rpm). After incubation, the wells were washed three times with 1× wash buffer. 100 uL of biotinylated SBC-102 diluted in dilution buffer to a concentration of 100 ng/mL was added to each well, and the plate was incubated at room temperature for 1.5 hours on a microplate shaker (500 rpm). After incubation, the wells were washed with 1× wash buffer. 100 uL of streptavidin-HRP conjugate diluted to 1:4000 in dilution buffer was added to each well. The plate was incubated at room temperature for 1.5 hour on microplate shaker (500 rpm). After incubation, the wells were washed four times with 1× wash buffer. 100 uL of TMB substrate was added to each well, and the plate was incubated for 15 minutes in the dark. 50 uL of stop solution (0.5N $H_2SO_4$) was added to each well to stop the reaction. OD at 450 nm was measured.

As tabulated in Table 12, the patients who received weekly dose of 0.35 mg/kg of SBC-102 for 4 weeks did not exhibit elevated levels of anti-SBC-102 antibody, suggesting that the enzyme replacement therapy by SBC-102 infusion does not elicit any significant immunogenicity in human patients. These patients did not exhibit any adverse events or infusion-related reaction (IRR).

TABLE 12

| Sample | Mean OD | Std. Dev. | SBC-102 Concentration (ng/ml) |
|---|---|---|---|
| Neg. Ctrol. | 0.056 | N/A | 0 |
| Pos. Ctrl. 1 | 0.076 | 0.005 | 15.6 |
| Pos. Ctrl. 2 | 0.090 | 0.003 | 31.2 |
| Pos. Ctrl. 3 | 0.132 | 0.008 | 62.5 |
| Pos. Ctrl. 4 | 0.201 | 0.009 | 125 |
| Pos. Ctrl. 5 | 0.349 | 0.019 | 250 |
| Pos. Ctrl. 6 | 0.635 | 0.012 | 500 |
| Pos. Ctrl. 7 | 0.958 | 0.101 | 1000 |

| Patient ID | Mean OD | Std. Dev. |
|---|---|---|
| 01-001 Visit1 | 0.053 | 0.000 |
| 02-001 Visit1 | 0.051 | 0.000 |
| 02-001 Visit7 | 0.053 | 0.002 |
| 02-001 Visit8 | 0.050 | 0.001 |
| 03-001 Visit1 | 0.051 | 0.001 |
| 03-001 Visit2 | 0.051 | 0.001 |
| 03-001 Visit7 | 0.050 | 0.000 |
| 03-002 Visit1 | 0.052 | 0.004 |
| 03-002 Visit2 | 0.056 | 0.006 |

Example 17

Treatment of Wolman Disease (WD) by Administration of Recombinant LAL

At 7 weeks of age a female patient is admitted to the hospital because of difficulty in weight gain and poor progress since birth. At the initial physical examination the patient weighs 3.6 kg (birth weight 3.7 kg) and is thin, with loose skin folds. The abdomen is distended, with firm hepatomegaly of 6 cm and firm splenomegaly of about 4 cm. Enlarged lymph nodes are noted in the groin and muscular activity is weak.

The initial hemoglobin level is 9.2 gm, platelets 506,000, and white blood cells 11,550. Urinalysis is normal, and bone marrow smears reveal vacuolated lymphocytes and numerous foam cells. Serum chemical measurements: total lipids 834 mg/100 ml, phospholipids 176 mg/100 ml, triglycerides 141 mg/100 ml, cholesterol 129 mg/100 ml, bilirubin 0.3 mg/100 ml, alkaline phosphatase 9.0 BU %, SGOT 90 units, SGPT 50 units, cholinesterase 20 units, urea nitrogen 8.3 mg, fasting sugar 45 mg/100 ml. CT scan of the abdomen shows hepatosplenomegaly and bilateral symmetrically enlarged adrenal glands with calcification.

The patient is surgically implanted with a venous vascular access port for dosing. After connecting the port to an ambulatory infusion machine, the patient is pretreated with 1 mg/kg of diphenhydramine 20 minutes prior to recombinant LAL infusion in order to counteract potential anaphylactic infusion reactions. The patient is then administered recombinant LAL at 1 mg/kg over the course of 5 hours by intravenous infusion. This therapy is repeated one time every 7 days indefinitely.

Within two weeks of administering the first dose of recombinant LAL, the patient is evaluated for weight gain and size of key abdominal organs as determined by ultrasound. Laboratory results testing lysosomal acid lipase activity in the patient are also performed.

Example 18

Treatment of Cholesteryl Ester Storage Disease (CESD) by Administration of Recombinant LAL A 3-year-old boy with a pruritic abdominal rash is examined by his pediatrician. Upon abdominal examination, hepatomegaly is noted by the physician and confirmed by ultrasound. At this point no diagnosis is made and the patient is monitored periodically.

At age 8, he is admitted to the hospital with gastroenteritis. Light microscopy of a liver biopsy shows increased intracytoplasmic glycogen and small lipid droplets in hepatocytes. Electron microscopy shows membrane-bound lipid droplets with small electron dense granules. A working diagnosis of glycogen storage disease type III (DeBrancher disease) is made, but skin fibroblast Debrancher activity is normal.

At age 10, hepatomegaly persists and a second liver biopsy is taken. light microscopy shows altered lobular architecture of the hepatic parenchyma with distended hepatocytes containing cytoplasmic granules and vacuoles with mild periportal fibrosis. Fibroblast acid lipase activity is found to be 7% of normal, confirming the diagnosis of CESD. Plasma concentrations of total cholesterol (TC), triglycerides (TG), low-density lipoprotein cholesterol (LDL-C) are each above the 95th percentile for age and sex at 7.51, 3.24 and 5.58 mmol/L, respectively, while plasma high-density lipoprotein cholesterol (HDL-C) is below the 5th percentile at 0.47 mmol/L; he has combined hyperlipidemia (hypercholesterolemia, hypertriglyceridemia, hypoalphalipoproteinemia and hyperbetalipoproteinemia).

The patient is surgically implanted with a venous vascular access port for dosing. After connecting the port to an ambulatory infusion machine, the patient is pretreated with 5 mg/kg of diphenhydramine 20 minutes prior to recombinant LAL infusion in order to counteract potential anaphylactic infusion reactions. The patient is then administered recombinant LAL at 5 mg/kg over the course of 5 hours by intravenous infusion. This therapy is repeated one time every 14 days indefinitely.

Within two weeks of administering the first dose of recombinant LAL, the patient is evaluated for weight gain and size of key abdominal organs as determined by ultrasound. Laboratory results testing lysosomal acid lipase activity in the patient are also performed.

Each example in the above specification is provided by way of explanation of the invention, not limitation of the invention. In fact, it will be apparent to those skilled in the art that various modifications, combinations, additions, deletions and variations can be made in the present invention without departing from the scope or spirit of the invention. For instance, features illustrated or described as part of one embodiment can be used in another embodiment to yield a still farther embodiment. It is intended that the present invention cover such modifications, combinations, additions, deletions, and variations.

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

---

What is claimed is:

1. An isolated recombinant human lysosomal acid lipase (rhLAL) as set forth in SEQ ID NO: 1 that contains N-linked glycans attached to $Asn^{15}$, $Asn^{80}$, $Asn^{140}$, $Asn^{252}$ and $Asn^{300}$, wherein the N-linked glycans comprise bi-, tri- and tetra-antennary structures with N-acetylglucosamine (GlcNAc), mannose and/or manose-6-phosphate (M6P), and wherein the rhLAL comprises M6P-containing glycans at $Asn^{80}$, $Asn^{140}$ and $Asn^{252}$.

2. The isolated rhLAL of claim 1, wherein the rhLAL does not contain sialic acid.

3. The isolated rhLAL of claim 1, wherein the rhLAL has a molecular weight of about 55 kD.

4. The isolated rhLAL of claim 1, wherein the rhLAL has a specific activity of at least about 100 U/mg.

5. The isolated rhLAL of claim 1, wherein the rhLAL does not comprise O-linked glycans.

6. The isolated rhLAL of claim 1, wherein $Asn^{51}$ of the rhLAL is not glycosylated.

7. The isolated rhLAL of claim 1, wherein the rhLAL has serum half-life ($t_{1/2}$) that is less than 40 minutes.

8. The isolated rhLAL of claim 1, wherein the N-linked glycans do not comprise fucose and the rhLAL does not contain O-linked glycans.

9. A method of treating a human subject with a lysosomal acid lipase (LAL) deficiency comprising administering the isolated recombinant human LAL of claim 1 to the subject.

10. A method of increasing LAL activity in a human subject with a LAL deficiency comprising administering the isolated recombinant human LAL of claim 1 to the subject.

* * * * *